(12) United States Patent
Chuang et al.

(10) Patent No.: US 7,639,419 B2
(45) Date of Patent: Dec. 29, 2009

(54) INSPECTION SYSTEM USING SMALL CATADIOPTRIC OBJECTIVE

(75) Inventors: Yung-Ho Chuang, Cupertino, CA (US); J. Joseph Armstrong, Milpitas, CA (US); David R. Shafer, Fairfield, CT (US)

(73) Assignee: KLA-Tencor Technologies, Inc., Milpitas, CA (US)

( * ) Notice: Subject to any disclaimer, the term of this patent is extended or adjusted under 35 U.S.C. 154(b) by 640 days.

(21) Appl. No.: 10/615,512

(22) Filed: Jul. 7, 2003

(65) Prior Publication Data

US 2004/0218262 A1 Nov. 4, 2004

Related U.S. Application Data

(63) Continuation-in-part of application No. 10/434,374, filed on May 7, 2003.

(60) Provisional application No. 60/449,326, filed on Feb. 21, 2003.

(51) Int. Cl.
G02B 17/08 (2006.01)
(52) U.S. Cl. ......................... 359/364; 359/355; 359/727
(58) Field of Classification Search ......... 359/364–366, 359/368, 351, 355–357, 729–731, 858–859
See application file for complete search history.

(56) References Cited

U.S. PATENT DOCUMENTS 1,973,066 A 9/1934 Hauser et al.
2,661,658 A 12/1953 Dyson
3,237,515 A 3/1966 Altman
4,155,630 A 5/1979 Ih
4,511,220 A 4/1985 Scully
4,647,158 A 3/1987 Yeadon (Continued)

FOREIGN PATENT DOCUMENTS

DE 108181 1/1900

(Continued)

OTHER PUBLICATIONS

The Photonics Design & Applications Handbook (Book 3), 1999, Laurin Publishing Co. Inc., 45th Edition, pp. H-259 to H-263.*

(Continued)

Primary Examiner—Lee Fineman
(74) Attorney, Agent, or Firm—Smyrski Law Group, A P.C.

(57) ABSTRACT

A system for use with a reduced size catadioptric objective is disclosed. The system including the reduced size objective includes various subsystems to allow enhanced imaging, the subsystems including illumination, imaging, autofocus, positioning, sensor, data acquisition, and data analysis. The objective may be employed with light energy having a wavelength in the range of approximately 190 nanometers through the infrared light range, and elements of the objective are less than 100 mm in diameter. The objective comprises a focusing lens group and at least one field lens oriented to receive focused light energy from the focusing lens group and provide intermediate light energy. The objective also includes a Mangin mirror arrangement. The design imparts controlled light energy with a numerical aperture in excess of 0.65 and up to approximately 0.90 to a specimen for imaging purposes, and the design may be employed in various environments.

25 Claims, 35 Drawing Sheets

U.S. PATENT DOCUMENTS

| | | | |
|---|---|---|---|
| 4,758,088 A | 7/1988 | Doyle | |
| 4,779,966 A | 10/1988 | Friedman | |
| 4,795,244 A | 1/1989 | Uehara | |
| 4,898,471 A | 2/1990 | Vaught et al. | |
| 4,971,428 A | 11/1990 | Moskovich | |
| 4,974,094 A | 11/1990 | Morito | |
| 5,031,976 A | 7/1991 | Shafer | |
| 5,089,913 A | 2/1992 | Singh et al. | |
| 5,114,238 A | 5/1992 | Sigler | |
| 5,140,459 A | 8/1992 | Sagan | |
| 5,162,939 A | 11/1992 | Herron et al. | |
| 5,177,559 A | 1/1993 | Batchelder et al. | |
| 5,233,460 A | 8/1993 | Partlo | |
| 5,264,912 A | 11/1993 | Vaught et al. | |
| 5,274,494 A | 12/1993 | Rafanelli et al. | |
| 5,309,456 A | 5/1994 | Horton | |
| 5,323,263 A | 6/1994 | Schoenmakers | |
| 5,337,170 A | 8/1994 | Khoury et al. | |
| 5,428,442 A | 6/1995 | Lin et al. | |
| 5,434,662 A | 7/1995 | Rockwell et al. | |
| 5,488,229 A | 1/1996 | Elliott et al. | |
| 5,515,207 A | 5/1996 | Foo | |
| 5,621,529 A | 4/1997 | Gordon et al. | |
| 5,636,066 A | 6/1997 | Takahashi | |
| 5,644,140 A | 7/1997 | Biedermann et al. | |
| 5,668,673 A | 9/1997 | Suenaga et al. | |
| 5,717,518 A * | 2/1998 | Shafer et al. | 359/357 |
| 5,729,374 A | 3/1998 | Tiszauer et al. | |
| 5,805,334 A | 9/1998 | Takahashi | |
| 5,805,357 A | 9/1998 | Omura | |
| 5,808,797 A | 9/1998 | Bloom et al. | |
| 5,808,805 A | 9/1998 | Takahashi | |
| 5,835,275 A | 11/1998 | Takahashi et al. | |
| 5,849,468 A | 12/1998 | Sawyer | |
| 5,851,740 A | 12/1998 | Sawyer | |
| 5,861,997 A | 1/1999 | Takahashi | |
| 5,880,891 A | 3/1999 | Furter | |
| 5,990,983 A | 11/1999 | Hargis et al. | |
| 5,999,310 A | 12/1999 | Shafer et al. | |
| 6,064,517 A * | 5/2000 | Chuang et al. | 359/364 |
| 6,191,887 B1 | 2/2001 | Michaloski et al. | |
| 6,275,514 B1 | 8/2001 | Katzir et al. | |
| 6,370,178 B1 | 4/2002 | Papayoanou et al. | |
| 6,388,819 B1 * | 5/2002 | Leidig | 359/716 |
| 6,548,797 B1 | 4/2003 | Ai | |
| 6,692,431 B2 * | 2/2004 | Kazakevich | 600/178 |
| 6,842,298 B1 * | 1/2005 | Shafer et al. | 359/730 |
| 2001/0040722 A1 * | 11/2001 | Shafer et al. | 359/351 |
| 2004/0051957 A1 * | 3/2004 | Liang | 359/656 |

FOREIGN PATENT DOCUMENTS

| | | |
|---|---|---|
| DE | 3742806 | 7/1989 |
| EP | 0798585 | 10/1997 |
| GB | 2269024 | 1/1994 |
| WO | 9712226 | 4/1997 |
| WO | 9908134 | 2/1999 |

OTHER PUBLICATIONS

M.R. Bartz et al., "LED Print Analyzer," IBM Technical Disclosure Bulletin, vol. 14, No. 3, Aug. 1971.

D.S. Goodman, "Darkfield Illuminator Attachment," IBM Technical Disclosure Bulletin, vol. 27, No. 5, Oct. 1984.

J.L.C. Sanz et al., "Automated Visual Inspection with Dark-Field Microscopy," Journal of the Optical Society of America, Nov. 1985, USA, vol. 2, No. 11, pp. 1857-1862.

Carl Zeiss Brochure, "MSM 193 Microlithography Simulation Microscope," 1999.

\* cited by examiner

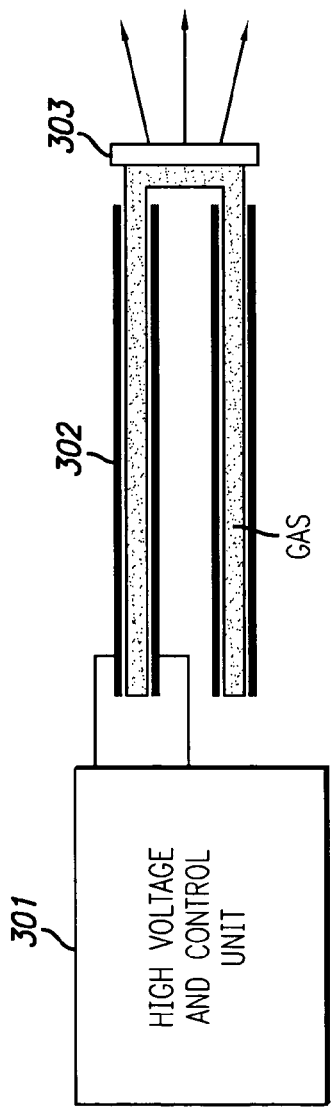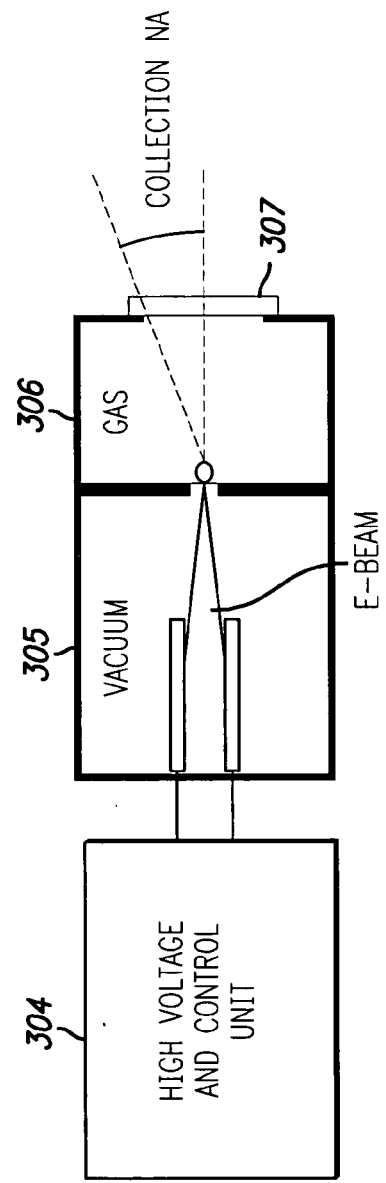

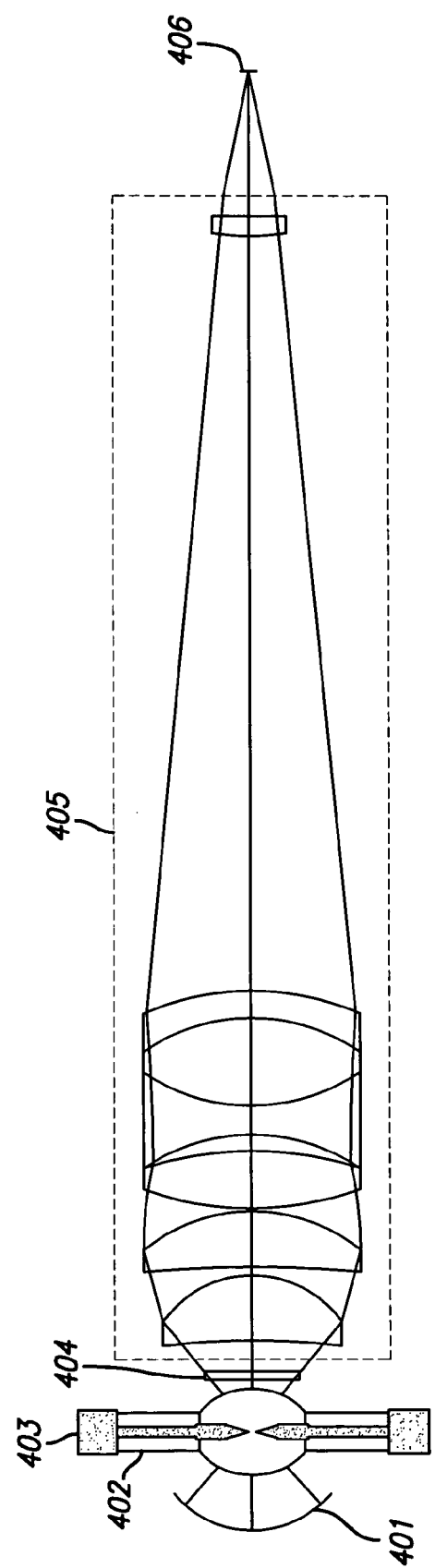

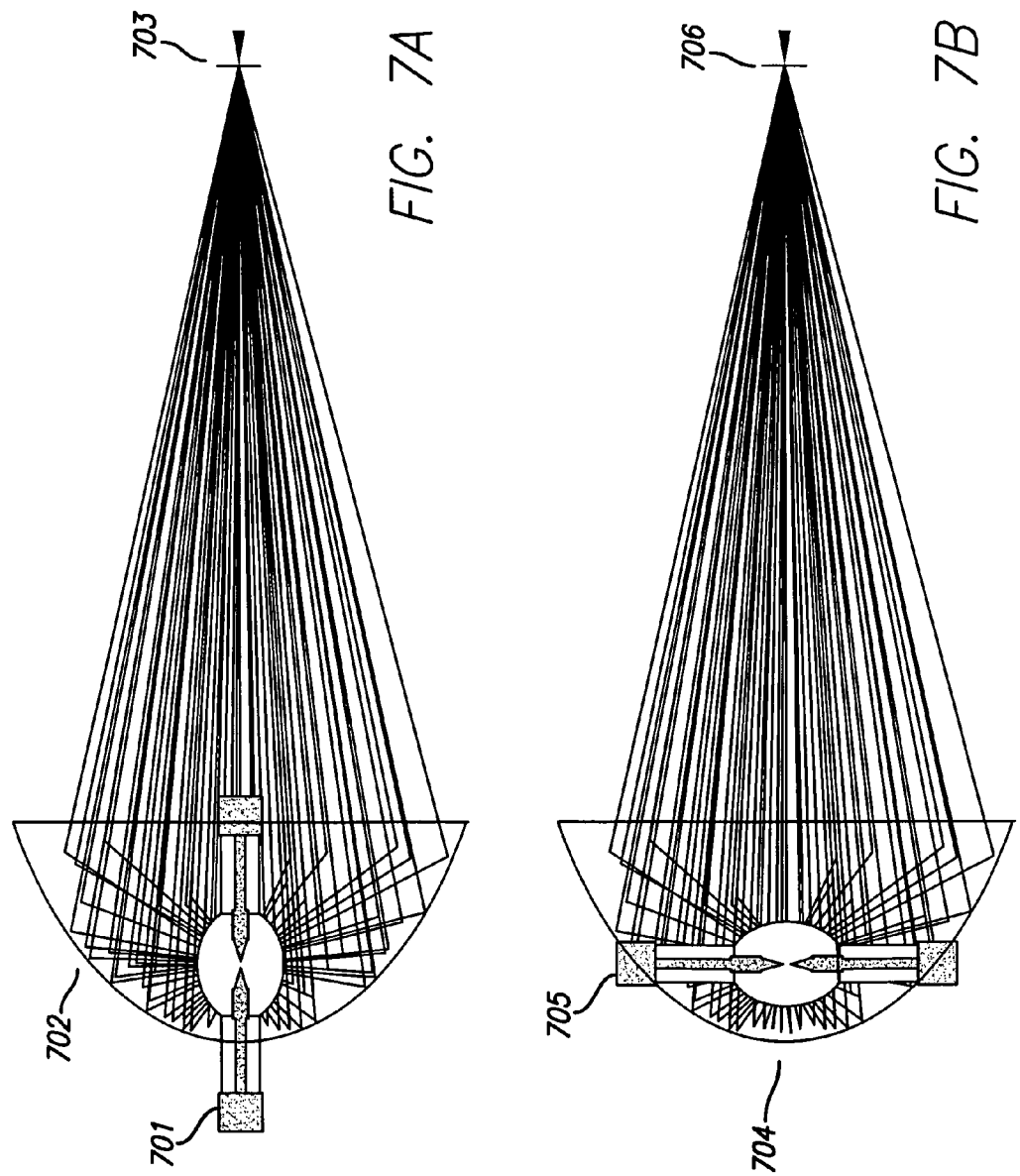

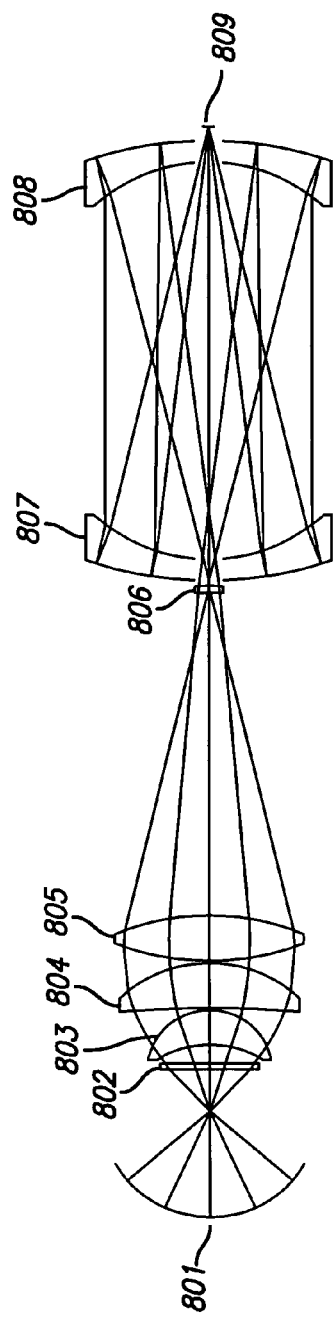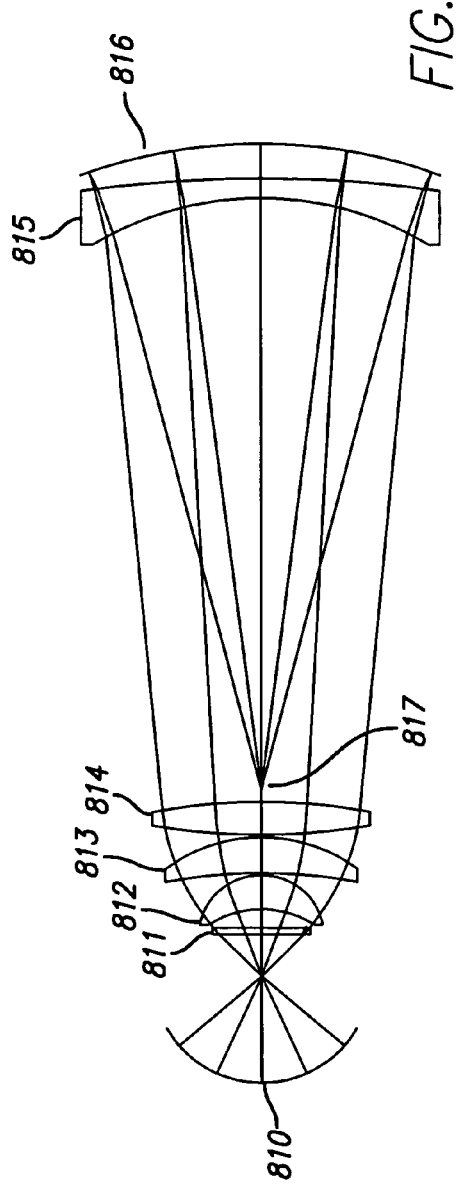

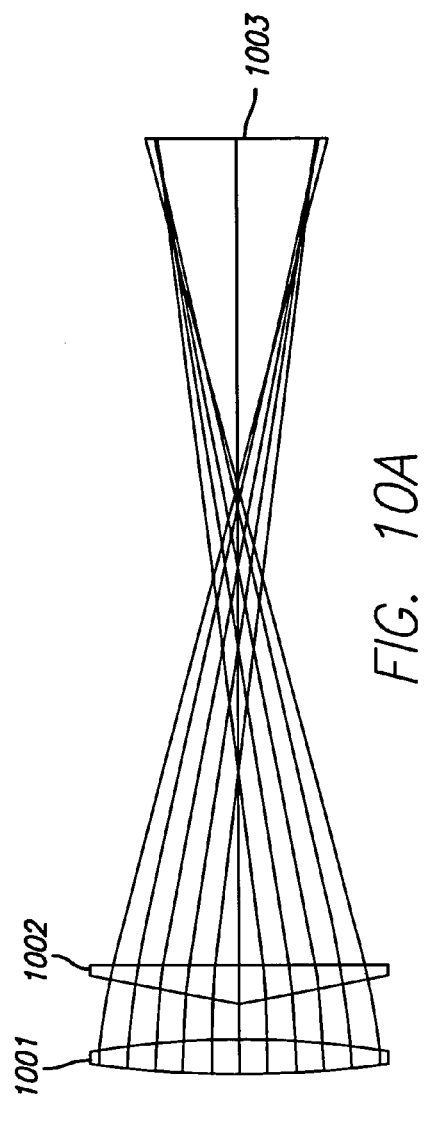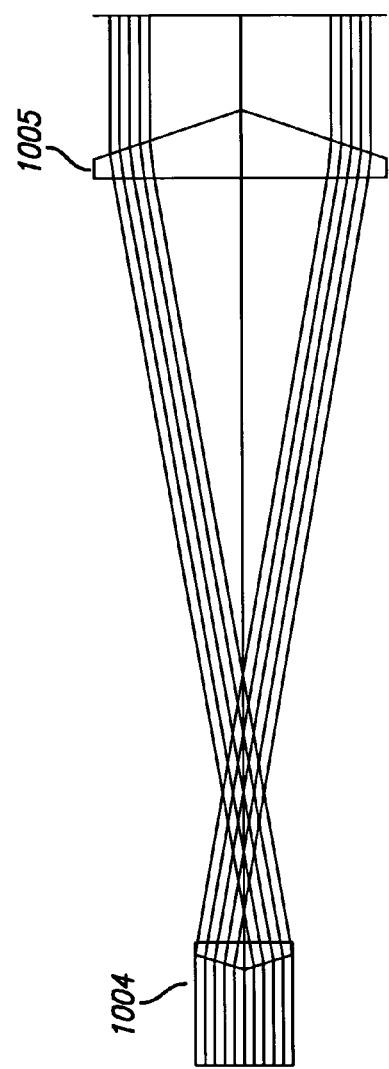
FIG. 10A
FIG. 10B

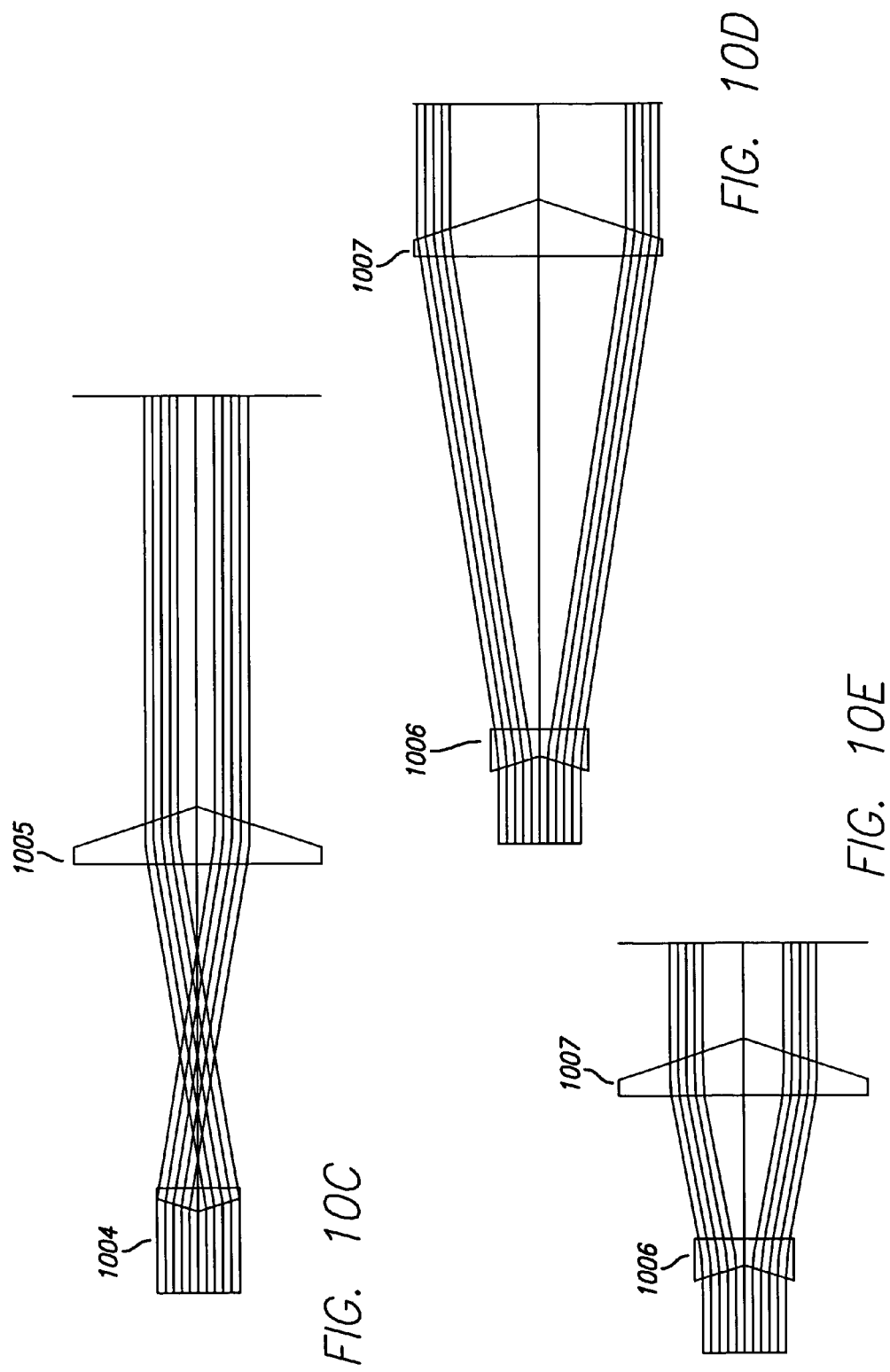

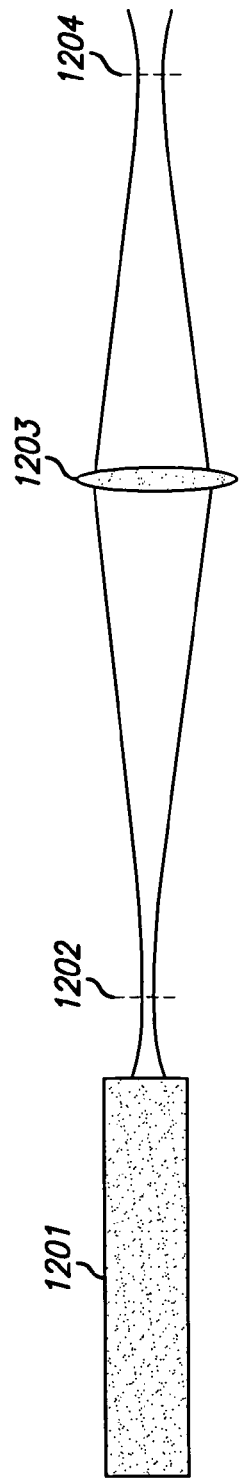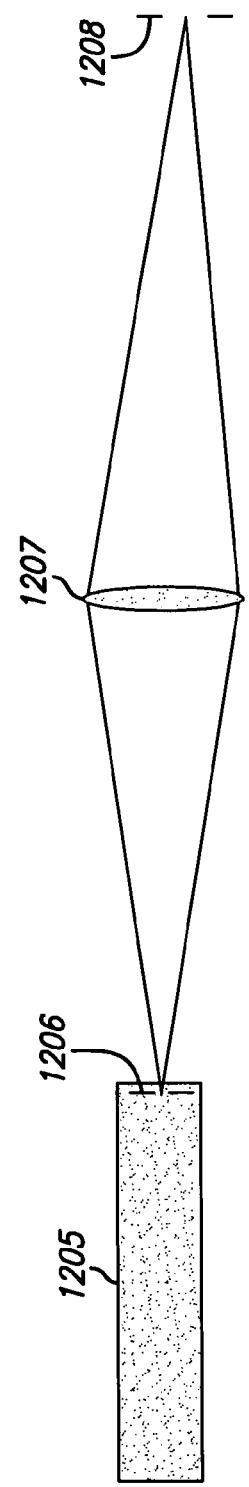
FIG. 12A
FIG. 12B

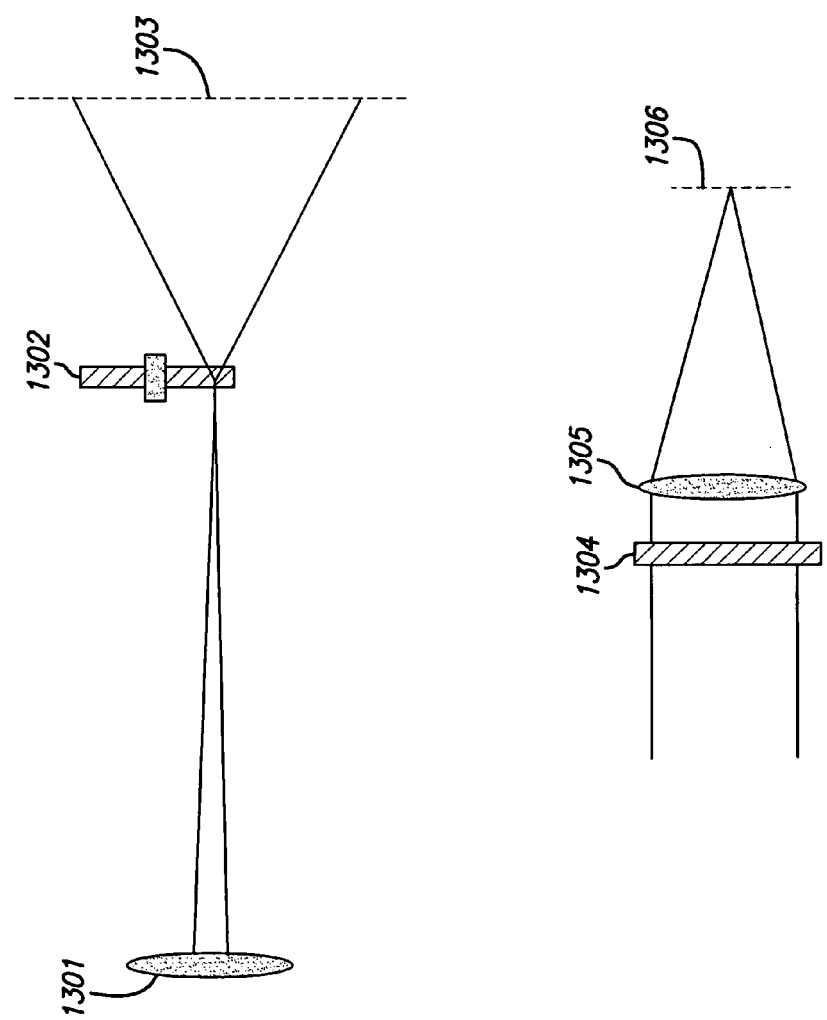

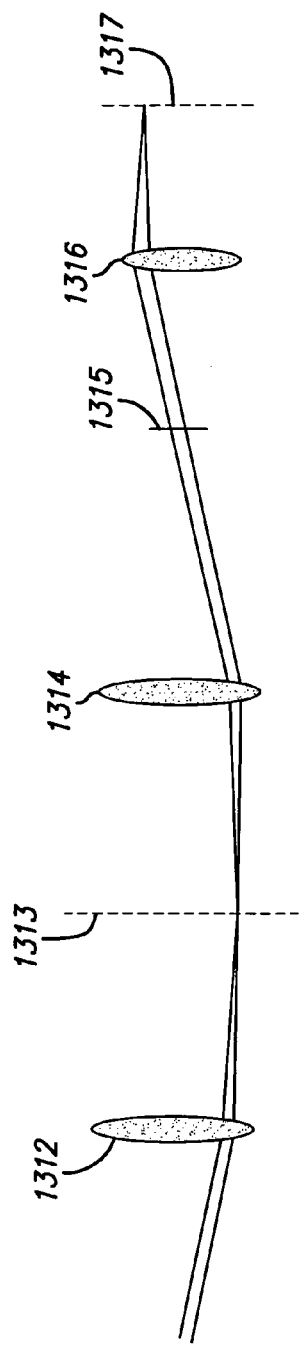
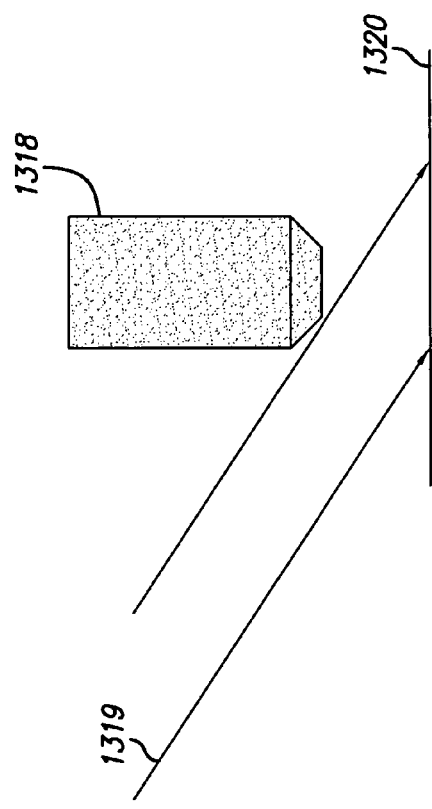
FIG. 13D
FIG. 13E

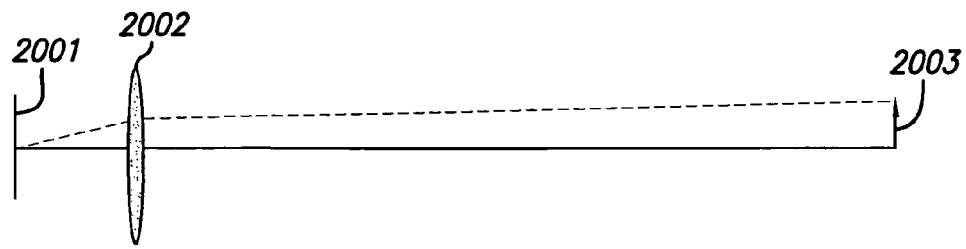
FIG. 20A
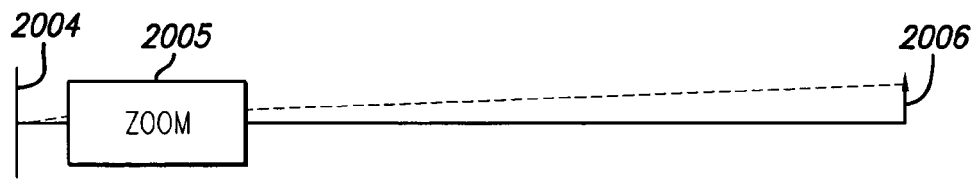
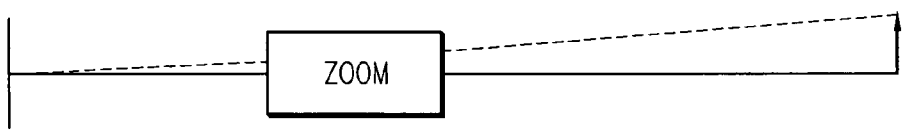
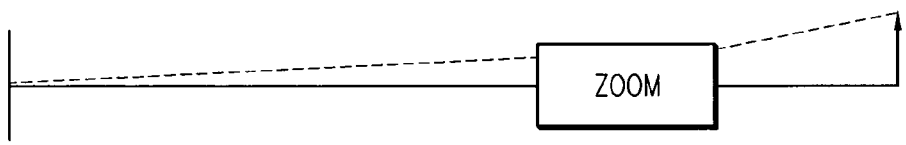
FIG. 20B
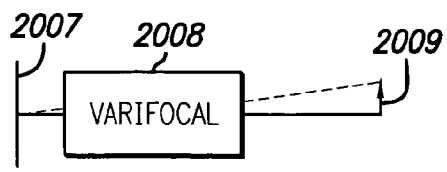
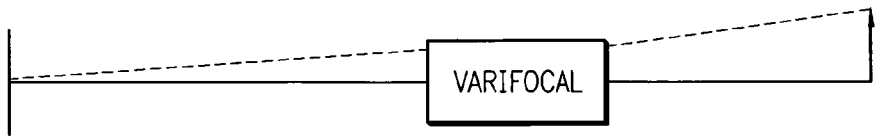
FIG. 20C

INSPECTION SYSTEM USING SMALL CATADIOPTRIC OBJECTIVE

This application is a continuation-in-part of U.S. patent application Ser. No. 10/434,374, filed May 7, 2003, entitled "High Performance Catadioptric Imaging System," inventors Shafer et. al., which claims the benefit of U.S. Provisional Patent Application Ser. No. 60/449,326, entitled "High Performance, Low Cost Catadioptric Imaging System," filed Feb. 21, 2003.

BACKGROUND OF THE INVENTION

1. Field of the Invention

The present invention relates generally to the field of optical imaging and more particularly to optical systems for microscopic imaging, inspection and/or lithography applications.

2. Description of the Related Art

Many optical systems and electronic systems are available to inspect surface features of a specimen for defects., including specimens such as a partially fabricated integrated circuit. Defects on such specimens may be relatively small in size and may take the form of imperfections randomly localized on the specimen surface, such as particles, scratches, process variations, repeating pattern defects, and so forth. Techniques and devices for inspecting specimens for these microscopic defects are generally available in the art and are embodied in various commercially available products, including those available from KLA-Tencor Corporation of San Jose, Calif.

The aim of virtually any type of inspection system or technique is to rapidly and efficiently detect defects. With smaller and smaller features on specimen surfaces and the use of new materials and new manufacturing processes, detection of new and finer defects is required. It is also preferable to rapidly inspect a specimen surface in as short an amount of time as possible, from loading the specimen to removing it from the inspection position and characterizing the defects. Such speed requirements in the presence of smaller features mandate continuous improvements in the available systems and techniques to accurately and adequately find specimen problems.

Current inspection systems are generally based either on refractive objectives or relatively large sized catadioptric objectives. Systems based on refractive objectives are limited due to imaging performance being typically capped at wavelengths above 365 nm. Designs at shorter wavelengths are possible, but only over a very narrow bandwidth. Design of UV objectives having good correction over fields larger than 100 microns with 0.9 NA has also been difficult.

Inspection systems based on large catadioptric objectives can assist with wavelength limitations seen in refractive objectives. Very broad band catadioptric designs may be realized in the deep ultraviolet (DUV) range over relatively large field sizes. Such designs may have limitations including high cost, tight manufacturing tolerances, inflexible system architectures, and difficulty controlling contamination associated with DUV illumination.

Many of the aforementioned imaging systems have been constructed of relatively large components, which are difficult or impossible to employ in small environments, such as microscopes and the like. A smaller inspection objective than has been typically available is disclosed in U.S. patent application Ser. No. 10/434,374, filed May 7, 2003, entitled "High Performance Catadioptric Imaging System," inventors Shafer et. al. The system disclosed therein offers certain imaging components and arrangements for inspecting specimens, but the designs disclosed therein cannot simply be used in all environments for imaging different types of specimens. Inspection systems using different geometries, different light sources, with different performance criteria cannot use the designs of the Ser. No. 10/434,374 application to accurately and adequately assess specimen flaws under all circumstances.

It would therefore be desirable to have a system for inspecting a specimen that improves upon the systems previously available, and in particular for enabling inspection of specimens such as wafers using a small sized catadioptric objective. It would be particularly desirable to offer systems or designs that may be used under various circumstances and with various components that overcome the imaging issues associated with previously known designs.

SUMMARY OF THE INVENTION

According to a first aspect of the present design, there is provided a system for inspecting a specimen. The system comprises an illumination system comprising an arc lamp able to provide light energy having a wavelength in the range of less than approximately 320 nanometers, and an imaging subsystem oriented and configured to receive the light energy from the illumination system and direct light energy toward the specimen, the imaging subsystem comprising a plurality of elements all aligned along a single axis, each element having diameter less than approximately 100 millimeters, wherein the imaging subsystem is configured to provide a field size in excess of approximately 0.4 millimeters at a numerical aperture of approximately 0.90 for the light energy received from the illumination system having the wavelength in the range of less than approximately 320 nanometers.

According to a second aspect of the present design, there is provided a system for inspecting a specimen. The system comprises an illumination system able to provide light energy having a wavelength within a predetermined range, and an illumination subsystem oriented and configured to receive the light energy from the illumination system and direct light energy toward the specimen, the imaging subsystem comprising a plurality of optical elements all aligned along an axis and each having maximum diameter less than approximately 100 millimeters, wherein the imaging subsystem is configured to provide a field size in excess of approximately 0.4 millimeters at a numerical aperture of approximately 0.90.

According to a third aspect of the present design, there is provided a system for inspecting a specimen. The system comprises an illumination system able to provide light energy having a wavelength within a predetermined range, and an imaging subsystem configured to receive the light energy and direct light energy toward the specimen using a plurality of elements having a maximum diameter less than approximately 100 millimeters, the plurality of elements being free of planar reflecting surfaces, wherein the imaging subsystem is configured to provide a field size in excess of approximately 0.4 millimeters at a numerical aperture of approximately 0.90.

According to a fourth aspect of the present design, there is provided a method for inspecting a specimen. The method comprises providing light energy having a wavelength within a predetermined range, and receiving the light energy and directing light energy toward the specimen using a plurality of optical elements aligned collectively along a single axis, each optical element having maximum diameter less than approximately 100 millimeters, wherein the optical elements are configured to provide a field size in excess of approximately 0.4 millimeters at a numerical aperture of approximately 0.90.

These and other aspects of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which:

FIG. 3A illustrates an electrically pumped exciter lamp;

FIG. 3B shows an E beam pumped exciter lamp;

FIG. 4 illustrates refractive lamp collection optics;

FIG. 7A illustrates a reflective collection group using an axially mounted lamp such as an arc lamp;

FIG. 7B is a reflective collection group using a transverse mounted lamp such as an arc lamp;

FIG. 8A shows a catadioptric collection scheme;

FIG. 8B represents an alternate catadioptric collection scheme;

FIG. 10A represents a arrangement employing an ax icon;

FIG. 10B shows a zooming dual axicon system having a first ring illumination;

FIG. 10C shows the zooming dual axicon system of FIG. 10B with the axicon moved thus producing a second ring illumination;

FIG. 10D is an alternate zooming dual axicon system having a first ring illumination;

FIG. 10E represents the alternate zooming dual axicon system of FIG. 10D with the axicon moved thus producing a second ring illumination;

FIG. 12A shows laser collection optics wherein a beam waist is produced;

FIG. 12B shows emission of laser light through an aperture;

FIG. 13A illustrates one aspect of laser beam shaping and relay optics;

FIG. 13B shows an alternate laser beam shaping and relay optics arrangement with collimated input incident on the diffuser or diffractive optic;

FIG. 13D shows relay optics using the concept of selective pupil filtering;

FIG. 13E represents the illumination relay scheme for laser darkfield outside the imaging optics;

FIG. 20A shows a fixed magnification configuration;

FIG. 20B represents a fixed length zoom system;

FIG. 20C is a varifocal magnification configuration;

DETAILED DESCRIPTION OF THE INVENTION

The inspection system and designs disclosed herein employ an imaging subsystem having generally small size, in particular a small sized objective design, that provides advantages over previous catadioptric designs. The present inspection system provides various components and subsystems that may be employed in accordance with a relatively small objective to provide accurate and high quality scans as compared with previously known systems employing relatively small objectives.

Figure 1A:
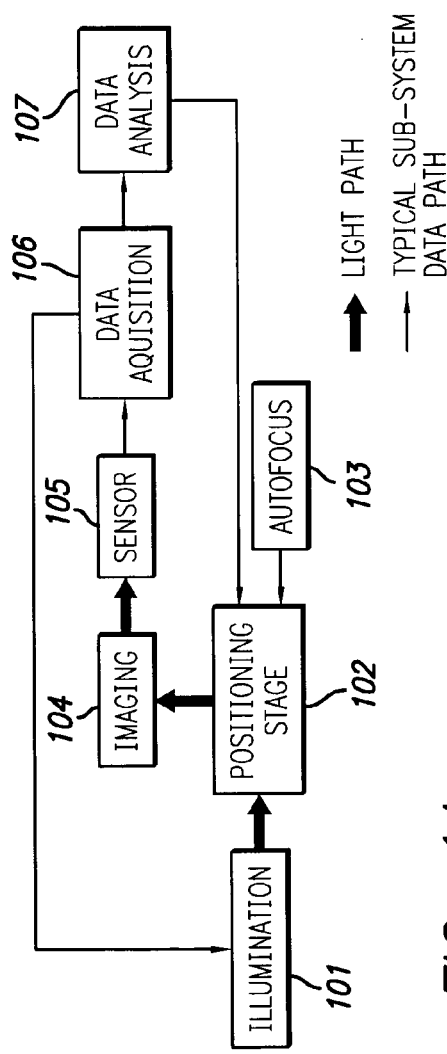
FIG. 1A illustrates typical inspection system components.

FIG. 1A illustrates a typical inspection system having an illumination subsystem 101, positioning stage 102, autofocus subsystem 103, imaging subsystem 104, sensor subsystem 105, data acquisition subsystem 106, and data analysis subsystem 107. The objective in the present design is embodied in the imaging subsystem 104 and will be discussed in detail below. In the arrangement of FIG. 1, light travels via the light path shown from the illumination subsystem 101 to the positioning stage 102, the imaging subsystem 104, and the sensor subsystem or sensor 105. Data passes between the autofocus subsystem 103 and the positioning stage 102 and between the sensor 105 and the data acquisition subsystem 106. Data also passes between the data acquisition subsystem 106 and the illumination subsystem 101, and between the data acquisition subsystem 106 and the data analysis subsystem 107, as well as between the data analysis subsystem 107 and the positioning stage 102.

The purpose of the components depicted in FIG. 1A includes emitting illumination from illumination subsystem 101 to the specimen (not shown), typically maintained and possibly moved using positioning stage 102, whereby light energy passes to the relatively small dimensioned objective, imaging optics, or other imaging components in imaging subsystem 104 and to sensor subsystem 105. Data is acquired from the sensor or sensor subsystem 105 using data acquisition subsystem 106, which may interact with the sensor subsystem to more accurately sense data received, either via positioning, focus, or in some other manner. Data acquired may be analyzed using data analysis subsystem 107, which may include, for example, databases having appearance of known specimens and/or specimen defects. Data analysis information may be fed back to the data acquisition subsystem 106, to for example reacquire data, and may be provided to positioning stage 102 to reposition the specimen. Data acquisition subsystem 106 may also interact with the illumination subsystem 101 to alter illumination characteristics depending on the quality of image received. Finally, autofocus subsystem 103 may be employed with positioning stage 102 to automatically focus the specimen.

Inspection Modes

Many different modes exist for inspecting specimens, including inspecting partially fabricated integrated circuits. Various inspection modes may be employed in accordance with the present system, depending on the application and environment. Inspection modes that may be used with the present design include bright field, ring dark field, full sky, directional dark field, differential interference contrast (DIC), and confocal inspection. These modes can be implemented using reflection of light energy for the purpose of inspecting specimens. The inspection designs employed herein can support one or more of these inspection modes, as well as potentially other inspection modes.

Bright field inspection mode is similar to inspection in common microscope systems where a magnified view of the object or specimen is projected onto a sensor. In bright field imaging, the image produced is readily distinguishable. Image feature size accurately represents the size of object features multiplied by the magnification of the optical system. Thus bright field inspection can be readily employed with image comparison and processing algorithms for computerized object detection and classification of patterned objects. This inspection mode is commonly used for semiconductor wafer inspection.

Dark field inspection mode is primarily used to detect scattering from edges, small particles, and irregular surfaces. For example, smooth flat areas scatter very little light resulting in a dark image. Any surface features, particles, or objects protruding above the flat area scatter light and produce a bright area or region. Dark field inspection modes provide a large signal for small features that have a tendency to scatter the light energy received. This large signal allows larger sensor pixels to be used for a given feature size, permitting faster wafer inspections. Dark field inspection may be used with Fourier filtering, which in specimens having repeating patterns can be used to minimize the repeating pattern signal and enhance the defect signal to noise ratio.

Many different dark field inspection modes exist, including but not limited to ring dark field and directional dark field. Each dark field mode uses a specific illumination and collection scheme such that the scattered and diffracted light collected from the object provides a highly accurate signal. The ring dark field inspection mode consists of illumination and imaging pupils that do not overlap. A typical example of this is an illumination NA that delivers light to the wafer through the high NA portion of the optical pupil. An aperture in the imaging pupil is used to block the central portion of the NA used for illumination and allow scattered light collected in the outer portion of the imaging pupil to pass and form an image. Features on the wafer may be illuminated uniformly from all directions, and features with different orientations are equally well imaged. The numerical apertures (NAs) can also be reversed with the illumination passing through the central portion of the NA and the imaging reflecting and passing along the outer portion of the NA.

Directional dark field inspection mode can be employed in various configurations, typically depending on the particular type of defect encountered or expected to be encountered. One configuration, sometimes referred to as aperture shaping, uses apertures placed at the illumination and imaging pupils. Apertures are used to select different portions of the illumination and imaging pupils. For example, an aperture can be placed near the edge of the illumination pupil, thereby effectively delivering a small cone of light at a high incident angle to the wafer. Another aperture or apertures can then be placed in the imaging pupil to select a desired portion of the scattered light. For example, two apertures can be placed 90 degrees from the illumination pupil aperture selecting the light scattered sideways from features on the wafer. Other illumination and imaging pupil apertures can be used to optimize for specific defect types. Another configuration, sometimes referred to as laser directional dark field, uses one or more lasers that illuminate the sample at high angles of incidence from outside the objective. Often four illumination beams are chosen at 90 degrees offset from each other. This geometry tends to minimize any directional dependence of features on the sample. A further configuration, sometimes called internal laser dark field, is a hybrid of the aperture shaping and the laser directional dark field modes. In laser dark field, the system injects a laser beam into a specific location in the illumination pupil of an optical system.

Full sky optical configuration combines aspects of bright field and ring dark field inspection. Full sky uses differing amounts of attenuation so the relative bright field signal and dark field signal can be adjusted, thus allowing detection of both bright field and dark field defects simultaneously using the same sensor.

Differential Interference Contrast (DIC) inspection provides the ability to resolve gradients in the topology of object-features. In DIC, image contrast increases for increasing gradients in the optical path. DIC mode uses a spatial shearing system with the shear distance on the order of the optical system resolution, and is typically implemented by separating the illumination into two orthogonal polarized beams. These beams interact with the features on the object and are recombined before the image is formed.

Confocal inspection can resolve the topology differences of object features. Most optical configurations have difficulty detecting changes in the topology of features. The confocal configuration discriminates between different heights by using apertures near the illumination and imaging focus. Laser illumination can also be used to eliminate the need for the illumination aperture.

Illumination

A general illumination system as employed in the current design is composed of several different functional groups including a light source 101, collection optics 102, beam shaping and uniformity components 103, and relay optics 104. The collection optics 102, beam shaping and uniformity components 103, and relay optics 104 receive and refine the light energy before delivering the resultant light energy to the sample 105. The light source 101 can be either lamp or laser based. Lamp and laser based light sources include certain differences in design.

Figure 1B:
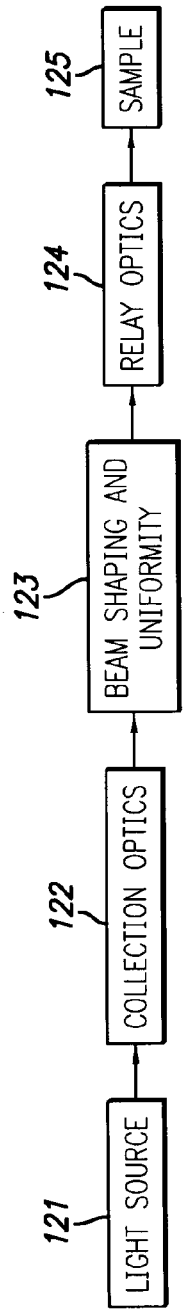
FIG. 1B is a general illumination system.
Figure 1C:
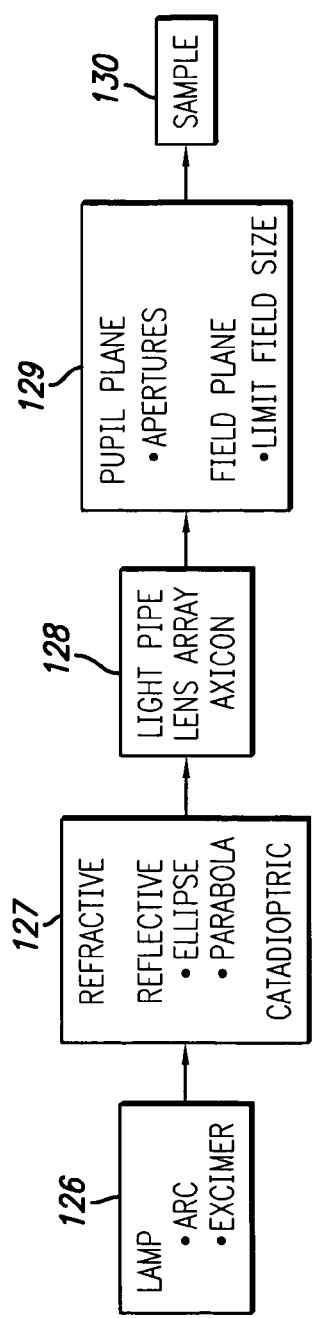
FIG. 1C is a lamp based illumination system.
Figure 1D:
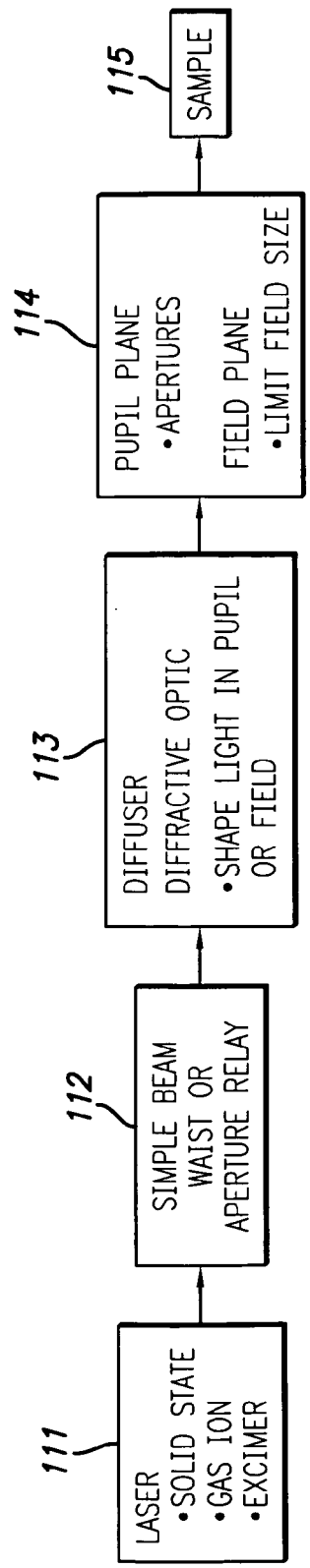
FIG. 1D is a laser based illumination system.

FIGS. 1B, 1C, and 1D are conceptual system arrangements that may be employed in accordance with the current objective. FIG. 1B is a general illumination system having a light source 121, collection optics 122, beam shaping and uniformity elements 123, relay optics 124, and the sample 125. FIG. 1C illustrates a lamp based illumination system having a lamp 126, which may be an arc lamp or excimer lamp, collection optics 127 which may be refractive, reflective (ellipse or parabola), or catadioptric, beam shaping elements 128, including a light pipe, lens array, or axicon, and relay optics 129, potentially including pupil plane relay optics such as apertures or field plane optics such as field size limiters. Sample 130 receives light energy in this lamp based illumination system. FIG. 1D shows a laser based illumination system, with laser 111 being potentially solid state, gas, or excimer based. Collection optics 112 may include a simple beam waist arrangement or aperture relay. Beam shaping and uniformity elements 113 may include a diffuser or diffractive optic such as light shaping elements in the pupil or field plane. Relay optics 114 potentially include pupil plane relay optics such as apertures or field plane optics such as field size limiters. The elements shown and listed in FIGS. 1b, 1C, and 1D are meant to be examples, and other elements besides those listed may be employed. For example, and not by way of limitation, elements beyond a diffuser and diffractive optic may be used for beam shaping in the laser based illumination system of FIG. 1D.

A lamp illumination system consists of a lamp source 126. Various lamps may be employed, including but not limited to arc lamps, excimer lamps, and filament based lamps. Lamp sources in this environment typically exhibit high brightness, high stability, and long lifetime. Lamp brightness and lamp stability can be beneficial to high speed inspection. Lamp power variations may be corrected by measuring these fluctuations with a diode and compensating for changes in signal level. Lamp lifetime is the duration for which the brightness and stability requirements are maintained. Relatively low brightness sources may also be employed depending on the environment, specimen type, and desired results.

Figure 2:
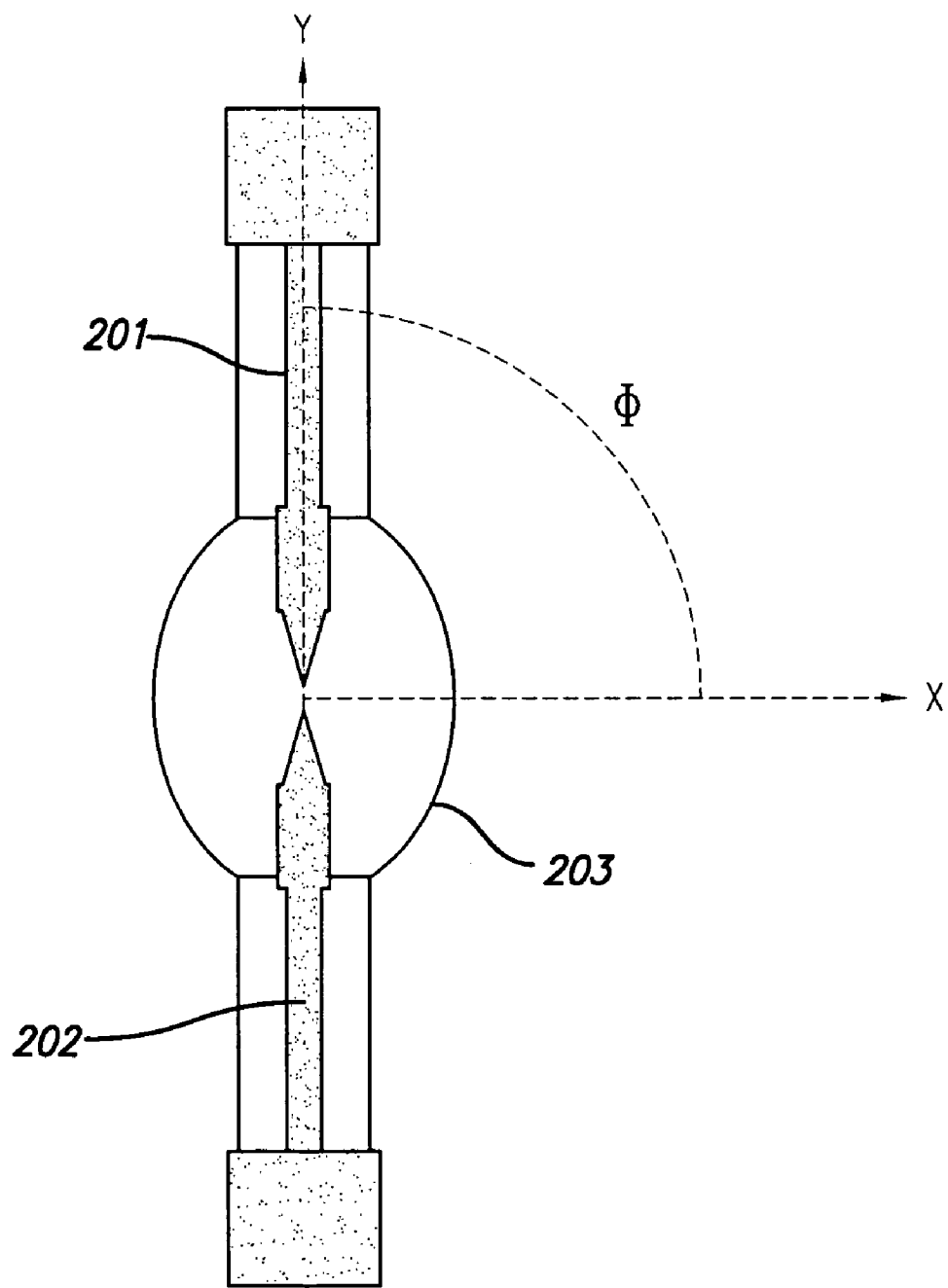
FIG. 2 illustrates components and performance of an arc lamp.

Arc lamps as shown in FIG. 2 may be employed and are available in various types, including but not limited to Mercury, Xenon, and combination Mercury-Xenon. Metal halide, Cadmium, and Deuterium varieties may also be employed. These lamp types generally provide high brightness and can cover a broad spectral range. Short arc gap Mercury Xenon lamps in particular can be good light sources for semiconductor wafer inspection due to their high brightness in the UV-DUV spectral range. Xenon arc lamps have a very uniform spectrum without spectral lines associated with HgXe lamps. The anode 201, cathode 202, and lamp envelope 203 are typically maintained at a predetermined temperature to obtain relatively long lifetimes and high stability. In the arc lamp arrangement of FIG. 2, emission is symmetric about the Y axis shown, and emission in Φ falls off due to shadowing from the anode 201 and cathode 202.

Excimer lamps may use excimer transitions in gasses similar to excimer lasers. Excimer lamps may be in continuous operation. Excimer lamps can also be electrically pumped as shown in FIG. 3A and e-beam pumped as shown in FIG. 3B. Excimer lamps may be employed at very short wavelengths in the vacuum ultraviolet (VUV) range where few other operable light sources exist. The wavelength range for this type of lamp can be as broad as 40-50 nm. Electrically pumped lamps use high voltage 301 to electrically excite excimer gas between electrodes 302. Light exits through window 303. E-beam pumped lamps use high voltage to produce an e-beam 305, which generally produces high brightness. The e-beam may be focused through a silicon nitride barrier between the vacuum and the excimer gas 306. Light then may exit through window 307.

Filament based lamps including but not limited to Tungsten halogen lamps can also be useful light sources, especially for applications with wavelengths greater than 400 nm. Such filament based lamps are generally not suitable for high speed inspection applications due to their low intrinsic brightness.

Dopant materials can be added to the gas mixture to enhance specific spectral regions. A large range of wavelengths are available from different arc lamps.

The following table shows the typical wavelengths for the different generally available and generally applicable light sources.

| Lamp variety | Lamp type | Wavelengths |
| --- | --- | --- |
| Arc lamp | Mercury | 220 nm->1000 nm |
|  | Xenon | 220 nm->1000 nm |
|  | Mercury/Xenon | 220 nm->1000 nm |
|  | Cadmium | 210 nm-225 nm |
|  | Metal Hallide | 220 nm->1000 nm |
|  | Deuterium | 150 nm->300 nm |
| Excimer lamp | Electrically pumped | 121, 126, 147, 172, 157, 193, 248, 308, 351 nm |
|  | e-beam pumped | 60, 80, 121, 126, 147, 172, 157, 193, 248, 308, 351 nm |
| Filament lamp | Tungsten halogen | 400 nm->1000 nm |

These lamps may be used for either pulsed or continuous operation. The illuminator employed in the present system may be optimized to provide the correct operating environment for the lamp, thereby-providing relatively long life.

The collection group of the present system utilizes a significant amount of the light received from high brightness sources. Lamp output distribution in combination with the collection scheme provide the ability to optimize light delivered to the beam shaping group. Many different collection group schemes are possible and may be employed in the present system. The collection group schemes tend to fall into three major categories: all refractive, all reflective, and catadioptric. The best approach for the illumination system depends on the wavelength range, the geometry of the inspection, the specimen used, desired performance, types of anomalies encountered, and power requirements.

A reflective collection group using a refractive condenser with a reflective backing mirror provides certain inspection advantages. FIG. 4 illustrates a sample refractive collection group. Reflector 401 is positioned proximate arc lamp 403, including anode 402, which transmits direct and reflected light energy to lens. 404 and lensing group 405. The lensing group 405 is constructed to provide focused light energy to point 406.

Figure 5:
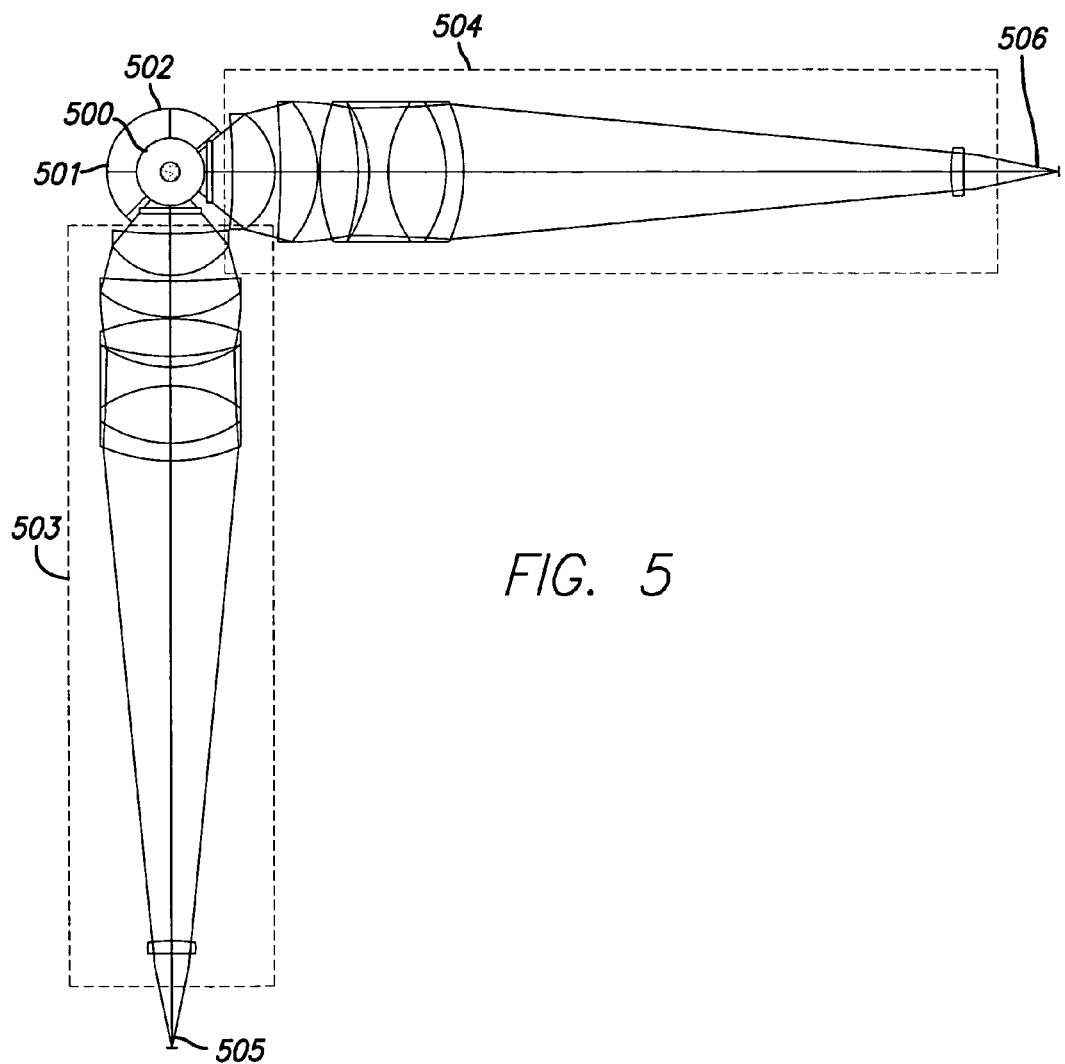
FIG. 5 shows a dual channel refractive lamp collection arrangement.

Sufficient monochromatic aberration correction is possible using such a design, and may be achieved over a wide wavelength range. Designs covering 365-700 nm wavelengths are achievable. Use of a refractive collector group approach may yield complexities in producing an arc image having sufficient aberration correction when a large spectral bandwidth in the UV-DUV is desired. Complexities in producing an arc image having sufficient aberration correction are due to the limitation of fused silica and calcium fluoride being the only available glass materials. In addition, as condensers typically achieve relatively high temperatures, calcium fluoride does not provide adequate materials performance due to the relatively large coefficient of thermal expansion. Efficiency of the backing mirror is also limited as light passes through the arc lamp twice in this orientation. Light energy therefore passes three times through the lamp envelope and possibly back through a portion of the lamp arc. Uncollected light may be employed if a second condenser is included in the design. FIG. 5 shows an overhead or top view of a dual channel refractive condenser arrangement, having arc lamp 500 and a reflective surface comprising first spherical reflective surface 501 and second spherical reflective surface 502. Lensing group 503 transmits reflected and direct light energy to point 505, while lensing group 504 transmits reflected and direct light energy to point 506. In this arrangement,.two channels of inspection may be obtained from a single arc light energy source.

Figure 6:
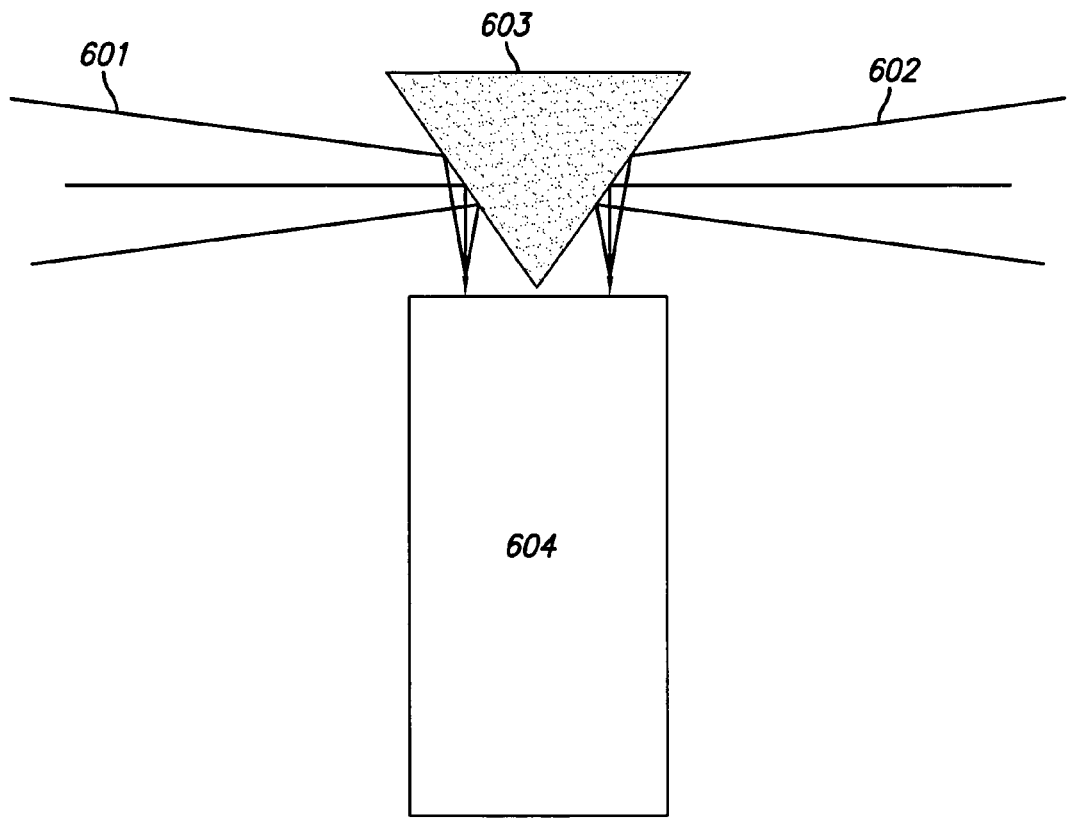
FIG. 6 is a uniformity group including a prism.

This second condenser can be used in combination with the first condenser to increase the averaged brightness in the uniformity group or can be designed for a different wavelength band. To increase averaged brightness, both condenser images and backing mirror images may be folded into a uniformity group. The function of the uniformity group is to provide a uniform light emission or arrangement based on light received by the reflective collection group. One example of folding the images into a uniformity group is shown in FIG. 6, whereby two images are folded into a light pipe. Light from a first condenser system 601 and light from a second condenser system.602 are incident on a prism 603 with reflective coatings on the surfaces. The light reflected from these surfaces then enters the light pipe 604. For this arrangement to produce increased brightness, high efficiency mirror coatings are typically employed. Energy from a single arc image may then sufficiently underfill the light pipe. This approach can also be used with condensers optimized for different wavelengths.

A reflective collection group using an ellipse may also be employed. An all reflective system tends not to suffer any chromatic aberration, and thus can support a very wide bandwidth even in the UV-DUV wavelength. Coatings that only reflect the desired wavelength can be used. Using these special reflective coatings, unwanted light from the lamp can be separated from the desired spectrum. A reflective collection group can also collect a substantial portion of the light produced by the lamp. Some examples of a reflective collection group using an ellipse are shown in FIGS. 7A and 7B. In FIG. 7A, lamp 701 is placed with the arc at one focus of the ellipse 702. Light collected from the lamp 701 may be concentrated at the second focus 703. An alternative arrangement is shown in FIG. 7B with the lamp 704 oriented transverse to the ellipse 705. Light collected by ellipse 705 is concentrated at the second focus 706. Reflective collectors can have strong aberrations for points away from the focus. An elliptical reflector secondary focus can be quite large, reducing the amount of usable light that can enter the smoothing group. This reduction in amount of usable light makes ellipse collection more desirable for large invariants. Reflective collection schemes also typically have a central obscuration due to the shadowing produced by the lamp. Central obscuration is less of an issue when combined with an imaging system that also has a central obscuration. In this configuration, cooling the lamp to operate at a reasonable temperature can be challenging due to the orientation of the mirror around the lamp.

A catadioptric collection group combines the advantage of the high aberration correction of a condenser or condensers with an increased spectral bandwidth present in reflective systems. A catadioptric collector group can, however, require central obscurations, which may be relatively small. One catadioptric design is presented in FIG. 8A, while another is shown in FIG. 8B. The designs of FIGS. 8A and 8B tend to be well corrected over large bandwidths. In FIG. 8A, a lens group collects light received from the lamp arc. The lens group includes blast window 802 and three lens elements 803, 804, and 805. Light is focused through field lens 806 and through an aperture in mangin mirror element 807. Light is then reflected first by mangin element 808 and then by mangin mirror element 807 before being focused through an aperture in mangin element 808 to an image at point 809. Light from the lamp also reflects of the backing mirror 801 before passing in proximity to the lamp arc and through elements 802-808. The design of FIG. 8A is given in the following table.

| SRF | RADIUS | THICKNESS | GLASS |
|---|---|---|---|
| 0 | — | 20.0000 | AIR |
| 1 | — | 3.0000 | Fused silica |
| 2 | — | 9.0000 | AIR |
| 3 | −49.1737 | 16.0000 | Fused silica |
| 4 | −30.2481 | 1.0000 | AIR |
| 5 | −588.9004 | 21.0000 | Fused silica |
| 6 | −61.4435 | 1.0000 | AIR |
| 7 | 127.4395 | 21.0000 | Fused silica |
| 8 | −122.7940 | 152.1385 | AIR |
| 9 | −304.0543 | 3.0000 | Fused silica |
| 10 | −51.0877 | 12.9982 | AIR |
| 11 | — | 185.8013 | AIR |
| 12 | −77.3238 | 10.0000 | Fused silica |
| 13 | −173.5956 | −10.0000 | REFLECT |
| 14 | −77.3238 | −185.8013 | AIR |
| 15 | 77.3238 | −10.0000 | Fused silica |
| 16 | 173.5956 | 10.0000 | REFLECT |
| 17 | 77.3238 | 202.8031 | AIR |

From the foregoing table, as with all other tables including lens prescriptions used herein, SRF represents the surface number associated with a particular element. Most elements have two surfaces, and thus correlating FIG. 8A with the foregoing table, surface 0 is 20.0000 mm from the focal point of element 801, and is 3.0000 millimeters thick, formed of fused silica (surface 1 in the foregoing table), and element 802 is 9.0000 millimeters away from the next element, namely the left surface of element 803 (surface 3). The left surface of surface 3 has a radius of −49.1737 mm, a thickness of 16.0000 mm, and is formed of fused silica. In this manner, every surface in the figures presented can be ascertained.

In FIG. 8B, light from the lamp arc is collected by a lens group consisting of a blast window 811 and three lens elements 812, 813, and 814. Light passes through lens 815, reflects off mirror 816, and passes back through lens 815 again before forming an image at 817. Light from the lamp also reflects off the backing mirror 810 before passing in proximity to the lamp arc and through elements 811-816. The design of FIG. 8B is given in the following table.

| SRF | RADIUS | THICKNESS | GLASS |
|---|---|---|---|
| 0 | — | 20.0000 | AIR |
| 1 | — | 3.0000 | Fused silica |
| 2 | — | 9.0000 | AIR |
| 3 | −47.7113 | 16.0000 | Fused silica |
| 4 | −31.6072 | 1.0000 | AIR |

-continued

| SRF | RADIUS | THICKNESS | GLASS |
|---|---|---|---|
| 5 | −223.8971 | 17.0000 | Fused silica |
| 6 | −71.3507 | 1.0000 | AIR |
| 7 | 265.4157 | 15.0000 | Fused silica |
| 8 | −261.7029 | 281.6651 | AIR |
| 9 | −144.6659 | 10.0000 | Fused silica |
| 10 | −574.2186 | 16.0000 | AIR |
| 11 | −224.1367 | −16.0000 | REFLECT |
| 12 | −574.21855 | −10.0000 | Fused silica |
| 13 | −144.66591 | −276.6720 | AIR |

Figure 8C:
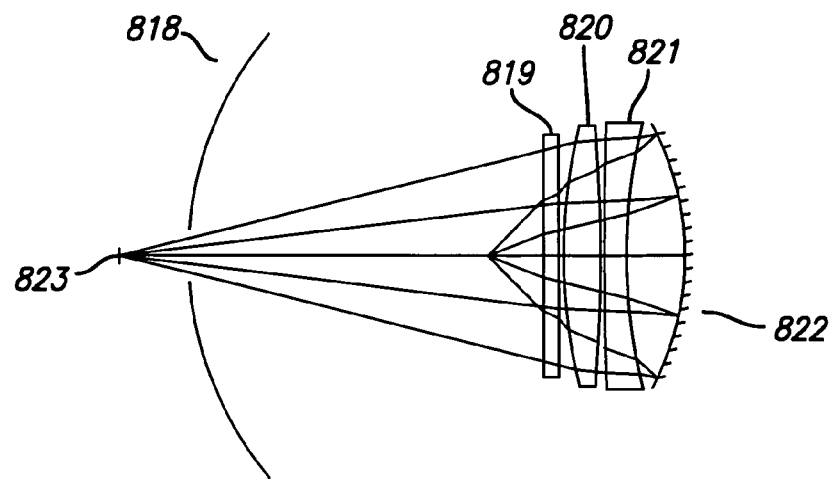
FIG. 8C is another catadioptric collection scheme.

In certain instances, large collection angles are not attainable using this design, as the lamp begins obscuring a large part of the returning light when a large collection angle is employed. Such a consideration applies to, for example, the designs of FIGS. 8C and 8D. These designs are well corrected over a broad wavelength range. In FIG. 8C, light from the lamp arc passes through a lens group consisting of blast window 819 and lens elements 820 and 821. Light then reflects from mirror 822 and passes back through elements 821, 820 and 819 before passing through a hole in mirror 818 and forming an image 823. Light also reflects from 818 and passes in proximity to the lamp reflects before passing through elements 819-821, reflecting of mirror 822, and passing back through elements 821-819 and forming a secondary image at 823. The design of FIG. 8C is given in the following table.

| SRF | RADIUS | THICKNESS | GLASS |
|---|---|---|---|
| 0 | — | 20.0000 | AIR |
| 1 | — | 5.0000 | Fused silica |
| 2 | — | 2.0000 | AIR |
| 3 | 199.8486 | 13.0000 | Fused silica |
| 4 | −415.7655 | 1.0000 | AIR |
| 5 | 1641.4099 | 8.0000 | Fused silica |
| 6 | 210.8969 | 20.0000 | AIR |
| 7 | −95.3976 | −20.0000 | REFL_HATCH |
| 8 | 210.8969 | −8.0000 | Fused silica |
| 9 | 1641.4099 | −1.0000 | AIR |
| 10 | −415.7655 | −13.0000 | Fused silica |
| 11 | 199.8486 | −2.0000 | AIR |
| 12 | — | −5.0000 | Fused silica |
| 13 | — | −125.0000 | AIR |
| 14 | 128.0000 | −22.9308 | AIR |

Figure 8D:
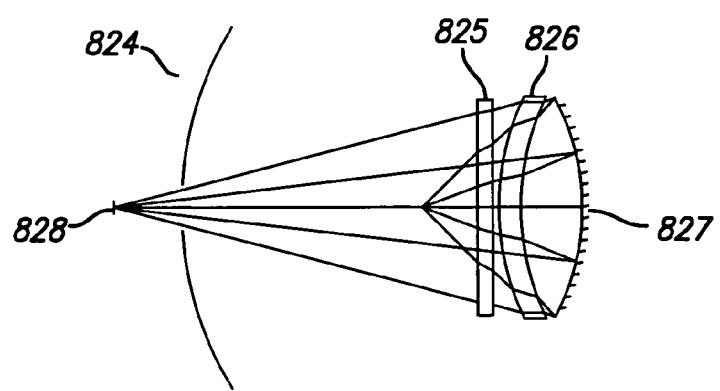
FIG. 8D shows yet another catadioptric collection scheme.

In FIG. 8D, light from the lamp arc passes through a lens group consisting of blast window 825 and lens element 826. Light then reflects from mirror 827 and passes back through elements 826 and 825 before passing through a hole in mirror 824 and forming an image 828. Light also reflects from 824 and passes in proximity to the lamp arc before passing through elements 825 and 826, reflecting of mirror 827, and passing back through elements 826 and 825 and forming a secondary image at 828. The design of FIG. 8D is given in the following table.

| SRF | RADIUS | THICKNESS | GLASS |
|---|---|---|---|
| 0 | — | 20.0000 | AIR |
| 1 | — | 5.0000 | Fused silica |
| 2 | — | 2.0000 | AIR |
| 3 | 90.4530 | 7.9942 | Fused silica |
| 4 | 97.4069 | 22.0000 | AIR |
| 5 | −78.4828 | −22.0000 | REFL_HATCH |
| 6 | 97.4069 | −7.9942 | Fused silica |
| 7 | 90.4530 | −2.0000 | AIR |
| 8 | — | −5.0000 | Fused silica |
| 9 | — | −105.0000 | AIR |
| 10 | 128.0000 | −23.9443 | AIR |

Figure 9A:
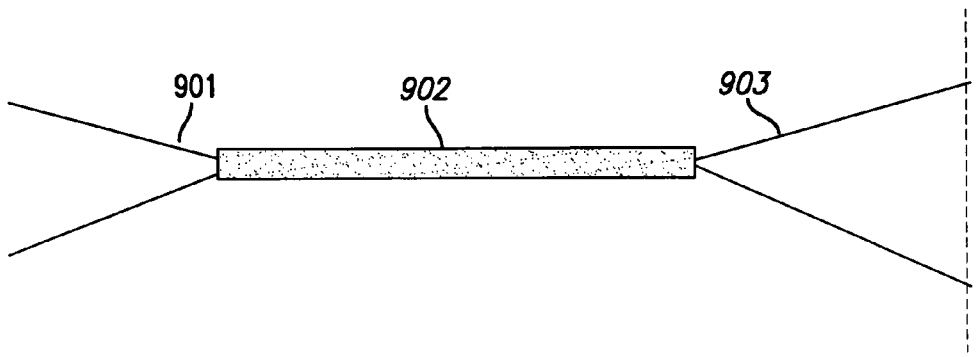
FIG. 9A illustrates a homogenizing rod.

A beam shaping and uniformity functional group can provide desirable illumination profiles in the field and pupil planes. In most imaging systems, it can be desirable to have uniform illumination at the field plane, thereby improving the image for direct viewing and minimizing electronic correction required for computer based image analysis. On technique for obtaining a uniform plane illumination plane is to use a homogenizing rod as shown in FIG. 9A. Focusing light enters the homogenizing rod at the entrance face 901 and reflects down the length of the-rod 902. Different incident angles are sampled into different entrance face 901 angles. Each beam overlaps at the exit of the homogenizing rod 903 to produce a highly uniform illumination plane. These rods may be constructed from glass and may utilize total internal reflection for high efficiency. Fused silica may be used for UV applications. A hollow rod having mirror coatings to create reflections may also be employed. The hollow rod design can allow a much smaller rod to be constructed, generally at the expense of transmission capability. Hexagonal cross sections can also be employed to more efficiently fill circular planes. Another advantage is that a light pipe can support a large invariant. Smaller light pipe cross sections will in general produce higher averaged brightness, and in the present design, multiple light pipes may also be employed.

Figure 9B:
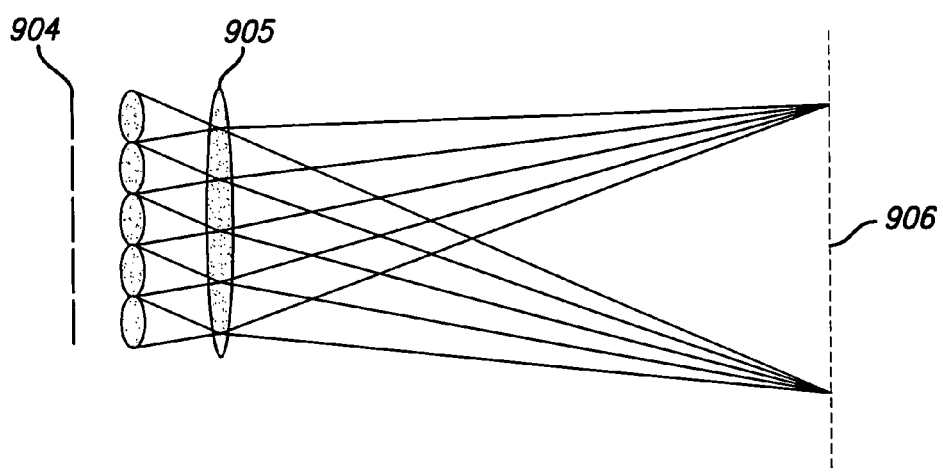
FIG. 9B is a lens array used to produce a uniform illumination plane.

Lens arrays can also be used to produce a uniform illumination plane as shown in FIG. 9B. A lens array 904 in combination with a focusing lens 905 can produce a uniform area of illumination at 906. Such a design as shown in FIG. 9B effectively captures the illumination profile at each individual lens element and overlaps the profiles with the illumination profiles from the other lens elements at plane 906. The profiles then effectively "average out" to produce uniform illumination.

Ring illumination may have desirable performance characteristics, such as beneficial performance in the pupil plane similar to that found in ring dark field. One design to achieve beneficial performance in the pupil plane employs an aperture at the illumination pupil plane to limit the desired illumination angles. Light blocked by the aperture may be lost. It is possible to use one or more axicon elements to obtain ring illumination and minimize light loss as shown in FIGS. 10A through 10E. In FIG. 10A, a lens 1001 and a single axicon produce a ring illumination profile at plane 1003. FIGS. 10B and 10C illustrate an example of a zooming dual axicon system. First axicon 1004 creates a ring illumination profile at second axicon 1005. In FIG. 10C, changing the spacing between the axicons changes the diameter of the resultant ring illumination. A similar zooming axicon system is shown in FIGS. 10D and 10E. In the system of FIGS. 10D and 10E, a diverging axicon 1006 and a converging axicon 1007 are used in combination. Again, changing the spacing between the axicons changes the diameter of the resultant ring illumination. The axial length can be shortened using such an arrangement.

Figure 11A:
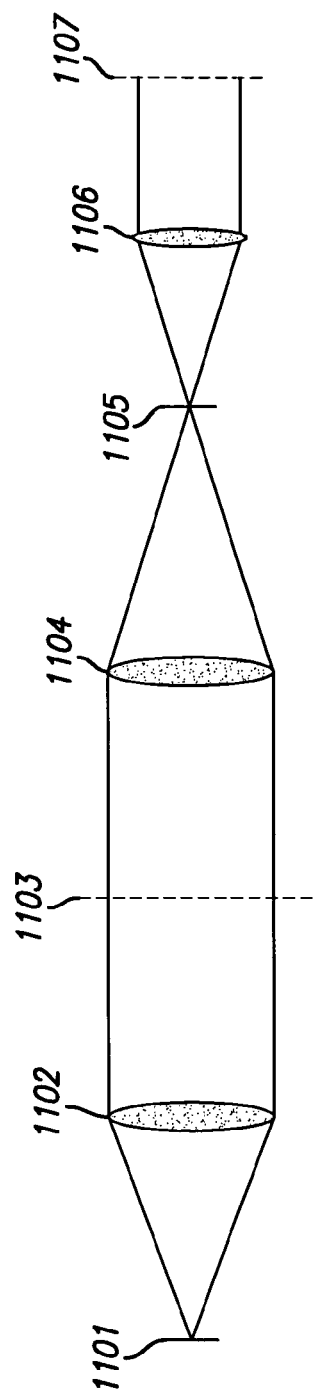
FIG. 11A illustrates field and pupil plane relay optics.
Figure 11B:
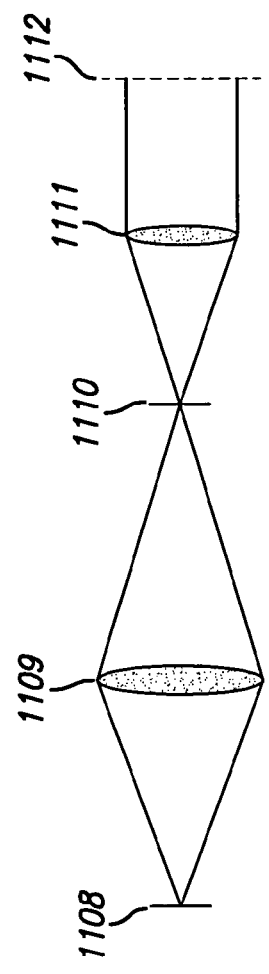
FIG. 11B shows field plane relay optics.

Other optical elements can be added within the uniformity or relay optics to control the spectrum and light level. Such optical elements may include but are not limited to absorption filters, interference filters, and reflective filters. FIGS. 11A and 11B show relay optics, used to provide an image at the field plane to a remote location with minimal distortion or optical deformation. FIG. 11A shows one example of an optical relay system using a field and pupil plane relay design that may be employed in the present system. A field plane 1101, such as the exit of a light pipe, is imaged by lenses 1102 and 1104 to an intermediate field plane 1105. An aperture can be placed at 1105 to limit the field size and reduce scattered light. An intermediate pupil plane may also be formed at 1103. Apertures can be placed at this plane to control the NA of the illumination. Various apertures can be placed at this plane to alter and/or customize the illumination. Axicon systems can also be inserted to provide ring illumination at this location. Lens 1106 is used to relay the illumination pupil 1103 to a shared pupil 1107 between the illumination and imaging paths before the field plane 1105 is imaged to the sample.

An alternate design to that shown in FIG. 11A uses no internal field relay. In this alternate design, lens 1102 relays light from field plane 1101 directly to shared pupil 1107, thus potentially reducing the number of optical components in the relay portion of the illumination system. FIG. 11B shows an alternate form of the relay optics using a field plane relay design. A field plane 1108, such as the output face of a light pipe, is imaged by lens 1109 to produce an intermediate field plane similar to 1105 in FIG. 11A. Light from this intermediate field plane is then relayed to shared pupil 1112 by lens 1111.

As noted previously, the laser illumination system consists of a laser source 131. Many varieties of lasers that can be used, including but not limited to solid state, ion, direct semiconductor, and excimer. Laser sources used in the present design are to achieve the required output power, have relatively high stability, and relatively long lifetime.

Laser power and stability are important measures for the ability to adequately inspect a specimen in accordance with the present design. The system can correct laser power variations by measuring power fluctuations with a diode and compensating for changes in signal level. Other lower power laser sources may also be employed assuming they can adequately provide the power required to image in the environment provided.

The following table presents typical wavelengths for the different laser sources that may be employed with the present system.

| Laser variety | Laser type | Wavelengths |
|---|---|---|
| Solid state | Diode pumped Yag/Ylf/YVO4 | ~1064 nm |
| | Ti sapphire | 450-650 nm |
| | Alexandrite | 720-860 nm |
| | Erbium fiber | 1550 nm |
| | Direct | Many varieties available from 400 nm->1000 nm |
| Gas | Argon | 334, 351, 363.8, 457.9, 488, 514 nm |
| | Krypton | 351, 357, 407, 415, 476, 492, 532, 568, 647 nm |
| | Excimer | 157, 193, 248, 308, 351 nm |

The system can convert the frequencies or mix these different laser wavelengths to obtain shorter wavelengths. For example, it is common to frequency double, triple and quadruple VYO4 lasers to 532, 355, and 266 nm, respectively. These lasers may operate in continuous or pulsed mode. Continuous mode allows continuous integration of light required for a scanning based data acquisition system. High repetition rate mode locked lasers are also able to be used in the present system. The repetition rate may be sufficiently faster than the signal integration time. In this arrangement, the light appears continuous to the detection system. Lasers with lower repetition rates may be used with this system, but such a laser may require a flash based system architecture as know to those skilled in the art. A flash based system architecture can be employed with excimer lasers having a maximum repetition rate of in the range of 5 kHz.

Two sample laser collection schemes that may be employed in the current system are shown in FIGS. 12A and 12B. In FIG. 12A, laser 1201 produces a Gaussian beam waist at 1202. The cavity configuration of the laser 1201 shapes the beam and thus determines the beam waist location. The beam waist may be located inside the laser itself or outside the laser 1201. For frequency converted lasers, the beam waist is often located at the frequency conversion crystal. This waist is imaged by lens 1203 to location 1204. Secondary beam waist location 1204 can be at the input to, for example, the beam uniformity optics as discussed herein. In FIG. 12B, laser 1205 emits light through an aperture 1206. This aperture can be an internal cavity aperture for defining the laser mode. The aperture can alternately be an aperture for defining the size of the laser spot. Such an aperture may be placed at the output coupler of the laser. These laser collection techniques can minimize beam pointing and centering errors from the laser.

A uniform laser source may be produced depending on the requirements and performance of the particular aspects of the system. In FIG. 13A, a lens 1301 focuses the laser onto an optic 1302 to produce a range of angles 1303. This optic 1302 can be formed of, for example, ground glass, a volume diffuser, or a diffractive optic. Diffractive optics can be more efficient than ground glass or volume diffusers, but can be expensive compared to ground glass or volume diffusers. Ground glass can be made more efficient by etching the glass with acid after the surface has been ground, and ground glass can also be manufactured to more accurately control the angular distribution exiting the diffractive optic. Typical light sources are highly coherent and the optic 1302 produces highly modulated interference or speckle patterns. Moving the optic 1302, such as rotating it relatively rapidly can average out the speckle to produce a uniform illumination pattern. FIG. 13B shows an alternate scheme where collimated input is incident on the diffuser or diffractive optic and focused down by a lens to plane 1306. Other uniform shaping optics can be placed at plane 1306, such as a light pipe. Element 1304 can also be moved or rotated to smooth any speckle patterns.

Figure 13C:
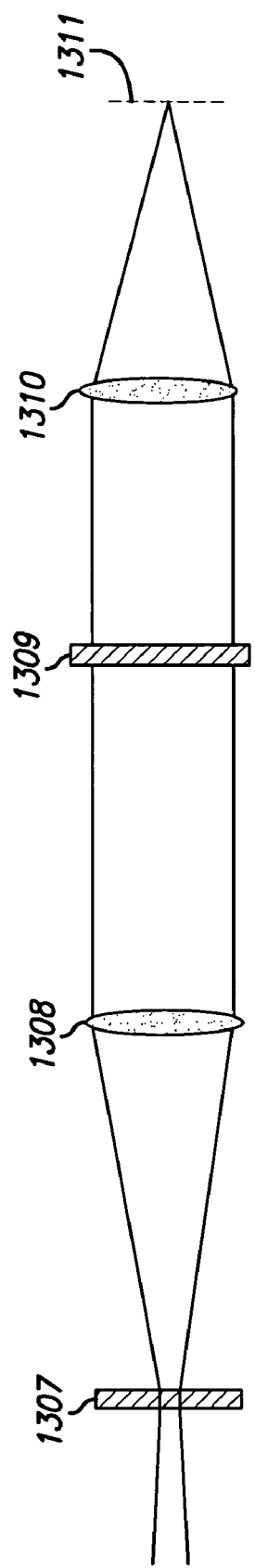
FIG. 13C is another uniform shaping scheme.

An additional uniform shaping scheme is shown in FIG. 13C. The laser is first focused through diffractive element 1307 located at an illumination field plane. Light from element 1307 is relayed by lens 1308 to diffractive element 1309 located at a pupil plane. Light from diffractive element 1309 is then relayed by lens 1310 to field plane 1311. The combination of diffractive elements at both a field plane and a pupil plane enable control of illumination profiles at both locations. Elements 1307 and 1309 can also be moved or rotated to average out interference or speckle patterns.

FIG. 13D shows relay optics that may be employed in the current system using the concept of selective pupil filling. Laser light is relayed by lens 1312 to intermediate pupil plane 1313. The system then collects light from the pupil plane and relays the light via lenses 1314 and 1316 to shared pupil plane 1317. The arrangement of the beam shaping optics determines the distribution of intensity at pupil plane 1313. Using this design, uniform illumination or near uniform illumination may be realized, as well as individual point illumination, ring illumination, quadrapole illumination, or other desirable patterns. An aperture may also be placed at intermediate field plane 1315 to minimize the effects of scattered light. FIG. 13E shows the illumination relay scheme for laser dark field outside the imaging optics. Incident laser light 1319 illuminates the sample 1320 in this arrangement. Imaging optics 1318 may collect scattered light from the specimen or sample. The laser can be oriented at different angles within the plane of incidence to more effectively collect the signal and enhance the imaging signal-to-noise ratio. Single or multiple laser illumination beams 1319 can also be employed. Four lasers may be employed, each with the same angle of incidence, separated by 90 degrees around the normal of sample 1320.

Positioning

The positioning subsystem for a DUV inspection system may provide high speed positioning of the specimen, rotation capability for alignment of the specimen, and translation along the optical axis for focusing of the specimen. A precision stage, known to those skilled in the art, may be employed to perform high speed positioning of the specimen. Stages of this type typically use air bearings on a precision surface, including but not limited to granite, to define the motion. High speed motion is most often achieved using one or more linear motors.

Various scanning options may be employed for a stage used for high speed inspection. One method to inspect patterned samples such as semiconductor wafers is the raster scan. Using raster scanning, the stage moves the sample across the imaging subsystem field of view in one direction. The stage is then incremented or stepped in the orthogonal direction and the stage moves the sample across the imaging subsystem field in the opposite direction. This stepping or incrementing repeats until the desired area of the sample is inspected. The sample may also be moved in an R-theta scan. In this technique the sample is rotated across the imaging subsystem field of view. As one rotation is complete the radius is increased until the desired area of the sample is inspected. The sample can be stepped in the radial direction or continuously moved to create a spiral inspection path, much like playing an LP record.

Rotation capability may alternately be provided on a raster scanning positioning subsystem. This allows features on the sample such as straight lines or objects oriented in rows or linear patterns to be pre-aligned with the scanning direction before the raster scanning is started. This allows the line or pattern to maintain substantially the same position on the image sensor during raster scanning.

Focusing may employ a stage having the ability to move along an axis parallel to the optical axis and orthogonal to the scanning plane. Focusing in this arrangement can be fast enough to maintain focus during a high speed scan, which can require operation at approximately 1000 Hz or higher. The resolution may be high enough to stay substantially within the depth of focus of the optical system. For high NA, short wavelength systems, the resolution is often less than 50 nm, requiring a high resolution motion system such as a PZT system known to those skilled in the art.

Imaging

The design of the imaging subsystem is based on a high numerical aperture (NA) small size catadioptric objective having a large field and accommodating a broad band light source to support a variety of imaging modes. The optical design may utilize more than one wavelength for autofocus, optics with an external pupil or Fourier plane, as well as zoom capability. Purging and contamination control of the optics may be provided, such as being oxygen free for UV light energy sources.

Figure 14:
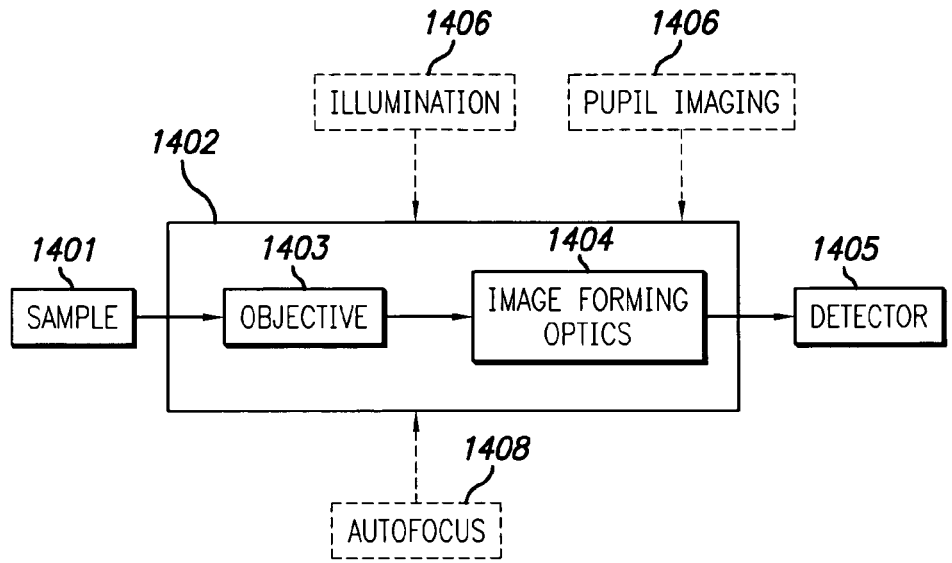
FIG. 14 shows the elements of a general imaging system.

The architecture for an imaging system is shown in FIG. 14. The imaging system 1402 consists of an objective 1403 and image forming optics 1404. The primary purpose of the imaging system 1402 is to form an image of the sample 1401 on the detector 1405. For the imaging system to operate in a microscope or inspection type environment, illumination must be as discussed above using illuminator 1406. Autofocus element 1408 may be employed to maintain image focus, and pupil imaging 1407 may be employed for alignment of system components.

Figure 15:
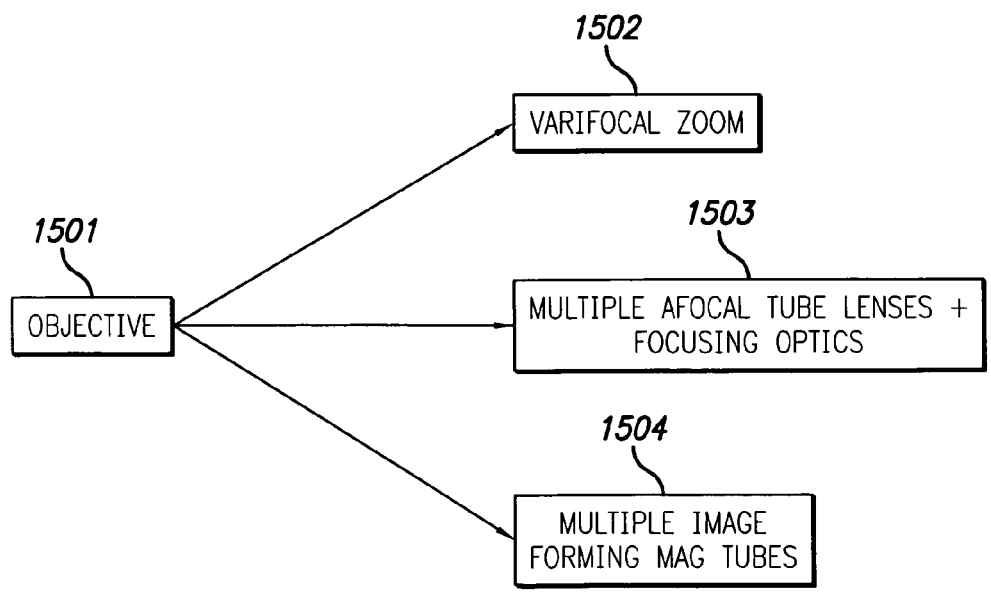
FIG. 15 shows the relationship between the objective and imaging optics that may be employed in the current design.

Imaging in the present system may entail use of various imaging schemes. From FIG. 15, the objective 1501 may be a single fixed objective, multiple fixed objectives, multiple objectives on a turret, or a combination of these approaches. Imaging optics can be implemented in several different forms including a varifocal zoom 1502, multiple afocal tube lenses with focusing optics 1503, or multiple image forming mag tubes 1504.

Figure 16:
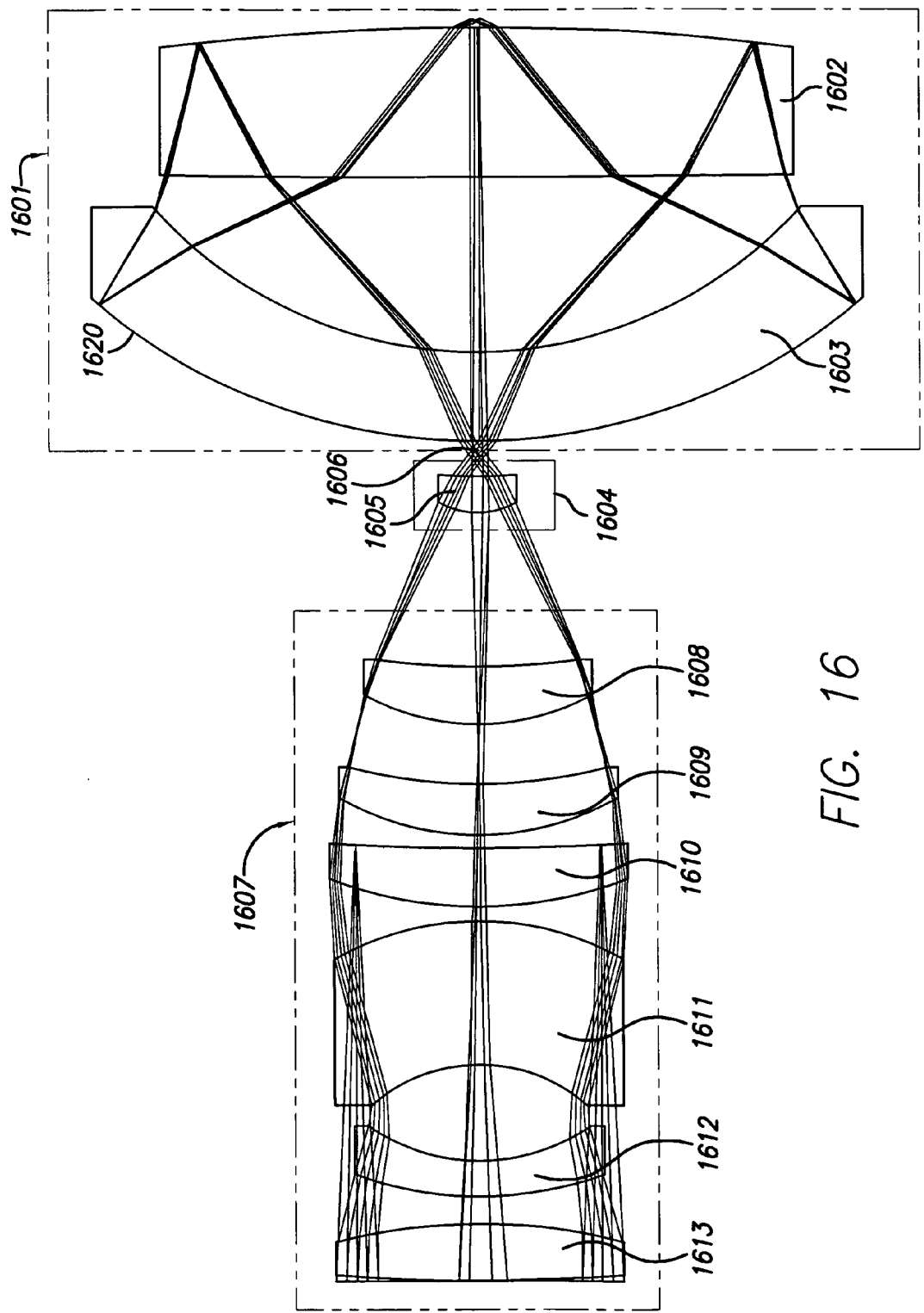
FIG. 16 shows an aspect of a small sized catadioptric objective that may be employed in the current design.

According to the present design, a catadioptric objective may be provided that is corrected over a wavelength range from 285-320 nm using a single glass material, or in certain circumstances, more than one glass material to improve performance. One aspect of the objective design is shown in FIG. 16. The catadioptric objective as shown in FIG. 16 is optimized for broad-band imaging in the UV spectral region, namely approximately 0.285 to 0.320 micron wavelengths. The objective provides relatively high numerical apertures and large object fields. The inventive design presented uses the Schupmann principle in combination with an Offner field lens to correct for axial color and first order lateral color. Special challenges-are presented when correcting various color aberrations when only one glass type is used. Conventional designs usually use two or three glass types to correct color aberrations. The present design performs the correction in the presence of a single material type used in all lenses due to the specific lens and mirror configuration. In very deep both silica and $CaF_2$ are highly dispersive, so even a narrow spectral bandwidth at very short wavelengths can require the correction of quite a few distinct color aberrations. Such color aberrations may include primary and secondary axial color, primary and secondary lateral color, chromatic variation of spherical aberration, and chromatic variation of coma. In the present,system, lens and mirror positioning permits primary axial and lateral color to be completely corrected. Secondary axial and lateral color cannot be completely corrected, but can be kept small enough to be acceptable over a relatively narrow spectral bandwidth. Chromatic variation of both spherical aberration and coma can also be corrected using this small fold mirror and dual field lens design.

As shown in the aspect presented in FIG. 16, the field lens group 1605 is slightly displaced from the intermediate image 1606 to obtain enhanced performance.

From FIG. 16, the catadioptric group 1601 or Mangin mirror,arrangement includes a Mangin mirror element 1602. Mangin mirror element 1602 is a reflectively coated lens element. The catadioptric group 1601 also includes and a concave spherical reflector 1603, also a reflectively coated lens element. Both elements in the catadioptric group 1601 have central optical apertures where reflective material is absent, enabling light to pass from the object or specimen 1600 (not shown) through Mangin mirror element 1602, reflect from the second or inner surface of concave spherical reflector 1603, onto the reflective surface 1620 of Mangin mirror element 1602, and through concave spherical reflector 1603 to form an intermediate image 1606 between concave spherical reflector 1603 and field lens group 1604. The field lens group 1604 may comprise one or more lenses, and in the aspect shown in FIG. 16, one field lens is employed in the field lens group 1604.

The focusing lens group 1607 uses multiple lens elements, in the aspect shown six lens elements 1608, 1609, 1610, 1611, 1612, and 1613. All lenses in the focusing lens group 1607 may be formed from a single type of material to collect the light from the field lens group 1604 and the intermediate image 1606.

The lens prescription for the aspect of the design illustrated in FIG. 16 is presented in Table 1.

TABLE 1

Prescription for lenses for the design of FIG. 16

| Surface Number | Radius | Thickness | Glass | Diameter |
|---|---|---|---|---|
| OBJ | Infinity | Infinity | | 0 |
| 1 | Infinity | 15.50165 | | 9.39467 |
| STO | Infinity | −15.50165 | | 8 |
| 3 | 53.51878 | 2 | Fused Silica | 9.376161 |
| 4 | −18.17343 | 0.976177 | | 9.234857 |
| 5 | 10.48757 | 1.249953 | Fused Silica | 8.151456 |
| 6 | 5.891816 | 3.328088 | | 7.199539 |
| 7 | −5.254784 | 5.105439 | Fused Silica | 7.084075 |
| 8 | −8.860388 | 0.5 | | 9.430437 |
| 9 | 12.82516 | 2 | Fused Silica | 9.711337 |
| 10 | 61.04848 | 0.5 | | 9.468601 |
| 11 | 8.892555 | 1.75 | Fused Silica | 9.125279 |
| 12 | 15.75614 | 2.126452 | | 8.563035 |
| 13 | 7.216376 | 2 | Fused Silica | 7.4431 |
| 14 | 21.90145 | 5.382485 | | 6.702302 |
| 15 | 2.321495 | 1.3 | Fused Silica | 2.530266 |
| 16 | 13.47255 | 0.669203 | | 1.651874 |
| 17 | Infinity | 0.498865 | | 0.711891 |
| 18 | 17.99728 | 3.170995 | Fused Silica | 25 |
| 19 | 13.41607 | 6.08537 | | 21 |
| 20 | 972.9414 | 5.220004 | Fused Silica | 20.5 |
| 21 | −78 | −5.220004 | MIRROR | 20.5 |
| 22 | 972.9414 | −6.08537 | | 20.5 |
| 23 | 13.41607 | −3.170995 | Fused Silica | 21 |
| 24 | 17.99728 | 3.170995 | MIRROR | 25 |
| 25 | 13.41607 | 6.08537 | | 21 |
| 26 | 972.9414 | 5.220004 | Fused Silica | 20.5 |
| 27 | −78 | 0.3 | | 20.5 |
| IMA | Infinity | | | 0.410191 |

As may be appreciated by one skilled in the art, the numbers in the leftmost column of Table 1 represent the surface number counting surfaces from the left of FIG. 16. For example, the left surface of lens 1612 in the orientation presented in FIG. 16 (surface 3 in Table 1) has a radius of curvature of 53.51878 mm and a thickness of 2 mm. The rightmost surface (surface 4) of the lens 1612 has a radius of curvature of −18.17343 mm and is 0.976177 mm from the next surface. The material used is fused silica, and the diameter of the left surface is 9.376161 mm and of the right surface is 9.234857 mm.

The high NA catadioptric objective illustrated may be used and optimized for light beams having different wavelengths, from the infrared to the deep ultraviolet. For example, in the ultraviolet spectrum, light beams having wavelengths of approximately 193 nm, 213 nm, 244 nm, 248 nm, 257 nm, 266 nm, and so forth are possible using the concepts disclosed herein, with adjustments that would be apparent to those of ordinary skill in the art. For wavelengths from approximately 110-200 nm, fluoride glasses may be used.

In the design presented in FIG. 16, the numerical aperture may approach or even exceed approximately 0.90. The design presented herein, including the aspect illustrated in FIG. 16, provides a maximum numerical aperture in all cases in excess of 0.65.

From FIG. 16, the focusing lens group 1607 has the ability to receive light energy and transmit focused light energy. The field lens group 1604 has the ability to receive the focused light energy and provide intermediate light energy and form intermediate image 1606. The catadioptric group or Mangin mirror arrangement 1601 receives the intermediate energy and provides controlled light energy to the specimen. Alternately, the reflected path originates at the specimen, and light reflected from the specimen is received by the catadioptric group or Mangin mirror arrangement 1601 and forms and transmits reflected light energy. The field lens group 1604 receives the reflected light energy and transmitting resultant light energy, and the focusing lens group receives resultant light energy and transmits focused resultant light energy.

The design presented in FIG. 16 and Table 1 thus uses a single glass material, fused silica. Other materials may be employed, but it is noted that fused silica or any material used within the design may require low absorption over a wide range of wavelengths from 190 nm through the infrared wavelength. Use of fused silica can enable the design to be re-optimized for any center wavelength in this wavelength range. For example, the design can be optimized for use with lasers at 193, 198.5, 213, 244, 248, 257, 266, 308, 325, 351, 355, or 364 nm. The design can also be optimally employed to cover lamp spectral bands from 192-194, 210-216, 230-254, 285-320, and 365-546 nm. In addition, if calcium fluoride is employed as the glass or lens material, the design can be employed with an excimer laser at 157 nm or excimer lamps at 157 or 177 nm. Re-optimization requires tuning or altering components within the abilities of those skilled-in the art. Calcium fluoride lenses may also be employed in the field lens group to increase the bandwidth of the objective, a modification discussed generally in U.S. Pat. No. 5,717,518.

As noted in FIG. 16, the objective has a diameter of 26 millimeters, which is significantly smaller than objectives previously employed in this wavelength range. The small size of this objective is particularly beneficial in view of the performance characteristics of the objective. The objective can be mounted in a standard microscope turret with a 45 mm flange-to-object separation. The objective supports a numerical aperture of approximately 0.90, a field size of approximately 0.4 mm, has a corrected bandwidth from approximately 285-313 nm, and a polychromatic wavefront error of less than approximately 0.038 waves.

Certain tradeoffs may be made to improve performance characteristics depending on the desired application of the objective or optical design. It is possible, for example, to sacrifice bandwidth, field size, numerical aperture, and/or objective size to enhance one of the aforementioned performance characteristics, depending on the application. For example, optimizing for lower or higher NAs is possible. Reducing the NA can reduce the manufacturing tolerance and the outer diameter of the objective. Lower NA designs can provide larger field sizes and larger bandwidths. Lower NA designs with the same performance and less optical elements are also possible, as is optimizing for higher NAs. Optimizing the design for higher NAs can limit the field size or bandwidth and may in certain circumstances require slightly increased diameter objective elements.

The design of FIG. 16 has a field size of approximately 0.4 mm in diameter. Such a relatively large field size can support a large high speed sensor. For example, using an imaging magnification of 200×, a sensor having an 80 mm diagonal can be supported and provide adequate performance in the environment shown. The design of FIG. 16 can also be extended to larger field sizes by using larger lens diameters and re-optimizing the elements, again a task within the range of those skilled in the art.

The design of FIG. 16 has a relatively low intrinsic polychromatic wavefront aberration over the design bandwidth from approximately 285-320 nm. The low wavefront aberration provides increased manufacturing headroom, or ease of manufacture, while enabling relatively high performance of the manufactured objective. The design of FIG. 16 provides good performance over narrow bands from approximately 266 to 365 nm if the objective is refocused, again a task that may be readily performed by one of ordinary skill in the art. Use of the objective of FIG. 16 in this narrow band range allows use of lasers or narrow lamp spectra, such as the 365 nm line of lasers. The design is also self corrected. Self corrected in this context means that the objective does not require any additional optical components to correct aberrations in order to achieve the design specifications. Self correction capability can simplify optical testing metrology and optical alignment to other self corrected imaging optics. The system may further correct residual aberrations using additional imaging optics (not shown). Use of additional optics with further corrected residual aberrations can enhance optical specifications such as increasing the bandwidth or field size.

The present design, including the aspect shown in FIG. 16, has relatively loose manufacturing tolerances. Specifically, the decenter tolerances of individual lenses are relatively loose. Having loose decenter tolerances for individual lens elements tends to simplify the manufacturing requirements of the system. Any lens decenters encountered during manufacturing may cause on-axis coma, a phenomenon that can be difficult to compensate without introducing other residual aberrations. Using the present design, such as the aspect shown in FIG. 16, decenter sensitivity of the lens and mirror elements may be reduced by carefully balancing the aberrations within the catadioptric group 1601 and focusing lens group 1607. Total aberrations of the catadioptric group may be optimized using the design of FIG. 16 to balance the compensation required by the field lens group 1604 and focusing lens group 1607. In the design presented in FIG. 16, average tolerance is approximately 0.13 waves of error at approximately 313 nm. Further balancing the tolerances on the elements in the catadioptric group 1601 is also possible. The decenter tolerances also scale with the wavelength being used, as the optical path errors introduced for small decenters are not a strong function of wavelength. For example, if a 10 micron decenter introduces 0.2 waves of aberration at a 266 nm wavelength, such an aberration is equivalent to a 0.0532 micron optical path error. The system operating at 365 nm would only introduce approximately 0.15 waves of aberration for the same decenter, which would have a similar 0.0532 micron optical path error.

These tolerances tend to be looser than other catadioptric designs in similar environments, and tend to be looser than most standard refractive objective designs. The present design, including the design of FIG. 16, has relatively loose tolerances for glass material index. Loose tolerances result from the single material construction. Use of a single material does not rely on the index difference of two different glass materials to compensate for chromatic aberrations. Use of a single material also makes the design relatively very insensitive to temperature changes. Standard designs use multiple glass materials and can require different index profiles for color correction, as the index profile for each material changes differently with temperature. Use of a single material enhances performance by obviating the need to compensate for temperature changes and reduces the need for chromatic correction.

Figure 17:
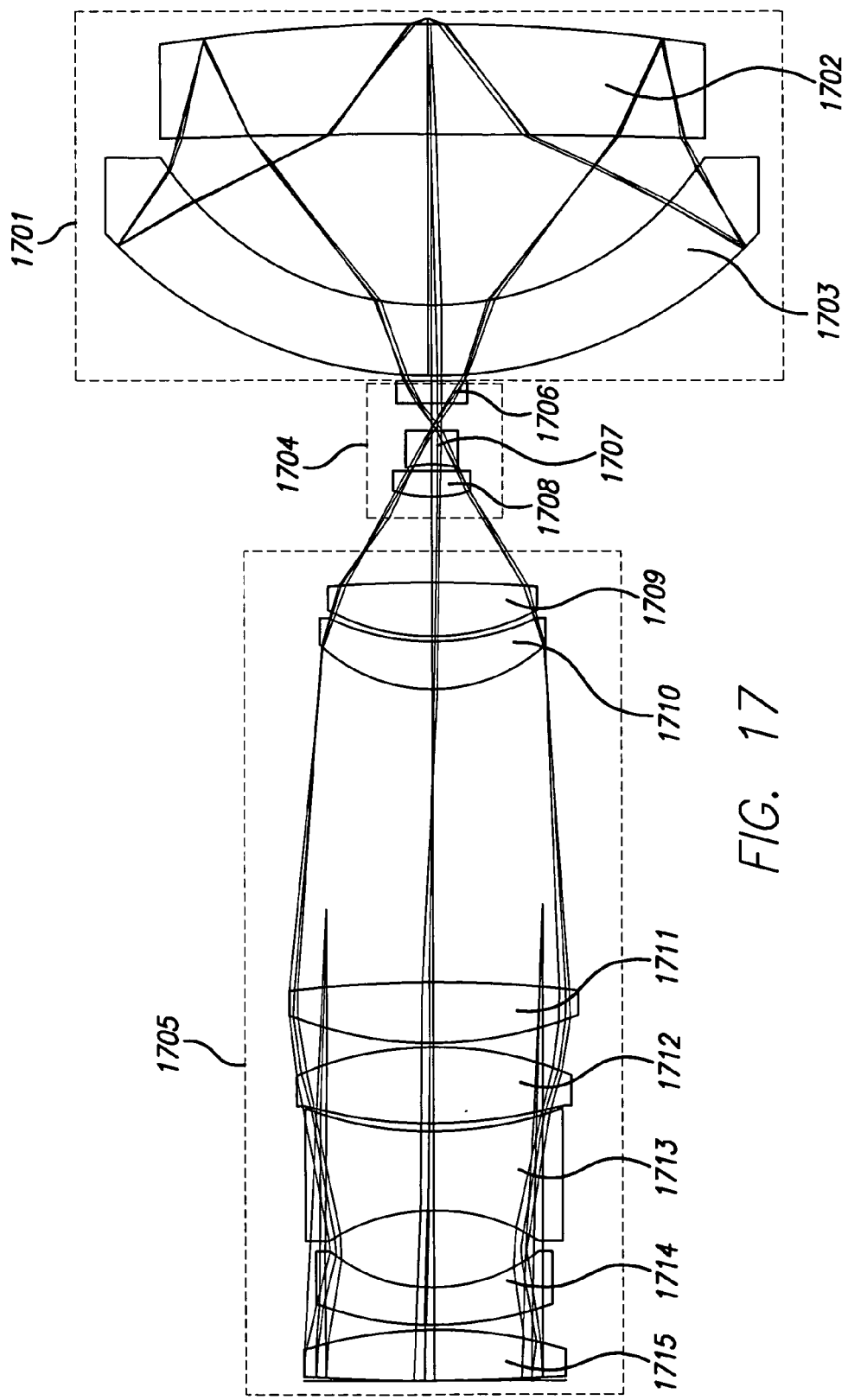
FIG. 17 shows a small sized objective corrected for a bandwidth of approximately 285 to 320 nm.

An alternate aspect of the current design is an objective having increased field size. This aspect of the design is presented in FIG. 17. The main difference between the design of FIG. 17 and that of FIG. 16 is the increased field size from approximately 0.4 mm to approximately 1.0 mm, in addition to an increase in lens diameter from approximately 25 mm to approximately 58 mm. In contrast to prior catadioptric designs, the maximum lens diameter is significantly smaller. The objective of the design of FIG. 17 is generally corrected over a bandwidth from approximately 285 to 320 nm. The design of FIG. 17 maintains the high 0.90 numerical aperture. The worst case polychromatic wavefront error for the FIG. 17 design is approximately 0.033 waves.

From FIG. 17, the catadioptric group 1701 includes a Mangin mirror element 1702, which is a reflectively coated lens element, and a concave spherical reflector 1703, which is also a reflectively coated lens element. Both Mangin mirror element 1702 and concave spherical reflector 1703 have central optical apertures where reflective material is absent. The absence of reflective material, in the center of the components shown, allows light to pass from the object or specimen 1700 (not shown) through Mangin mirror element 1702, reflect from the second surface of concave spherical reflector 1703 onto the Mangin mirror element 2, and transmit through concave spherical reflector 3 to form an intermediate image 1720 within field lens group 1704, comptising three field lens elements in this aspect of the design.

The focusing lens group 1705 employs multiple lens elements, in this aspect the seven lens elements 1706, 1707, 1708, 1709, 1710, and 1711, 1712, which may all be formed from a single type of material. The focusing lens group 1705 collects light from the field lens group 1704, including the intermediate image 1720.

The lens prescription for this embodiment is shown in Table 5.

TABLE 5

Prescription for lenses for the design of FIG. 17

| Surf | Radius | Thickness | Glass | Diameter |
|---|---|---|---|---|
| OBJ | Infinity | Infinity | | 0.000 |
| 1 | Infinity | 43.913 | | 23.946 |
| STO | Infinity | −43.913 | | 20.000 |
| 3 | 349.851 | 4.500 | Fused silica | 23.928 |
| 4 | −43.383 | 0.500 | | 23.709 |
| 5 | 30.361 | 3.650 | Fused silica | 21.950 |
| 6 | 16.181 | 7.177 | | 19.386 |
| 7 | −17.138 | 7.305 | Fused silica | 19.277 |
| 8 | 32.672 | 0.872 | | 23.722 |
| 9 | 47.511 | 7.000 | Fused silica | 23.916 |
| 10 | −30.308 | 0.500 | | 25.201 |
| 11 | 37.466 | 5.500 | Fused silica | 26.737 |
| 12 | −147.458 | 27.319 | | 26.555 |
| 13 | 14.910 | 4.500 | Fused silica | 21.011 |
| 14 | 22.738 | 0.500 | | 19.515 |
| 15 | 20.121 | 5.000 | Fused silica | 19.161 |
| 16 | −127.415 | 7.984 | | 17.640 |
| 17 | 12.578 | 2.500 | Fused silica | 7.187 |
| 18 | −46.414 | 0.500 | | 5.333 |
| 19 | −12.279 | 3.131 | Fused silica | 4.668 |
| 20 | −15.865 | 2.594 | | 1.955 |
| 21 | −576.001 | 2.250 | Fused silica | 4.516 |
| 22 | −20.181 | 0.250 | | 6.277 |
| 23 | 40.385 | 6.603 | Fused silica | 60.000 |
| 24 | 29.574 | 15.917 | | 50.000 |
| 25 | −777.423 | 10.056 | Fused silica | 50.000 |
| 26 | −202.605 | −10.056 | MIRROR | 50.000 |

TABLE 5-continued

Prescription for lenses for the design of FIG. 17

| Surf | Radius | Thickness | Glass | Diameter |
|---|---|---|---|---|
| 27 | −777.423 | −15.917 | | 50.000 |
| 28 | 29.574 | −6.603 | Fused silica | 50.000 |
| 29 | 40.385 | 6.603 | MIRROR | 60.000 |
| 30 | 29.574 | 15.917 | | 50.000 |
| 31 | −777.423 | 10.056 | Fused silica | 50.000 |
| 32 | −202.605 | 0.750 | | 50.000 |
| IMA | Infinity | | | 1.005 |

An additional aspect of the present design uses a tube lens to correct for residual aberrations in the objective. Correcting these residual aberrations can increase the field size or increase the bandwidth while maintaining the field size. Residual aberrations are primarily the chromatic variation of distortion and higher order lateral color. The design of FIG. 8 maintains the same approximately 0.4 mm field size as in the design of FIG. 16 and extends the bandwidth to cover approximately 266 to 405 nm without need for refocusing. The worst case polychromatic wavefront error for the design of FIG. 18 is approximately 0.041 waves.

Figure 18:
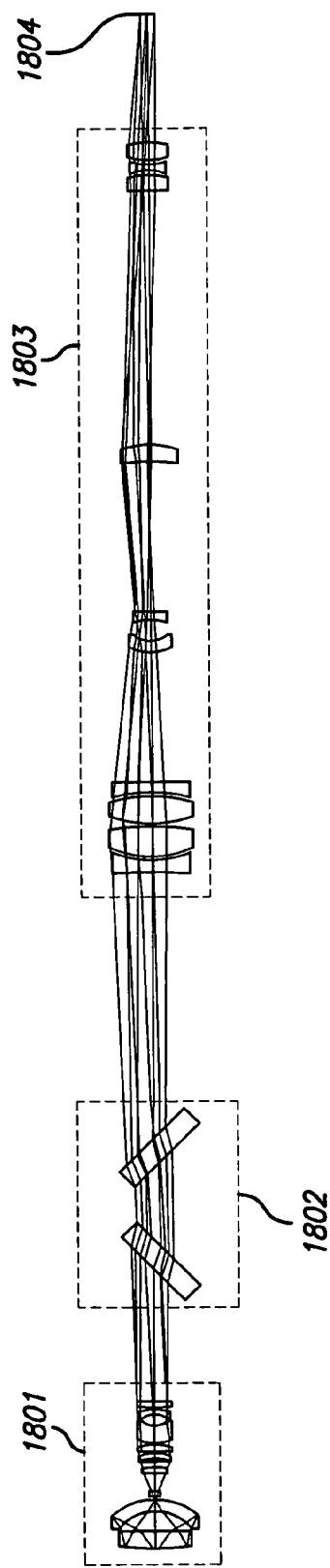
FIG. 18 is a tube lens arrangement.

The design in FIG. 18 is composed of an objective 1801 that collects the light and a tube lens 1803 that corrects residual aberations. To achieve the additional bandwidth beyond the design of FIG. 16, the objective and tube lens are partially optimized together. This allows further correction of the limiting off axis lateral color and chromatic variation of distortion. The tube lens forms an external pupil 1804 that can be used in the same fashion as the design of FIG. 16. This design also shows optional beamsplitter elements 1802 that can be used to fold in illumination and autofocus light. The lens prescription for the aspect illustrated in FIG. 18 is shown in Table 4.

TABLE 4

Prescription for lenses for the design of FIG. 18

| Surf | Radius | Thickness | Glass | Diameter |
|---|---|---|---|---|
| OBJ | Infinity | 0.300 | | 0.4 |
| 1 | 78.000 | 5.168 | Fused silica | 21 |
| 2 | −850.121 | 6.031 | | 21 |
| 3 | −13.361 | 3.505 | Fused silica | 21.5 |
| 4 | −18.352 | −3.505 | MIRROR | 25.5 |
| 5 | −13.361 | −6.031 | | 21.5 |
| 6 | −850.121 | −5.168 | Fused silica | 21 |
| 7 | 78.000 | 5.168 | MIRROR | 21 |
| 8 | −850.121 | 6.031 | | 21 |
| 9 | −13.361 | 3.505 | Fused silica | 21.5 |
| 10 | −18.352 | 0.599 | | 25.5 |
| 11 | Infinity | 0.598 | | 0.8876633 |
| 12 | −22.089 | 1.498 | Fused silica | 1.735372 |
| 13 | −2.492 | 5.525 | | 2.742536 |
| 14 | −25.242 | 1.750 | Fused silica | 6.958087 |
| 15 | −8.752 | 1.574 | | 7.613493 |
| STO | Infinity | 1.011 | | 8.782304 |
| 17 | −26.420 | 1.750 | Fused silica | 9.130406 |
| 18 | −10.453 | 0.500 | | 9.615398 |
| 19 | 214.479 | 2.000 | Fused silica | 10.09149 |
| 20 | −12.858 | 0.500 | | 10.245 |
| 21 | 10.710 | 5.074 | Fused silica | 9.775169 |
| 22 | 5.729 | 3.622 | | 7.468521 |
| 23 | −6.365 | 1.499 | Fused silica | 7.601525 |
| 24 | −11.721 | 0.499 | | 8.660195 |
| 25 | 20.390 | 2.000 | Fused silica | 9.505927 |
| 26 | −47.176 | −15.391 | | 9.654623 |
| 27 | Infinity | 15.391 | | 8.373404 |
| 28 | Infinity | 40.197 | | 9.675574 |
| 29 | — | 0.000 | | — |

TABLE 4-continued

Prescription for lenses for the design of FIG. 18

| Surf | Radius | Thickness | Glass | Diameter |
|---|---|---|---|---|
| 30 | Infinity | 6.000 | Fused silica | 19.30992 |
| 31 | Infinity | 0.000 | | 26.25127 |
| 32 | — | 0.000 | | — |
| 33 | Infinity | 30.000 | | 17.76485 |
| 34 | — | 0.000 | | — |
| 35 | Infinity | 6.000 | Fused silica | 27.58405 |
| 36 | Infinity | 0.000 | | 21.36646 |
| 37 | — | 0.000 | | — |
| 38 | Infinity | 81.000 | | 15.75755 |
| 39 | −140.860 | 4.000 | Fused silica | 22.67915 |
| 40 | 35.044 | 1.068 | | 23.39086 |
| 41 | 31.623 | 9.000 | CAF2 | 24.17115 |
| 42 | −71.279 | 1.000 | | 24.64826 |
| 43 | 34.991 | 8.000 | CAF2 | 24.5185 |
| 44 | −50.752 | 1.500 | | 23.4315 |
| 45 | −37.766 | 3.000 | Fused silica | 22.75917 |
| 46 | 331.537 | 39.138 | | 21.89289 |
| 47 | 11.729 | 3.402 | Fused silica | 12.61895 |
| 48 | 9.275 | 6.254 | | 10.82904 |
| 49 | −22.713 | 2.500 | Fused silica | 10.19172 |
| 50 | 149.521 | 45.554 | | 10.31249 |
| 51 | −142.117 | 5.000 | Fused silica | 16.06325 |
| 52 | −25.943 | 76.816 | | 16.73351 |
| 53 | −369.224 | 5.000 | CAF2 | 11.62667 |
| 54 | −14.234 | 1.000 | | 11.50051 |
| 55 | −12.790 | 2.000 | Fused silica | 11.04605 |
| 56 | 20.324 | 1.000 | | 11.08561 |
| 57 | 18.583 | 5.500 | CAF2 | 11.41199 |
| 58 | −32.851 | 38.519 | | 11.39769 |
| 59 | — | 100.000 | | 5.11369 |
| IMA | Infinity | | | 16.29315 |

The design spectrum in this aspect can be limited to approximately 266-365 nm and can be reoptimized for a 0.5 mm field size. The tube lens design of FIG. 18 also uses only fused silica and calcium fluoride and has similar flexibility for reoptimizing as the aspect presented in FIG. 16.

The maximum numerical apertures of the current embodiments approach or exceed 0.9. Numerical aperture can be reduced by placing a variable aperture at the aperture stop of the objective. Such an aperture stop can limit the illumination and imaging light angles. Illumination and imaging angles may be controlled independently in the present design. The imaging numerical aperture may be independently controlled by placing apertures at an external pupil plane using imaging optics such as in the designs in FIG. 16 or FIG. 18. The numerical aperture of the illumination may be reduced by underfilling the objective aperture with the illumination light, thereby allowing the full imaging NA to be used.

An additional aspect of the present design uses a tube lens to correct for residual aberrations in the 1 mm field objective. Correcting these residual aberrations can increase the field size or increase the bandwidth while maintaining the field size similar to the aspect of FIG. 18. Residual aberrations are primarily the chromatic variation of distortion and higher order lateral color. The design of FIG. 19 maintains the same approximately 1.0 mm field size as in the design of FIG. 17 and extends the bandwidth to cover approximately 266 to 405 nm without need for refocusing. The worst case polychromatic wavefront error for the design of FIG. 19 is approximately 0.040 waves.

Figure 19:
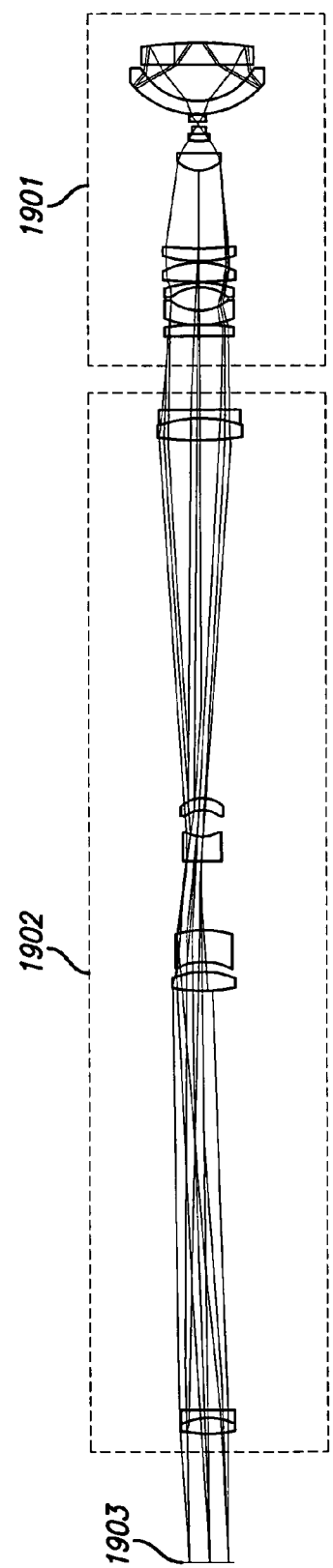
FIG. 19 illustrates a small sized objective that collects light and a tube lens that corrects residual aberrations.

The design in FIG. 19 is composed of an objective 1901 that collects the light and a tube lens 1902 that corrects residual aberrations. To achieve the additional bandwidth beyond the design of FIG. 17, the objective and tube lens may be partially optimized together, meaning the lens prescriptions and components used for both the objective and tube lens are done together to achieve additional bandwidth performance. Such a combined optimization allows further correction of the limiting off axis lateral color and chromatic variation of distortion. The tube lens forms an external pupil 1903 that can be used in generally the same manner as the design of FIG. 18. The lens prescription for the aspect of the invention illustrated in FIG. 19 is shown in Table 4.

TABLE 4

Prescription for lenses for the design of FIG. 19

| Surf | Radius | Thickness | Glass | Diameter |
|---|---|---|---|---|
| OBJ | Infinity | Infinity | | 0.000 |
| STO | Infinity | 0.000 | | 16.000 |
| 2 | Infinity | 50.000 | | 16.000 |
| 3 | 59.857 | 6.000 | Calcium fluoride | 21.716 |
| 4 | −23.863 | 0.500 | | 21.625 |
| 5 | −23.377 | 3.000 | Fused silica | 21.329 |
| 6 | 283.492 | 166.142 | | 21.261 |
| 7 | 61.981 | 7.000 | Fused silica | 24.816 |
| 8 | −33.089 | 4.403 | | 24.401 |
| 9 | −24.164 | 12.000 | Fused silica | 21.717 |
| 10 | −40.931 | 27.388 | | 21.160 |
| 11 | 43.216 | 10.000 | Fused silica | 14.683 |
| 12 | 13.257 | 10.294 | | 12.659 |
| 13 | −11.634 | 5.000 | Fused silica | 14.262 |
| 14 | −12.143 | 140.226 | | 16.856 |
| 15 | 54.669 | 10.000 | Calcium fluoride | 32.849 |
| 16 | −40.030 | 0.500 | | 32.362 |
| 17 | −39.859 | 3.000 | Fused silica | 31.999 |
| 18 | Infinity | 28.325 | | 31.362 |
| 19 | 275.989 | 4.500 | Fused silica | 27.090 |
| 20 | −138.288 | 0.500 | | 26.623 |
| 21 | 34.287 | 4.690 | Fused silica | 25.561 |
| 22 | 16.174 | 9.525 | | 22.484 |
| 23 | −18.929 | 2.535 | Fused silica | 22.741 |
| 24 | −38.099 | 0.500 | | 25.258 |
| 25 | 190.999 | 7.000 | Fused silica | 26.996 |
| 26 | −28.766 | 0.500 | | 27.917 |
| 27 | 41.645 | 5.000 | Fused silica | 27.580 |
| 28 | 133.754 | 30.149 | | 26.717 |
| 29 | 11.188 | 7.000 | Fused silica | 17.366 |
| 30 | Infinity | 5.122 | | 14.987 |
| 31 | 11.922 | 3.000 | Fused silica | 7.312 |
| 32 | −78.173 | 0.500 | | 4.981 |
| 33 | −11.373 | 2.000 | Fused silica | 4.487 |
| 34 | −17.169 | 2.740 | | 2.966 |
| 35 | 264.600 | 2.000 | Fused silica | 4.286 |
| 36 | −13.059 | 0.500 | | 5.933 |
| 37 | 34.529 | 4.881 | Fused silica | 7.289 |
| 38 | 25.399 | 14.657 | | 10.977 |
| 39 | −450.015 | 8.176 | Fused silica | 33.022 |
| 40 | −169.951 | −8.176 | MIRROR | 40.078 |
| 41 | −450.015 | −14.657 | | 43.347 |
| 42 | 25.399 | −4.881 | Fused silica | 44.232 |
| 43 | 34.529 | 4.881 | MIRROR | 52.248 |
| 44 | 25.399 | 14.657 | | 40.442 |
| 45 | −450.015 | 8.176 | Fused silica | 17.005 |
| 46 | −169.951 | 0.750 | | 4.459 |
| IMA | Infinity | | | 1.010 |

The design spectrum for the design of FIG. 19 can be limited to 266-365 nm and reoptimized for a 0.5 mm field size. The tube lens design of FIG. 19 also uses only fused silica and calcium fluoride and flexibility for reoptimizing similar,to that presented for the design of FIG. 18.

Again, the maximum numerical apertures of the current embodiments approach or exceed 0.9. The numerical aperture of a design can be reduced by placing a variable aperture at the aperture stop of the objective, effectively limiting the illumination and imaging light angles. Again, independent control over the illumination and imaging angles is possible in the FIG. 18 or FIG. 19 design. The imaging numerical aperture may be independently controlled by placing apertures at an external pupil plane using imaging optics such as the tube lens designs in FIG. 18 or FIG. 19. The numerical aperture of the illumination may be reduced by underfilling the objective aperture with the illumination light, enabling the full imaging NA to be used.

Tube lenses similar to those shown in FIGS. 18 and 19 can directly form images on a detector. Such a design reduces the number of optical elements or lenses required, can increase the overall light transmission and reduce complexity. Use of an afocal lens in such a design provides an external pupil where apertures or Fourier filters may be positioned. Additional optics may be required to form an adequate image on a detector, such as fixed image forming optics, optics with limited zoom capability, or varifocal optics.

Figure 24:
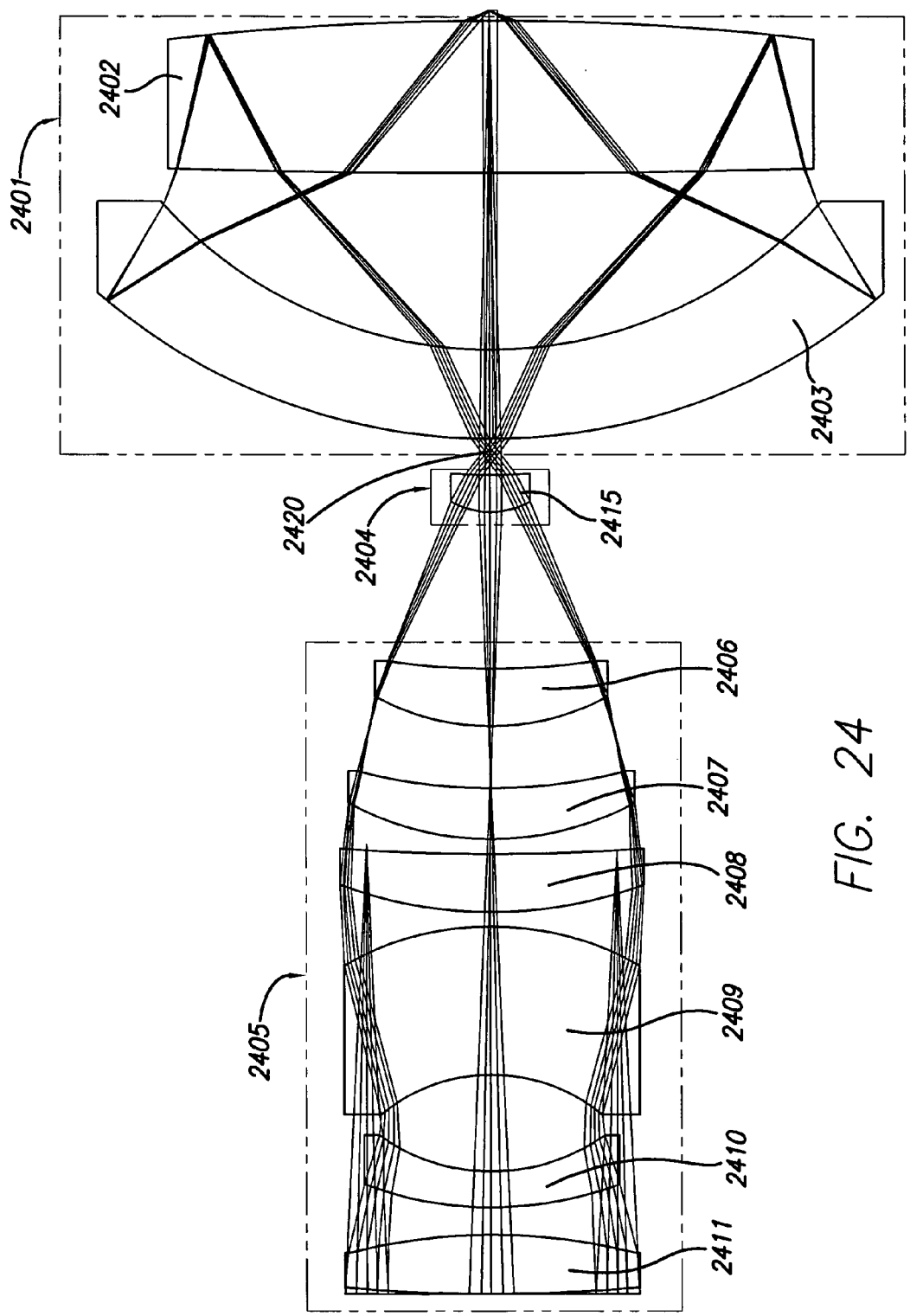
FIG. 24 is an alternate aspect of the reduced size catadioptric objective in accordance with the present invention.

An alternate aspect of the present design presents an objective with increased bandwidth. This aspect of the design is presented in FIG. 24. The main difference between the design of FIG. 24 and that of FIG. 16 is the tradeoff between bandwidth and field size. The objective of the design of FIG. 24 is corrected over a broader bandwidth from 266 to 320 nm but has a relatively smaller field, approximately 0.28 mm, as compared with the 0.4 mm of the design of FIG. 16. The design of FIG. 24 maintains the high approximately 0.90 numerical aperture. The worst case polychromatic wavefront error for the FIG. 24 design is approximately 0.036 waves.

From FIG. 24, the catadioptric group 2401 includes a Mangin mirror element 2402, which is a reflectively coated lens element, and a concave spherical reflector 2403, which is also a reflectively coated lens element. Both Mangin mirror element 2402 and concave spherical reflector 2403 have central optical apertures where reflective material is absent. The absence of reflective material, in the center of the components shown, allows light to pass from the object or specimen 2400 (not shown) through Mangin mirror element 2402, reflect from the second surface of concave spherical reflector 2403 onto the Mangin mirror element 2402, and transmit through concave spherical reflector 2403 to form an intermediate image 2420 between concave spherical reflector 2403 and field lens group 2404, comprising a single field lens 2415 in this aspect of the design.

The focusing lens group 2405 employs multiple lens elements, in this aspect the six lens elements 2406, 2407, 2408, 2409, 2410, and 2411, which may all be formed from a single type of material. The focusing lens group 2405 collects light from the field lens group 2404, including the intermediate image 2420. The lens prescription for this embodiment is shown in Table 5.

TABLE 5

Prescription for lenses for the design of FIG. 24

| Surf | Radius | Thickness | Glass | Diameter |
|---|---|---|---|---|
| OBJ | Infinity | Infinity | | 0 |
| 1 | Infinity | 16.20723 | | 9.020484 |
| STO | Infinity | −16.20723 | | 8 |
| 3 | 64.63011 | 2 | FUSED SILICA | 9.010584 |
| 4 | −19.00905 | 1.675169 | | 8.894847 |
| 5 | 10.3536 | 1.249991 | FUSED SILICA | 7.776084 |
| 6 | 5.91317 | 3.249904 | | 6.942948 |
| 7 | −5.240171 | 5.243182 | FUSED SILICA | 6.855225 |
| 8 | −9.11876 | 0.5 | | 9.288367 |
| 9 | 16.20784 | 2 | FUSED SILICA | 9.638653 |
| 10 | Infinity | 0.5 | | 9.499901 |
| 11 | 8.951438 | 3.573584 | FUSED SILICA | 9.210718 |
| 12 | 12.83071 | 0.5 | | 7.808034 |

TABLE 5-continued

Prescription for lenses for the design of FIG. 24

| Surf | Radius | Thickness | Glass | Diameter |
|---|---|---|---|---|
| 13 | 7.107306 | 2 | FUSED SILICA | 7.502914 |
| 14 | 29.37779 | 5.583862 | | 6.837774 |
| 15 | 2.252897 | 1.3 | FUSED SILICA | 2.391106 |
| 16 | 11.8636 | 0.668164 | | 1.486574 |
| 17 | Infinity | 0.499742 | | 0.548495 |
| 18 | 17.95894 | 3.09472 | FUSED SILICA | 25 |
| 19 | 13.41421 | 6.156826 | | 21 |
| 20 | 1134 | 5.204856 | FUSED SILICA | 20.5 |
| 21 | −78 | −5.204856 | MIRROR | 20.5 |
| 22 | 1134 | −6.156826 | | 20.5 |
| 23 | 13.41421 | −3.09472 | FUSED SILICA | 21 |
| 24 | 17.95894 | 3.09472 | MIRROR | 25 |
| 25 | 13.41421 | 6.156826 | | 21 |
| 26 | 1134 | 5.204856 | FUSED SILICA | 20.5 |
| 27 | −78 | 0.3 | | 20.5 |
| IMA | Infinity | | | 0.289101 |

A further aspect of the present design uses a tube lens to correct for residual aberrations in the objective. Residual aberrations are primarily the chromatic variation of distortion and higher order lateral color. These residual aberrations are related to use of the Offner field lens in the objective. One method to correct these residual aberrations is to employ a second glass material in the Offner field lens. Use of a second material can lead to an optical design with large elements and relatively tight tolerances. The alternative approach presented in this design is to use additional imaging optics to correct for residual aberrations. Such a design can produce a system having high NA, large field size, small lens diameter, as well as relatively loose tolerances.

Correcting these residual aberrations can further increase the field size or increase the bandwidth while maintaining the field size. The design of FIG. 25 maintains the same approximately 0.4 mm field size as in the design of FIG. 16 and extends the bandwidth to cover 266 to 365 nm without need for refocusing. The worst case polychromatic wavefront error for the design of FIG. 25 is approximately 0.036 waves.

The design includes two air spaced doublets 2501, 2502, 2503, and 2504, the doublets 2501-2504 fashioned from fused silica and calcium fluoride. The doublets 2501-2504 focus light through three fused silica lens elements, namely lens elements 2505, 2506, and 2507. These lens elements 2505-2507 are in proximity to an internal field. Light is then collimated by an air spaced triplet 2508, 2509, and 2510. Light then forms an external pupil at 2511. The external pupil 2511 can be used for placing dark field apertures, Fourier filters, and beamsplitters.

Figure 25:
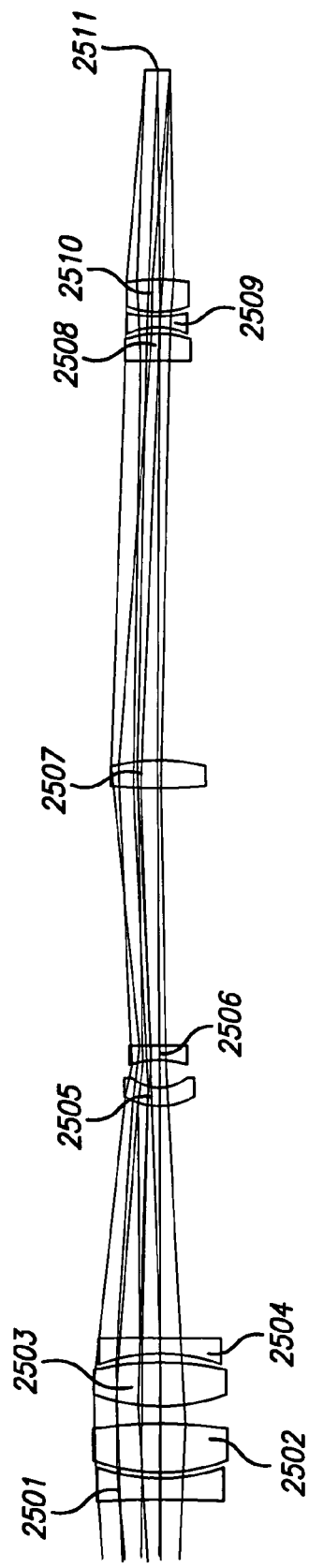
FIG. 25 illustrates a small sized tube lens arrangement in accordance with the present invention.

The lens prescription for the aspect of the invention illustrated in FIG. 25 is shown in Table 6.

TABLE 6

Prescription for lenses for the design of FIG. 25

| Surf | Radius | Thickness | Glass | Diameter |
|---|---|---|---|---|
| OBJ | Infinity | 0.3 | | 0.4 |
| 1 | 78 | 5.155765 | FUSED SILICA | 21 |
| 2 | −1031.094 | 6.132752 | | 21 |
| 3 | −13.38766 | 3.334036 | FUSED SILICA | 21.5 |
| 4 | −18.2281 | −3.334036 | MIRROR | 25.5 |
| 5 | −13.38766 | −6.132752 | | 21.5 |
| 6 | −1031.094 | −5.155765 | FUSED SILICA | 21 |
| 7 | 78 | 5.155765 | MIRROR | 21 |
| 8 | −1031.094 | 6.132752 | | 21 |
| 9 | −13.38766 | 3.334036 | FUSED SILICA | 21.5 |
| 10 | −18.2281 | 0.598511 | | 25.5 |
| 11 | Infinity | 0.595647 | | 0.87265 |
| 12 | −22.67364 | 1.496994 | FUSED SILICA | 1.716759 |
| 13 | −2.487035 | 5.332021 | | 2.721696 |
| 14 | −24.12325 | 1.749722 | FUSED SILICA | 6.761726 |
| 15 | −8.563906 | 1.647307 | | 7.426322 |
| 16 | Infinity | 1.017137 | | 8.707626 |
| 17 | −23.20559 | 1.75 | FUSED SILICA | 9.034138 |
| 18 | −10.09888 | 0.499806 | | 9.544791 |
| 19 | 459.357 | 2 | FUSED SILICA | 10.00487 |
| 20 | −12.90167 | 0.499731 | | 10.16545 |
| 21 | 9.888518 | 5.284916 | FUSED SILICA | 9.738469 |
| 22 | 5.468369 | 3.606566 | | 7.299015 |
| 23 | −6.158311 | 1.499744 | FUSED SILICA | 7.434168 |
| 24 | −10.89758 | 0.499623 | | 8.474502 |
| 25 | 18.52911 | 2 | FUSED SILICA | 9.287792 |
| 26 | −68.1321 | −15.25736 | | 9.417208 |
| STO | Infinity | 15.25736 | | 8.09706 |
| 28 | Infinity | 34.89506 | | 9.431455 |
| 29 | — | 0 | | — |
| 30 | Infinity | 6 | FUSED SILICA | 18.46143 |
| 31 | Infinity | 0 | | 25.39024 |
| 32 | — | 0 | | — |
| 33 | Infinity | 30 | | 17.16851 |
| 34 | — | 0 | | — |
| 35 | Infinity | 6 | FUSED SILICA | 26.81778 |
| 36 | Infinity | 0 | | 20.63295 |
| 37 | — | 0 | | — |
| 38 | Infinity | 81 | | 15.2277 |
| 39 | −159.7003 | 4 | FUSED SILICA | 22.27788 |
| 40 | 37.47386 | 0.999856 | | 22.92295 |
| 41 | 33.36497 | 9 | CAF2 | 23.58799 |
| 42 | −80.14523 | 3.436442 | | 24.07579 |
| 43 | 38.4464 | 8 | CAF2 | 23.97432 |
| 44 | −53.0633 | 1.5 | | 22.95647 |
| 45 | −39.45511 | 3 | FUSED SILICA | 22.35342 |
| 46 | 1094.058 | 43.27621 | | 21.67501 |
| 47 | 10.8487 | 3.18507 | FUSED SILICA | 12.40192 |
| 48 | 8.96916 | 4.999989 | | 10.71199 |
| 49 | −24.58978 | 2.5 | FUSED SILICA | 10.26452 |
| 50 | 117.1346 | 47.95638 | | 10.34545 |
| 51 | 175.9777 | 5 | FUSED SILICA | 16.71625 |
| 52 | −37.37344 | 74.18151 | | 17.10185 |
| 53 | −1113.4 | 5 | CAF2 | 11.5593 |
| 54 | −14.94822 | 0.99955 | | 11.38304 |
| 55 | −13.4032 | 2 | FUSED SILICA | 10.93698 |
| 56 | 18.26209 | 0.99969 | | 10.92178 |
| 57 | 17.51017 | 6 | CAF2 | 11.25199 |
| 58 | −33.75194 | 38.51994 | | 11.218 |
| 59 | — | 100 | | 4.910667 |
| IMA | Infinity | | | 16.34334 |

The tube lens design of FIG. 25 uses only fused silica and calcium fluoride. Both of these materials have transmissions from approximately 190 nm through the infrared. Thus a tube lens can be designed to operate with an objective that can be re-optimized for different center wavelengths. Other tube lens magnifications may be achieved using this design. The design of FIG. 25 can be re-optimized for different afocal magnifications depending on the desired overall magnification. Using the design presented herein, a focusing tube lens that directly forms an image that can expose a high speed sensor may be realized.

Figure 26:
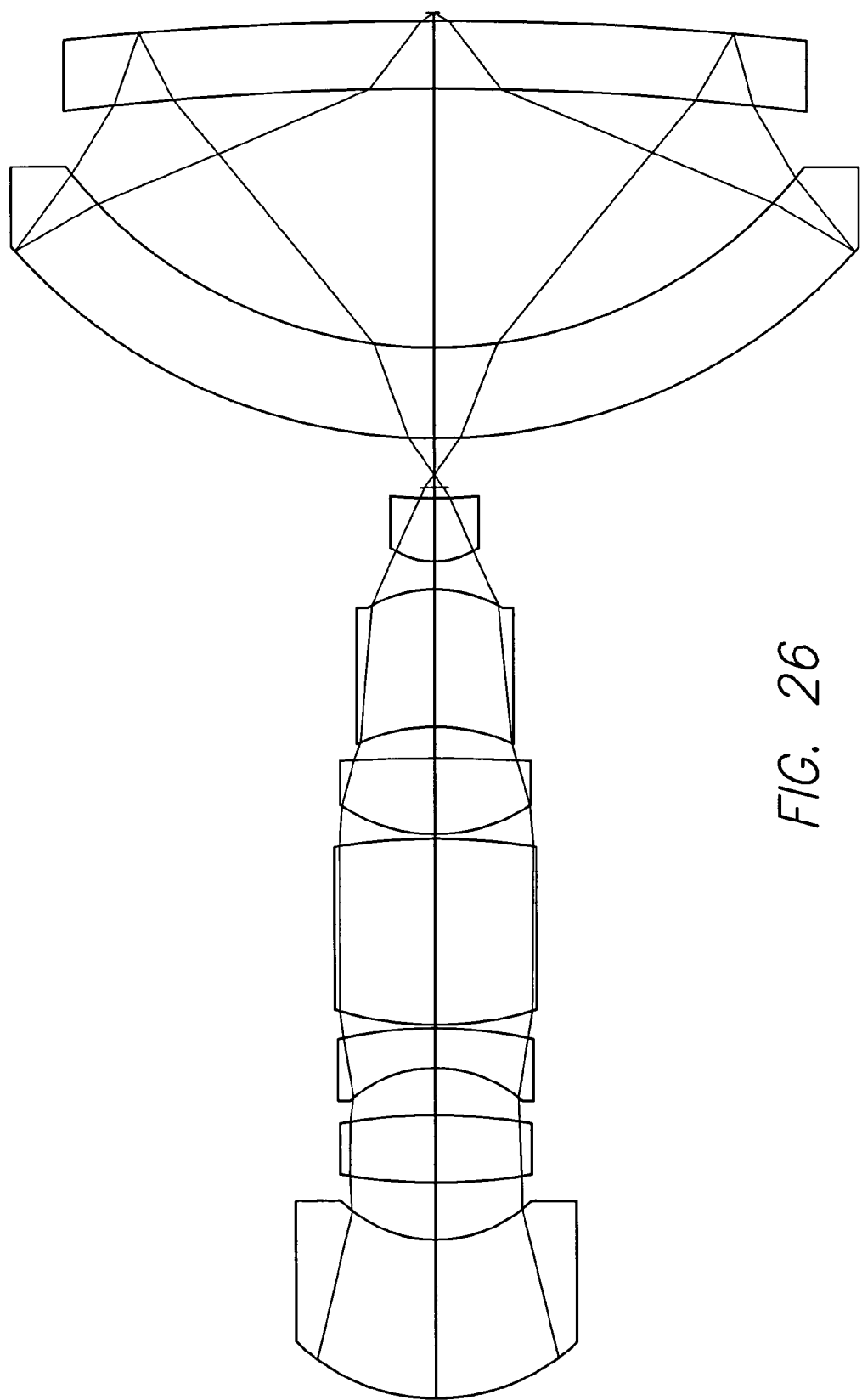
FIG. 26 is a design able to perform in the presence of wavelengths from approximately 311-315 nm, having approximately 26 mm diameter, a field size of approximately 0.28 mm, and NA of approximately 0.90.
Figure 29:
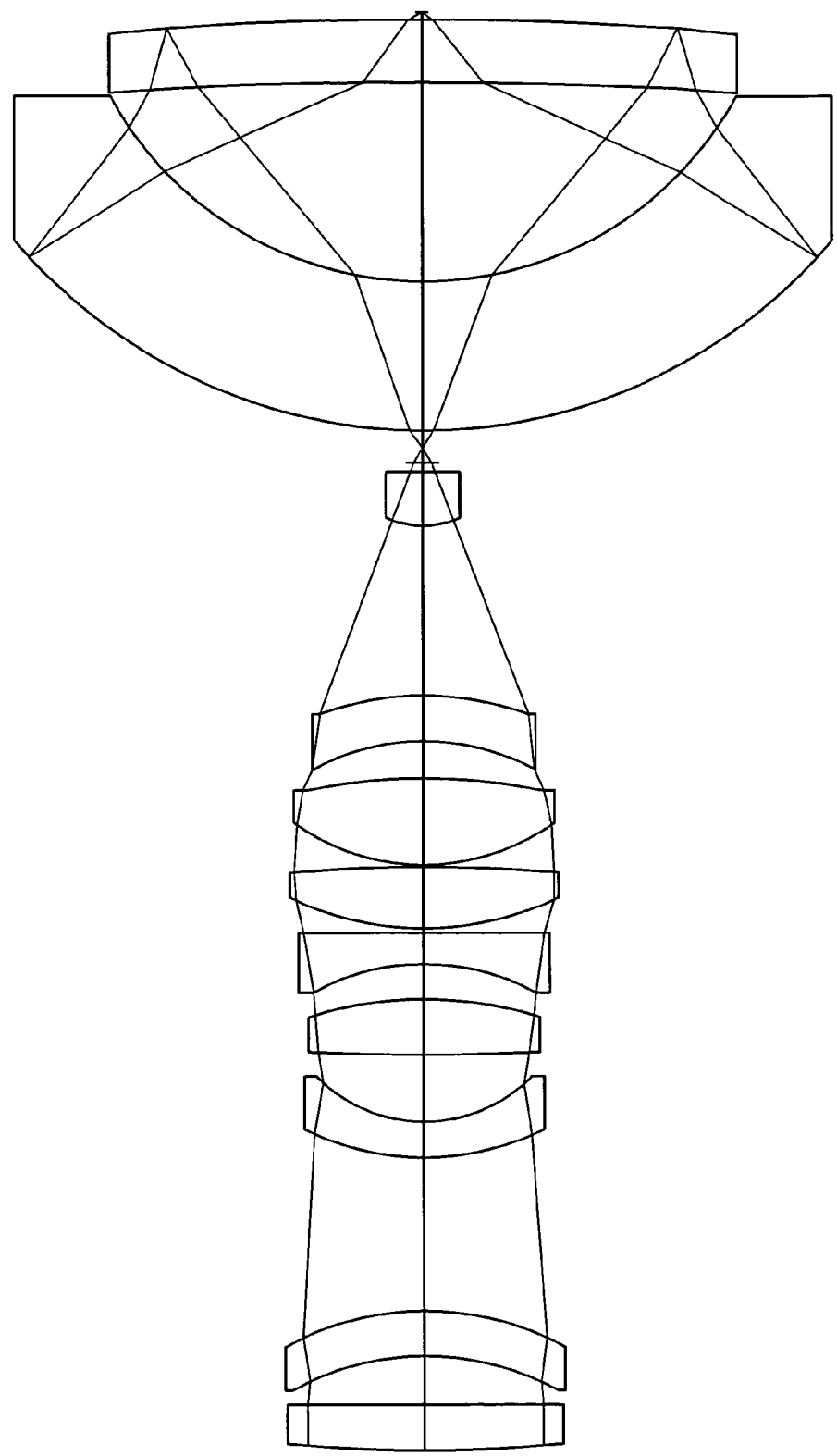
FIG. 29 illustrates a broad band design having approximately 26 mm diameter, a wavelength of between approximately 266 and 313 nm, field size of approximately 0.28 mm, and NA of approximately 0.90.

Further aspects of the design are presented in FIG. 29, where FIG. 26 is a design able to perform in the presence of wavelengths from approximately 311-315 nm, having approximately 26 mm diameter, a field size of approximately 0.28 mm, and NA of approximately 0.90. The lens prescription for this design is shown in Table 7.

TABLE 7

Prescription for lenses for the design of FIG. 26

| Surf | Radius | Thickness | Glass | Diameter |
|---|---|---|---|---|
| OBJ | Infinity | Infinity | | 0.000 |
| 1 | Infinity | 18.849 | | 8.538 |
| STO | Infinity | −18.849 | | 7.220 |
| 3 | 6.048 | 4.786 | Fused silica | 8.419 |
| 4 | 4.149 | 1.727 | | 5.777 |
| 5 | 19.860 | 2.000 | Fused silica | 5.724 |
| 6 | −17.207 | 1.449 | | 5.502 |
| 7 | −3.955 | 1.200 | Fused silica | 5.247 |
| 8 | −12.991 | 0.100 | | 5.861 |
| 9 | 10.518 | 5.617 | Fused silica | 6.098 |
| 10 | −15.147 | 0.100 | | 5.985 |
| 11 | 4.995 | 2.249 | Fused silica | 5.701 |
| 12 | −159.821 | 0.999 | | 5.037 |
| 13 | −5.316 | 4.092 | Fused silica | 4.659 |
| 14 | −4.477 | 0.904 | | 4.116 |
| 15 | 2.448 | 1.906 | Fused silica | 2.619 |
| 16 | 4.138 | 0.248 | | 1.101 |
| 17 | Infinity | 1.501 | | 0.801 |
| 18 | 16.697 | 2.750 | Fused silica | 25.240 |
| 19 | 13.901 | 7.871 | | 22.000 |
| 20 | −78.318 | 2.000 | Fused silica | 22.000 |
| 21 | −100.000 | −2.000 | MIRROR | 22.000 |
| 22 | −78.318 | −7.871 | | 22.000 |
| 23 | 13.901 | −2.750 | Fused silica | 22.000 |
| 24 | 16.697 | 2.750 | MIRROR | 25.240 |
| 25 | 13.901 | 7.871 | | 22.000 |
| 26 | −78.318 | 2.000 | Fused silica | 21.000 |
| 27 | −100.000 | 0.200 | | 22.000 |
| IMA | Infinity | | | 0.291 |

Figure 27:
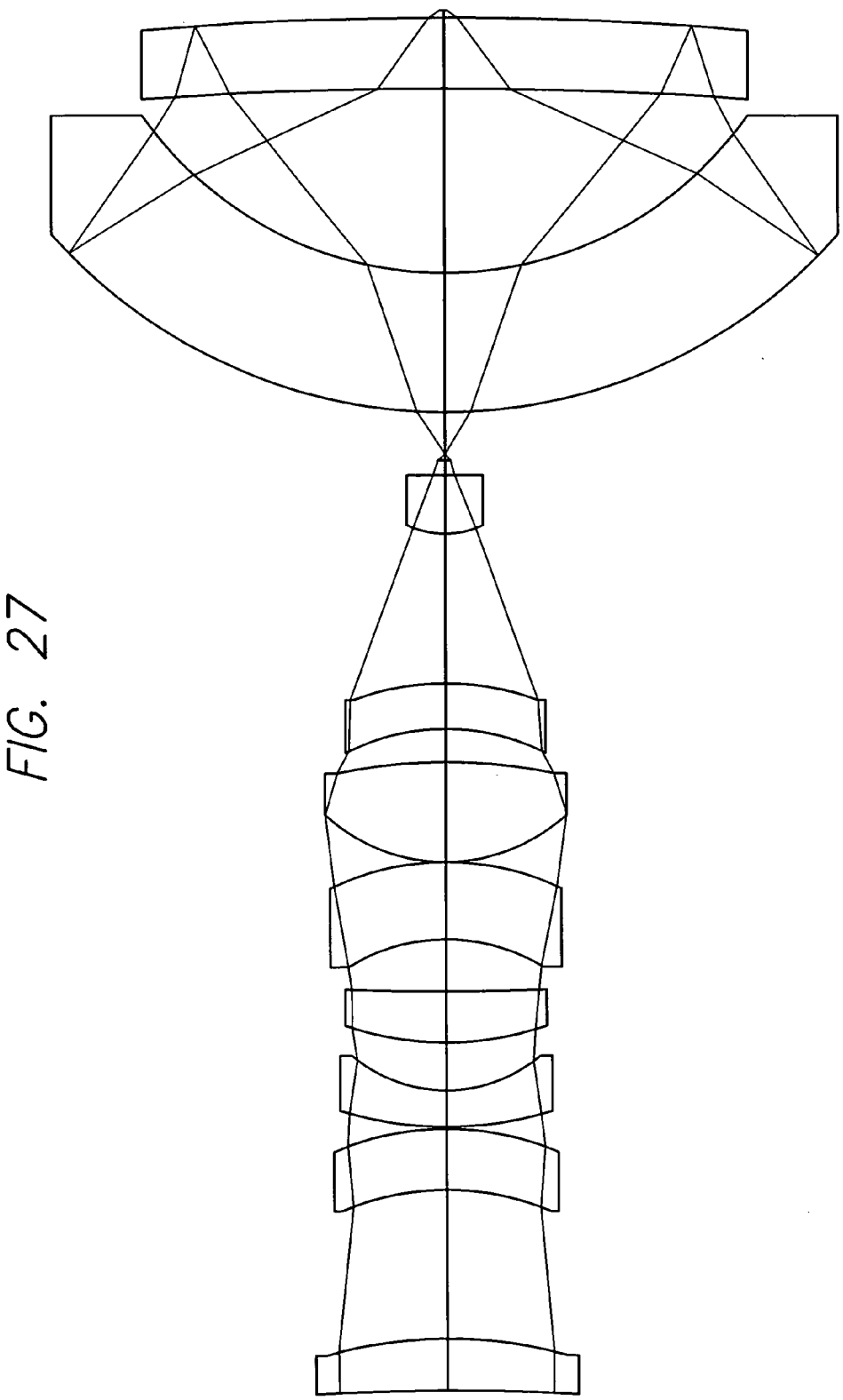
FIG. 27 is an approximately 0.28 mm field design having approximately 26 mm diameter, a wavelength of between approximately 297 and 313 nm, and NA of approximately 0.90.

FIG. 27 is an approximately 0.28 mm field design having approximately 26 mm diameter, a wavelength of between approximately 297 and 313 nm, and NA of appropriately 0.90. The lens prescription for this design shown in Table 8.

TABLE 8

Prescription for lenses for the design of FIG. 27

| Surf | Radius | Thickness | Glass | Diameter |
|---|---|---|---|---|
| OBJ | Infinity | Infinity | | 0.000 |
| 1 | Infinity | 20.163 | | 8.585 |
| STO | Infinity | −20.163 | | 7.170 |
| 3 | −115.896 | 1.750 | Fused silica | 8.591 |
| 4 | −16.723 | 5.036 | | 8.562 |
| 5 | −8.430 | 2.000 | Fused silica | 7.122 |
| 6 | −9.664 | 0.100 | | 7.349 |
| 7 | 11.608 | 1.200 | Fused silica | 7.019 |
| 8 | 4.779 | 1.598 | | 6.337 |
| 9 | 10.332 | 1.750 | Fused silica | 6.622 |
| 10 | 135.162 | 1.719 | | 6.592 |
| 11 | −6.281 | 2.555 | Fused silica | 6.583 |
| 12 | −9.052 | 0.100 | | 7.587 |
| 13 | 5.854 | 3.250 | Fused silica | 7.900 |
| 14 | −17.400 | 1.125 | | 7.264 |
| 15 | −7.026 | 1.499 | Fused silica | 6.559 |
| 16 | −8.971 | 5.055 | | 6.242 |
| 17 | 2.951 | 1.906 | Fused silica | 2.442 |
| 18 | −21.084 | 0.500 | | 1.255 |
| 19 | Infinity | 1.580 | | 0.314 |
| 20 | 17.135 | 4.713 | Fused silica | 26.000 |
| 21 | 12.147 | 6.064 | | 20.000 |
| 22 | −164.287 | 2.500 | Fused silica | 20.000 |
| 23 | −100.000 | −2.500 | MIRROR | 20.000 |
| 24 | −164.287 | −6.064 | | 20.000 |
| 25 | 12.147 | −4.713 | Fused silica | 20.000 |
| 26 | 17.135 | 4.713 | MIRROR | 26.000 |
| 27 | 12.147 | 6.064 | | 20.000 |
| 28 | −164.287 | 2.500 | Fused silica | 20.000 |
| 29 | −100.000 | 0.200 | | 20.000 |
| IMA | Infinity | | | 0.280 |

Figure 28:
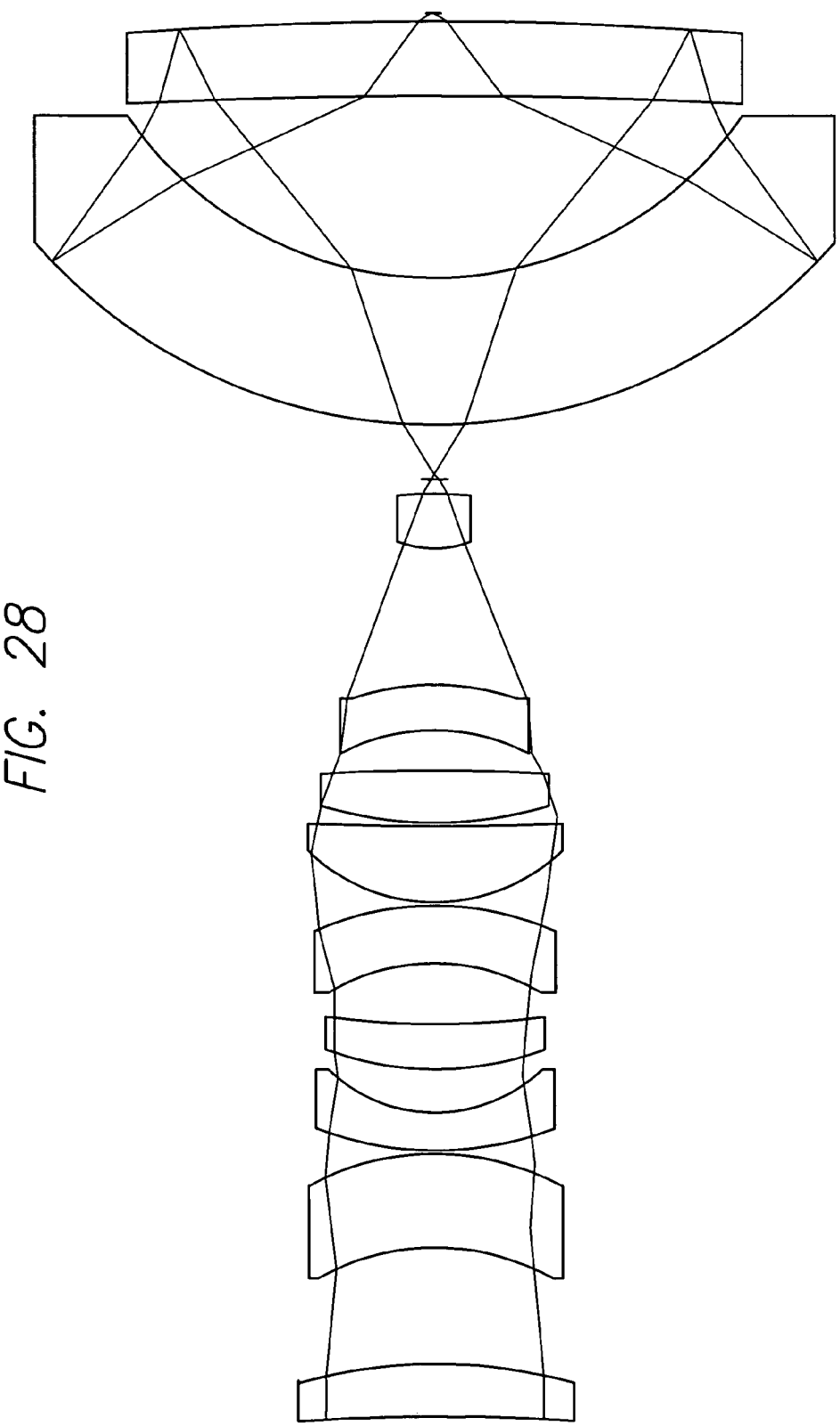
FIG. 28 is an approximately 0.4 mm field design having approximately 26 mm diameter, a wavelength of between approximately 297 and 313 nm, and NA of approximately 0.90.

FIG. 28 is an approximately 0.4 mm field design having approximately 26 mm diameter, a wavelength of between approximately 297 and 313 nm, and NA of approximately 0.90. The lens prescription for this design is shown in Table 9.

TABLE 9

Prescription for lenses for the design of FIG. 28

| Surf | Radius | Thickness | Glass | Diameter |
|---|---|---|---|---|
| OBJ | Infinity | Infinity | | 0.000 |
| 1.000 | Infinity | 17.977 | | 8.974 |
| STO | Infinity | −17.977 | | 7.171 |
| 3.000 | −73.415 | 1.750 | Fused silica | 8.988 |
| 4.000 | −16.484 | 3.889 | | 8.954 |
| 5.000 | −7.914 | 3.077 | Fused silica | 7.822 |
| 6.000 | −8.792 | 0.103 | | 8.317 |
| 7.000 | 10.984 | 1.200 | Fused silica | 7.777 |
| 8.000 | 4.966 | 1.460 | | 6.942 |
| 9.000 | 9.494 | 1.500 | Fused silica | 7.137 |
| 10.000 | 23.256 | 2.020 | | 7.037 |
| 11.000 | −6.669 | 1.871 | Fused silica | 7.044 |
| 12.000 | −10.034 | 0.100 | | 7.866 |
| 13.000 | 6.034 | 2.500 | Fused silica | 8.344 |
| 14.000 | 66.970 | 0.100 | | 7.904 |
| 15.000 | 12.304 | 1.750 | Fused silica | 7.531 |
| 16.000 | −60.162 | 1.300 | | 6.846 |
| 17.000 | −6.852 | 1.499 | Fused silica | 6.139 |
| 18.000 | −8.993 | 4.511 | | 5.804 |
| 19.000 | 3.141 | 1.750 | Fused silica | 2.466 |
| 20.000 | −15.561 | 0.499 | | 1.420 |
| 21.000 | Infinity | 1.841 | | 0.794 |
| 22.000 | 17.138 | 4.708 | Fused silica | 26.000 |
| 23.000 | 12.005 | 6.070 | | 20.000 |
| 24.000 | −177.009 | 2.500 | Fused silica | 20.000 |
| 25.000 | −100.000 | −2.500 | MIRROR | 20.000 |
| 26.000 | −177.009 | −6.070 | | 20.000 |
| 27.000 | 12.005 | −4.708 | Fused silica | 20.000 |
| 28.000 | 17.138 | 4.708 | MIRROR | 26.000 |
| 29.000 | 12.005 | 6.070 | | 20.000 |
| 30.000 | −177.009 | 2.500 | Fused silica | 20.000 |
| 31.000 | −100.000 | 0.200 | | 20.000 |
| IMA | Infinity | | | 0.401 |

FIG. 29 illustrates a broad band design having approximately 26 mm diameter, a wavelength of between approximately 266 and 313 nm, field size of approximately 0.28 mm, and NA of approximately 0.90. The lens prescription for this design is shown in Table 10.

TABLE 10

Prescription for lenses for the design of FIG. 29

| Surf | Radius | Thickness | Glass | Diameter |
|---|---|---|---|---|
| OBJ | Infinity | Infinity | | 0.000 |
| 1.000 | Infinity | 19.109 | | 8.783 |
| STO | Infinity | −19.109 | | 7.500 |
| 3.000 | 59.725 | 1.500 | F_SILICA | 8.772 |
| 4.000 | −337.579 | 1.500 | | 8.650 |
| 5.000 | −9.464 | 1.500 | F_SILICA | 8.574 |
| 6.000 | −9.415 | 4.925 | | 8.900 |
| 7.000 | 8.637 | 1.200 | F_SILICA | 7.651 |
| 8.000 | 4.897 | 2.128 | | 6.903 |
| 9.000 | 214.349 | 1.750 | F_SILICA | 7.117 |
| 10.000 | −12.598 | 1.147 | | 7.334 |
| 11.000 | −7.560 | 1.000 | F_SILICA | 7.320 |
| 12.000 | −772.023 | 0.100 | | 7.974 |
| 13.000 | 9.411 | 2.000 | F_SILICA | 8.548 |
| 14.000 | −56.012 | 0.099 | | 8.529 |
| 15.000 | 7.107 | 2.750 | F_SILICA | 8.352 |
| 16.000 | −22.495 | 1.159 | | 7.805 |
| 17.000 | −7.960 | 1.499 | F_SILICA | 7.103 |
| 18.000 | −10.073 | 5.482 | | 6.716 |
| 19.000 | 3.034 | 1.748 | F_SILICA | 2.380 |
| 20.000 | −20.121 | 0.245 | | 1.276 |

TABLE 10-continued

Prescription for lenses for the design of FIG. 29

| Surf | Radius | Thickness | Glass | Diameter |
|---|---|---|---|---|
| 21.000 | Infinity | 1.041 | | 0.955 |
| 22.000 | 16.855 | 4.806 | F_SILICA | 26.000 |
| 23.000 | 11.392 | 6.422 | | 20.000 |
| 24.000 | −133.502 | 2.000 | F_SILICA | 20.000 |
| 25.000 | −100.000 | −2.000 | MIRROR | 20.000 |
| 26.000 | −133.502 | −6.422 | | 20.000 |
| 27.000 | 11.392 | −4.806 | F_SILICA | 20.000 |
| 28.000 | 16.855 | 4.806 | MIRROR | 26.000 |
| 29.000 | 11.392 | 6.422 | | 20.000 |
| 30.000 | −133.502 | 2.000 | F_SILICA | 20.000 |
| 31.000 | −100.000 | 0.200 | | 20.000 |
| IMA | Infinity | | | 0.283 |

Figure 30:
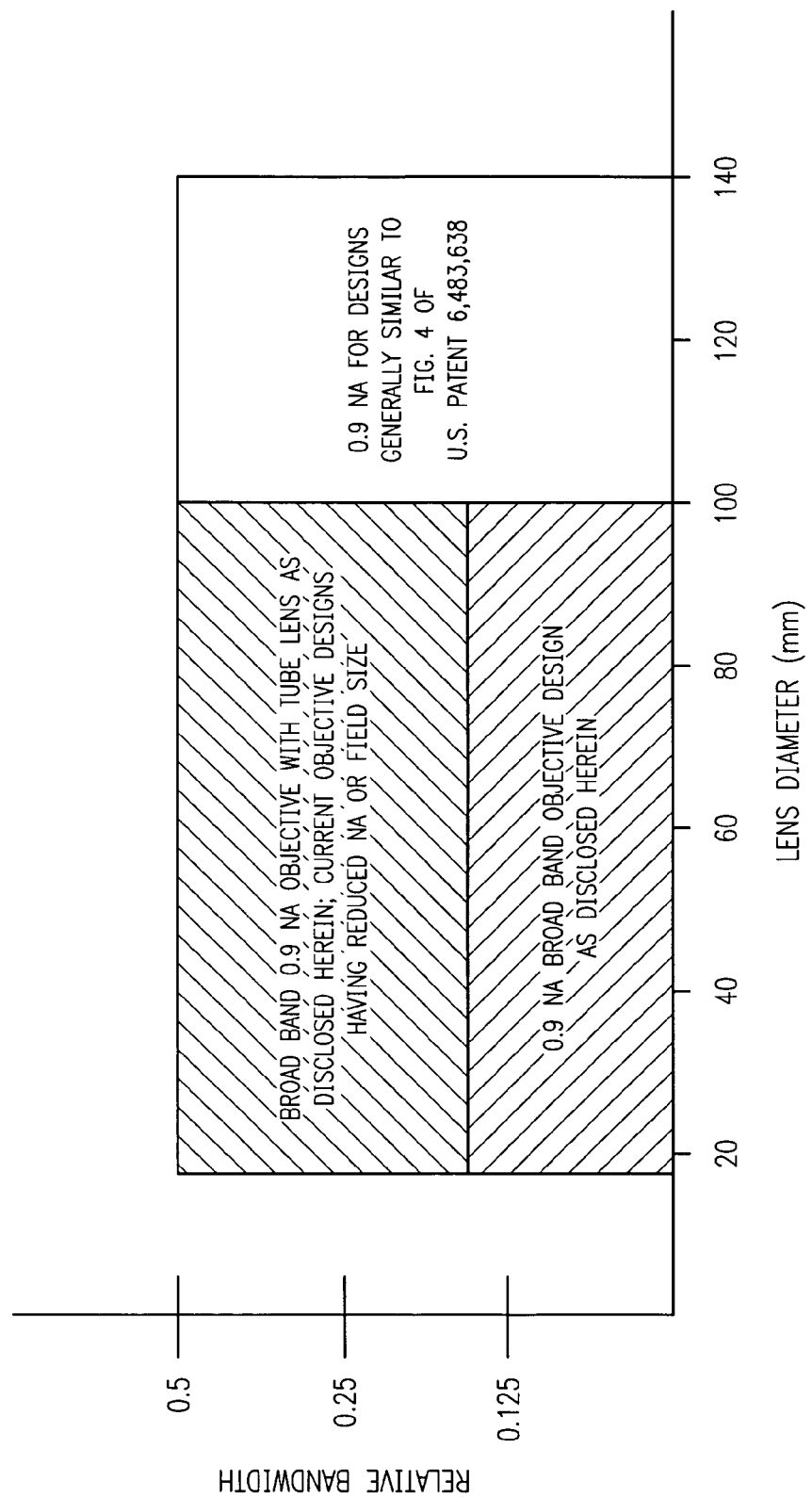
FIG. 30 is a graph comparing relative bandwidth versus the maximum lens element diameter of certain objective designs, including the current objective design.

FIG. 30 is a graph contrasting previous objectives against the current objective design in terms of relative bandwidth and maximum lens diameter. Relative bandwidth is defined as the bandwidth of the objective divided by the center wavelength. Previous systems are well corrected for relative bandwidths of at least 0.5 using lenses with maximum diameters greater than 100 mm. Current objective designs as presented herein use a single glass material and are self corrected up to approximately 0.16 using lenses with maximum diameters from around 20 mm up to 100 mm. Further correction of these objectives over relative bandwidths up to 0.5 are possible using tube lenses to correct residual chromatic aberrations as in the designs of FIGS. 18 and 25. Similar correction is also possible for the objective alone by restricting NA or field size requirements.

Figure 31:
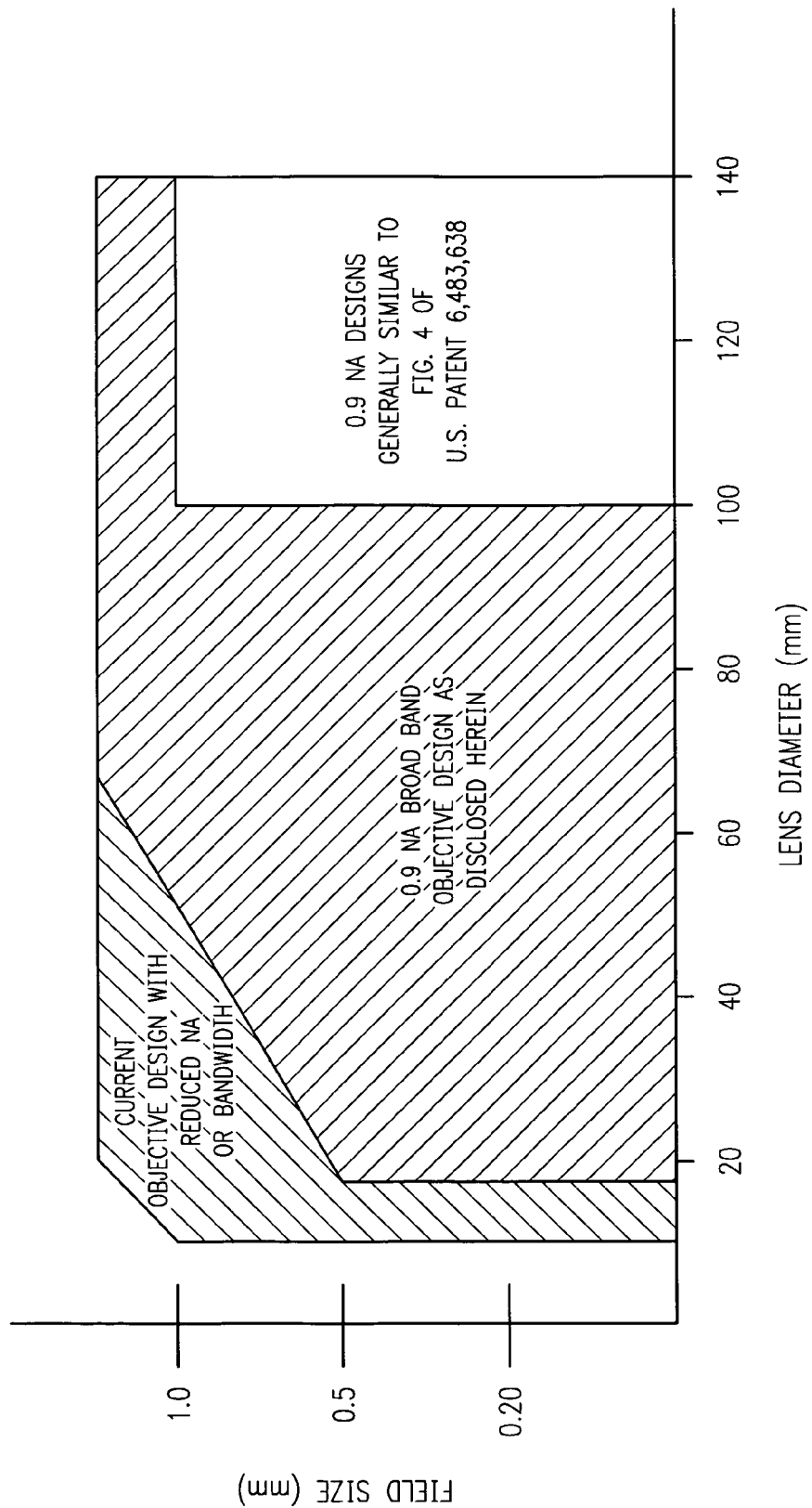
FIG. 31 is a graph comparing field size versus the maximum lens element diameter of certain objective designs, including the present objective design.

FIG. 31 is a graph contrasting previous objective designs and the present objective design in terms of field size and maximum lens diameter. Previous designs tend to be well corrected for field sizes of 1 mm using lenses with maximum diameters greater than 100 mm. Current objectives using the designs presented herein are corrected for field sizes of 0.4 mm using lenses with maximum diameters from around 25 mm, and 1.0 mm field sizes using lens diameters of 58 mm. From this and the graph of FIG. 30, the ratio between field size and diameter of the largest element (including the Mangin mirror arrangement, field lens(es), and focusing lens(es), is generally less than 100 to 1, and may be less than 60 to 1. For example, the 58 mm lens diameter versus the 1.0 mm field size produces a ratio of 58 to 1. Larger field sizes are also possible with increasing lens diameter. Further correction of these objectives over larger field sizes are possible using tube lenses to correct residual chromatic aberrations as in the designs of FIGS. 18 and 25. Similar correction is also possible for the objective alone by restricting NA or bandwidth requirements.

FIG. 20A shows a fixed magnification configuration. Light from pupil plane 2001 is collected by optics 2002 and forms subsequent image 2003. FIG. 20B shows a fixed length zoom system. Light from the pupil 2004 is collected by zoom optics 2005 and forms subsequent image 2006. The distance between pupil plane 2004 and image plane 2006 is typically fixed. The zoom optics 2005 may be shifted to change the resulting magnification at the image plane 2006. Zoom optics may include two or more groups of lenses, where magnification can be changed by changing the spacing between the lens groups. Once magnification is set, the image can be refocused by changing the position of the zoom group 2005 relative to the image 2006. The zoom range is limited by the complexity of the lens system and the number of independent lens groups. A broad band zoom using two groups of lenses can achieve a plus-or-minus 10% zoom range.

FIG. 20C shows a varifocal magnification configuration. Light from the pupil 2007 may be collected by the varifocal optics 2008 and form subsequent image at 2009. Changing the location of the varifocal optics 2008 relative to the pupil 2007 and refocusing by changing the spacing between the pupil 2007 and image plane 2009 can change the magnification. The magnification range for a varifocal system can be over approximately 4 to 1 and is limited by the allowable distance between the pupil 2007 and image plane 2009.

Various implementations for the objectives and image forming optics may be employed in a general image forming system. A single fixed objective may be used. The single objective may support all the desired imaging and inspection modes. Such a design is achievable if the imaging system supports a relatively wide bandwidth and relatively high numerical aperture. Bandwidth can be narrowed using specific spectral filters. Numerical aperture can be reduced to a desired value by using internal apertures.

Figure 21:
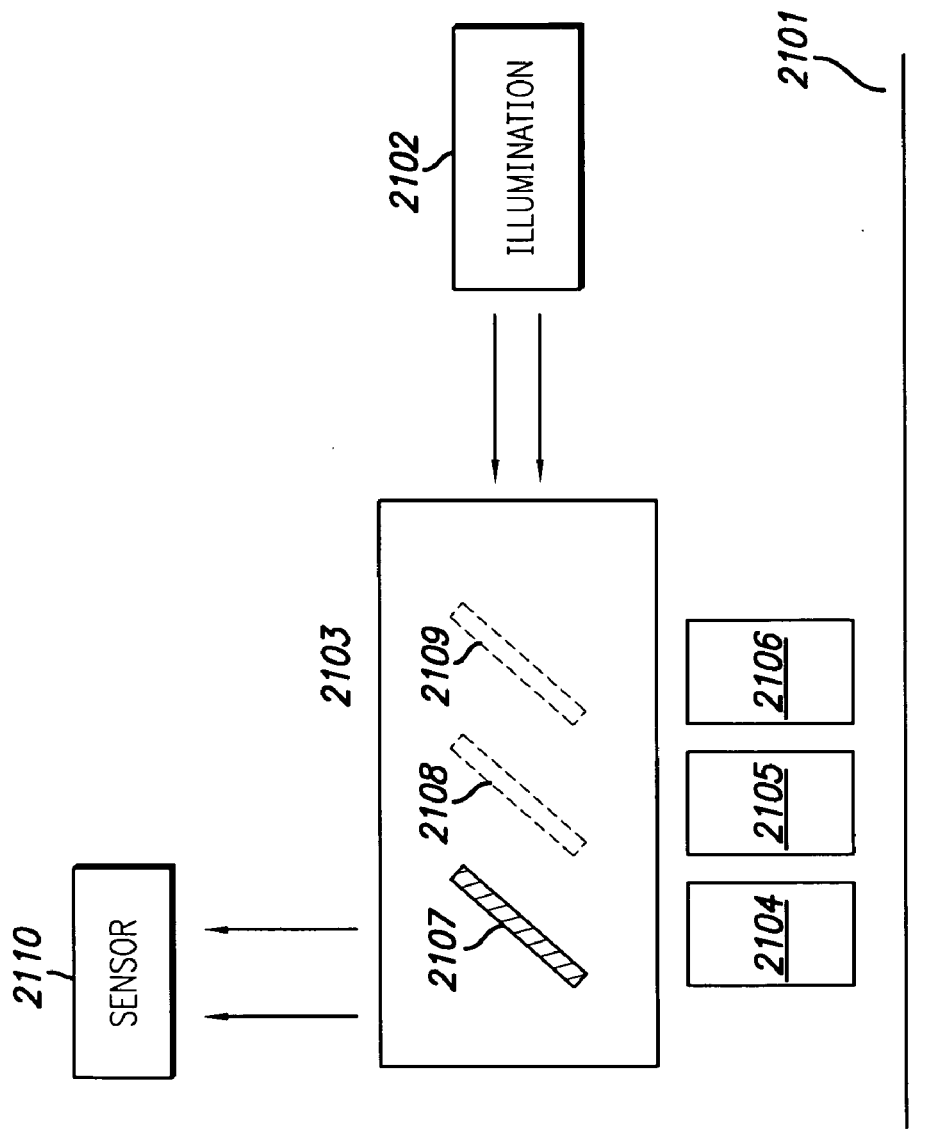
FIG. 21 shows the use of multiple fixed objectives.

Multiple fixed objectives may also be used as shown in FIG. 21. From FIG. 21, objectives 2104, 2105, and 2106 are fixed with respect to each other. Sample 2101 moves on a stage, which positions the sample in the desired position depending on the objective being used. Illumination 2102 enters through beamsplitters 2103. Light collected from the sample by the objectives will pass beamsplitters 2103 before passing to the image forming optics and sensor 2110. In the geometry shown, the illumination 2102 reflects from the beamsplitters 2103 before entering the objective and the light from the sample transmits through beamsplitters 2103. The geometry can be revesed such that the illumination 2102 transmits through beamsplitters 2103 and the light from the sample reflects from the beamsplitters 2103. Three objectives are shown in this figure, but any number is possible. Each objective has its optical axis a fixed distance away from the other objective. Optionally, the distance between the optical axis of the objectives could be adjustable. Different objectives in such a design may be optimized for different wavelength ranges or inspection modes. Inspection may be done with one objective at a time or using multiple objectives simultaneously. The beamsplitter module 2103 consists of a beamsplitter 2107, 2108, and 2109 for each objective 2104, 2105, and 2106. When objectives are optimized for different wavelengths, the beamsplitters can use coatings that reflect the desired wavelength. For example, the illumination 2102 consists of wavelengths from approximately 260 nm to 546 nm. Objective 2106 can be optimized in the visible spectrum from approximately 405 to 546 nm. Objective 2105 can be optimized from approximately 320 to 405 nm and objective 2104 can be optimized from approximately 260 to 320 nm. Such an arrangement could require beamsplitter 2109 to have partial reflection from approximately 405 to 546 nm and high transmission from approximately 260 to 405 nm. Beams splitter 2108 could partially reflect wavelengths from approximately 320 to 405 nm and highly transmit wavelengths from approximately 260 to 320 nm. Beamsplitter 2107 could then partially reflect wavelengths from approximately 260 to 320 nm. Another option is to slide the beamsplitters in and out as needed depending on timing, orientation and/or geometry. The beamsplitter used in such a design may be optimized for partial reflections in the corrected wavelength band of the objective, thereby allowing for spectral overlap between the objectives. For example, objective 2106 can be optimized from approximately 365 to 546 nm, objective 2105 can be optimized from approximately 320 to 405 nm and objective 2104 can be optimized from approximately 260 to 365 nm.

Figure 22:
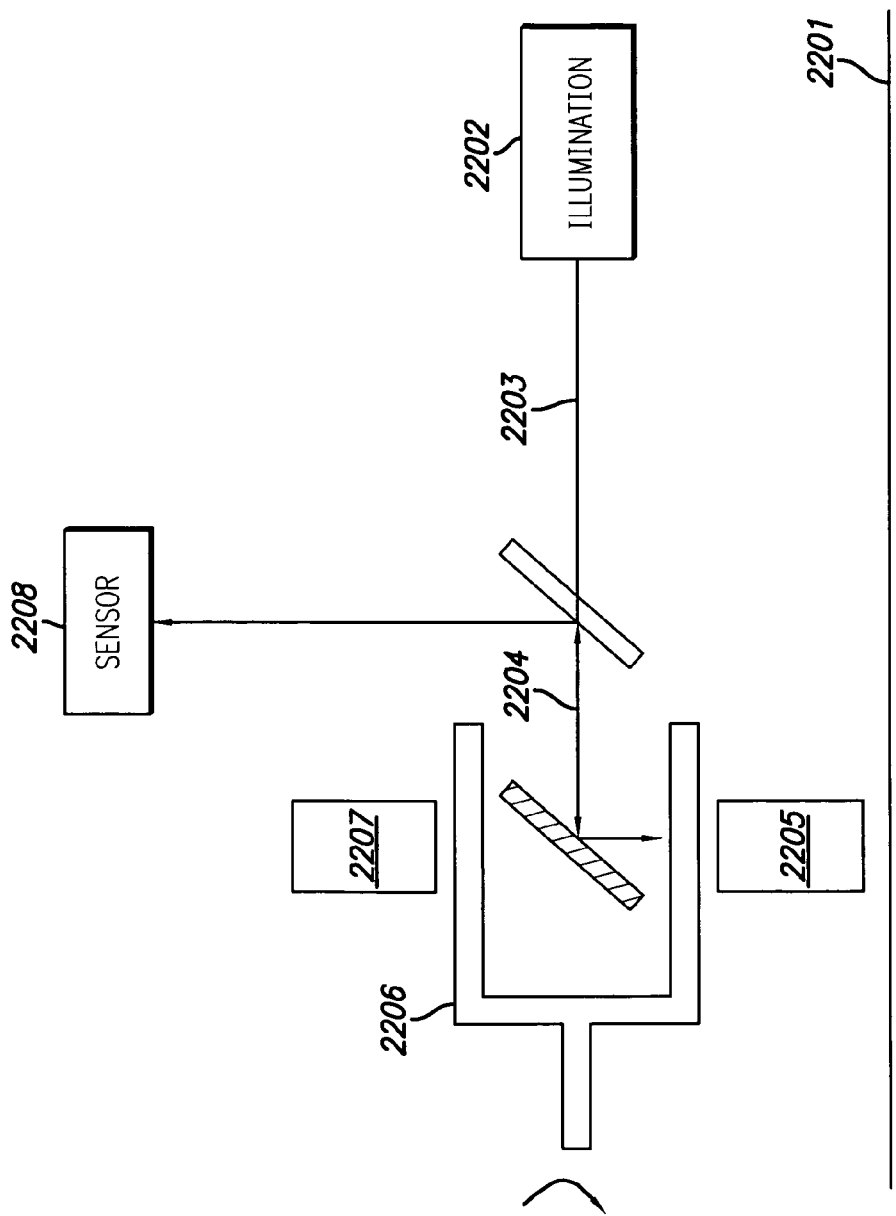
FIG. 22 illustrates a turret design used to move multiple objectives to image the sample or specimen.

To move multiple objectives in proximity to image the sample, rotary turrets may be used on standard microscopes. FIG. 22 shows a particular aspect of a turret design. From FIG. 22, illumination 2202 transmits though beam splitter 2203 and subsequently reflects of mirror 2204. Illumination 2202 then transmits through objective 2205 and illuminates the sample 2201. Light reflected and scattered from sample 2201 is then collected by objective 2205 and subsequently reflects from mirror 2204 and beam splitter 2203. Light then passes through image forming optics which form an image on sensor 2208. Turret 2206 can move different objectives into place to image the sample. Two objectives 2205 and 2207 are shown in FIG. 22 for clarity. Many objectives are possible depending on the diameter of the turret. Other designs for moving objectives in proximity of a sample are available, including but not limited to translating the objectives laterally on a stage, translating the objectives on an arc using a goniometer. In addition, any combination of fixed objectives and multiple objectives on a turret can be achieved in accordance with the present system.

Figure 23:
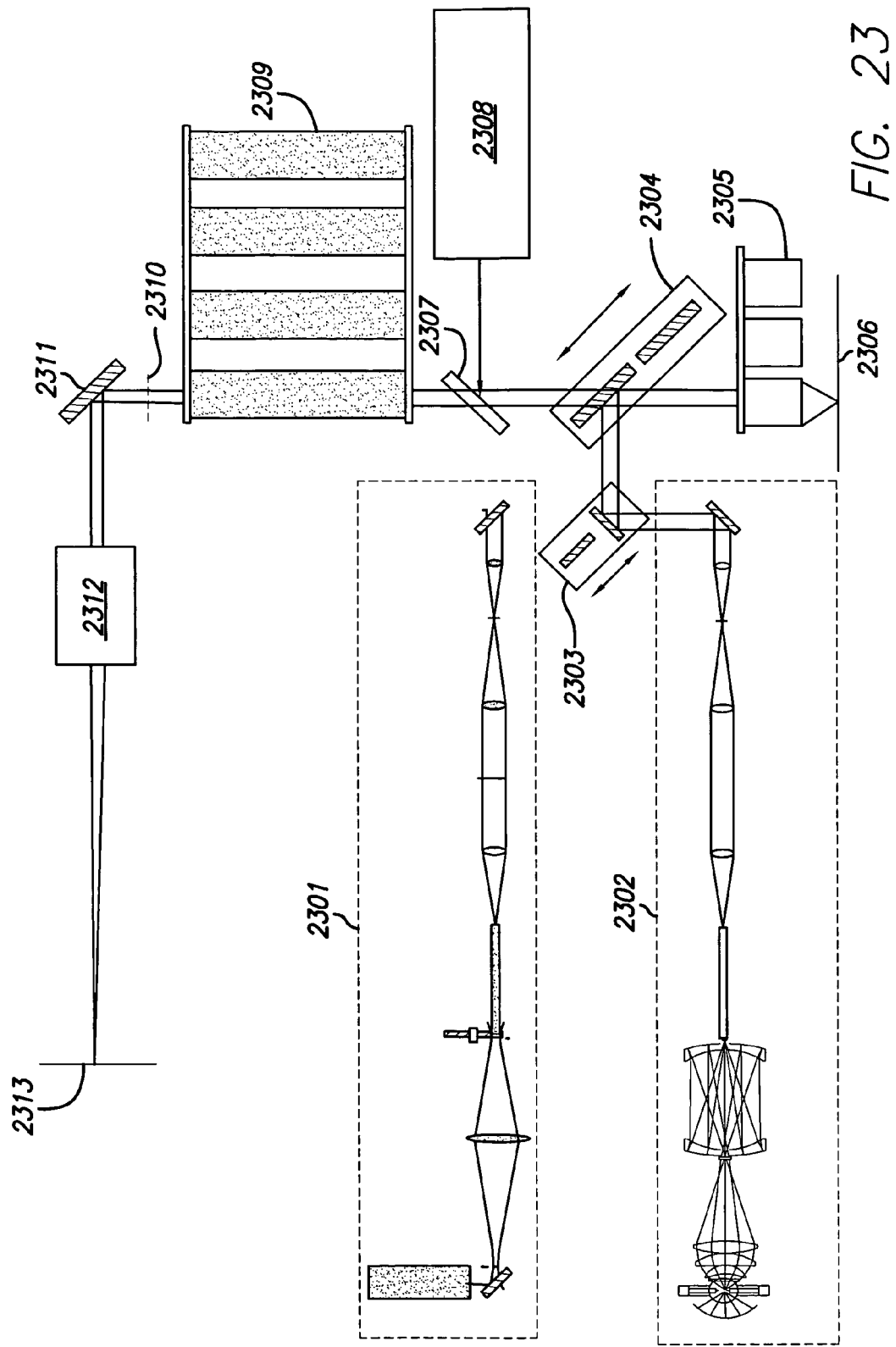
FIG. 23 illustrates a system architecture supporting multiple modes in accordance with the small objective and concepts presented herein.

A system architecture supporting multiple imaging modes is presented in FIG. 23. The system illustrated in FIG. 23 uses both a laser based illumination subsystem 2301 and a lamp based illumination subsystem 2302. The laser based illumination subsystem 2301 utilizes a rotating diffuser and light pipe. Laser operation is continuous with a narrow wavelength, and may operate at, for example, 266 nm or 355 nm. The lamp based illumination subsystem 2302 utilizes a catadioptric collection group and light pipe. The lamp in the lamp based illumination subsystem 2302 is a HgXe lamp and the catadioptric group may generally be optimized for wavelengths between approximately 260-700 nm. Selecting between the two illumination subsystems is accomplished by using a sliding assembly with mirrors to direct the illumination 2303. Illumination may be directed toward a beamsplitter sliding assembly 2304. Different beamsplitters on this assembly can be can be used based on the desired wavelength and imaging mode. Illumination light energy may enter one objective on a turret containing multiple objectives 2305. The system may then illuminate the region of interest on the sample 2306 using the selected objective from the multiple objectives 2306. The turret typically may contain at least three objectives. At least one objective on the turret may be a small sized catadioptric objective with a field size of, for example, approximately 0.4 mm and lenses with diameters of less than approximately 25 mm. The corrected wavelength range of the catadioptric objective may be approximately 260-320 nm. Other objectives used on the turret can be standard refractive designs optimized from, for example, approximately 365 nm through the visible. One of the objectives may he a low magnification objective with an NA of less than 0.2 that is primarily used for sample or specimen alignment. Autofocus system 2308 may measure sample or specimen focus position.

Objective 2305 collects light energy reflected from the specimen 2306 and the light energy passes through beamsplitter assembly 2304 and dichroic mirror 2307. Light then may pass through a tube lens in turret 2309. At least four tube lenses may be made available for changing system magnification. The system may include different tube lenses optimized for different wavelength ranges and objectives. Light from the tube lens then forms a pupil image at point 2310. At least one set of apertures can be made available at point 2310 to support ring dark field mode operation. Light then reflects off mirror or reflecting element 2311 and passes through zoom lens system 2312. Zoom lens system 2312 may have a zoom range of in the range of at least approximately five per cent. Light energy then forms an image on sensor 2313. Sensor 2313 may be a back-thinned silicon sensor that operates in TDI mode, but other sensors may be used.

Light from the autofocus system at a wavelength greater than 600 nm enters dichroic mirror 2307. Dichroic mirror 2307 reflects light at the autofocus wavelength and transmits at the imaging wavelengths between approximately 260 and 600 nm. Autofocus light then passes through beamsplitter assembly 2304 and an objective on turret assembly 2305 before illuminating sample or specimen 2306. The reflected autofocus light from sample or specimen 2306 may then pass back through the objective on turret 2305 and to beamsplitter assembly 2304 before reflecting off beamsplitter 2307 and returning to the autofocus system where focus position of the sample may be measured.

The wide range of illumination and collection angles possible with this catadioptric imaging system allows it to support multiple imaging modes. As may be appreciated from the previous paragraphs, multiple imaging modes can be implemented using a single optical system or machine in connection with the illumination device. The high NA disclosed for illumination and collection permits the implementation of imaging modes using the same optical system, thereby allowing optimization of imaging for different types of defects or samples. The small sized catadioptric system can be adapted to various UV imaging applications, including use of the design as a UV microscope objective, a collector of surface scattered UV light in a wafer inspection apparatus, or as mask projection optics for a UV photolithography system.

The small sized catadioptric optical apparatus presented to support bright field and dark field imaging and inspection may also be used in other applications. The design can be optimized by one skilled in the art for wavelengths from the visible range to the deep UV range and to the vacuum UV range. Longer wavelengths can be optimized for larger bandwidths due to diminished glass dispersion. For example, bandwidths of greater than 140 nm are possible with a two material design and a center wavelength of 300 nm. The light energy can include shorter wavelengths and the design permits use of multiple wavelengths. For semiconductor inspection, the designs presented can support bright field, laser directional dark field, ring dark field, and simultaneous bright-field and dark-field schemes. The optical designs presented are also suited for use as a lithography lens or for lithography simulation, a research tool for micro-electronic development, florescence measurements, or in biology where a long working distance is required for sample clearance. Due to the ability of this objective to provide applications in the presence of extremely varied light wavelengths and spectral bandwidths, the designs are well suited for florescence measurements.

Autofocus

As the semiconductor device moves in the case of high speed inspection, the system corrects minute changes in the focus position. Thus such a system may be served by employing automatic focusing to maintain a high fidelity image.

The present system may employ an autofocus subsystem in connection with the positioning subsystem to automatically focus the light energy received from the illumination subsystem. Many different types of automatic focusing subsystems can be successfully applied in semiconductor inspection. These automatic focusing subsystems detect focus changes, focus on the sample, and use feedback to maintain the desired focus position.

The system may detect focus changes using various methodologies. One such method that may be employed is described in U.S. Pat. No. 4,639,587, assigned to KLA Instruments, describing an automatic focusing system that compares two masks and is used primarily for the inspection of semiconductor wafers. The technique can be employed to measure the focus position of a wafer containing a partially fabricated integrated circuit. Measuring the best focus position on a wafer containing a partially fabricated integrated circuit is complicated by the potential presence of multiple layers having complex geometries with varying reflectivities. The desired focus position, and the focus position for an autofocus system, is usually the top layer of the wafer. While separating an actual focus change from a change in the circuit patterns can be difficult, the technique discussed in the '587 patent produces a best focus location that is an average of the different levels on the wafer multiplied by the reflected signal. In the present design, focus location and correction is relatively easier at short wavelengths where materials may more strongly absorb the light energy.

Another automatic focus technique that may be employed in the current design involves astigmatic focusing on a quadrant detector. In this method, the system focuses light from an illumination source onto the sample surface, typically through the imaging subsystem optics. The system then focuses the reflected light, typically collected by the imaging subsystem optics, using an astigmatic lens onto a quadrant detector. As the system moves the sample through focus, the shape of the focus changes and is measured by the quadrant detector. This astigmatic focusing technique typically works effectively for samples having limited topology variations.

Detecting focus changes includes accounting for separation of the automatic focusing signal from the image in the imaging subsystem. Both variable wavelength and different field aspects may be incorporated. If a different wavelength is used between the autofocus and the imaging subsystems, a dichroic device such as a beamsplitter or grating may be used to separate the signals. If the system employs a slightly different position on the sample for the autofocus and imaging subsystems, the system can separate the signals at an internal field plane within the imaging subsystem or at the final image plane. In this case, the same illumination source can be used for the illumination and autofocus subsystems.

Focusing on the specimen, such as a semiconductor device, as distinguished from performing an autofocus function, may be accomplished by moving the semiconducor device or moving the objective to maintain focus. For large high precision optical systems as described herein, moving the objective to achieve focus may not be feasible. In such a situation, the system may employ one or more of the optical elements in the imaging subsystem to compensate for focus changes. Adequate performance may result when focusing does not greatly affect the magnification or telecentricity of the imaging subsystem.

Using autofocus, the system may use feedback control to maintain proper focus. Feedback control accounts for resonance of the different autofocus mechanical and electronic components and minimize overshoot and ringing. Such feedback, controls are used in autofocus systems for semiconductor inspection, compact disc players, and other high precision optical devices. Particular feedback loop parameters, such as those used in a Proportional Integral Derivative (PID) loop controller, can be designed by those skilled in the art and are specific to the autofocus subsystem design.

Sensor

The sensor employed in the present system is directly related to the, remaining components of the system and may be a different type of sensor for different applications, including but not limited to a single point diode type detector or an area type detector such as a CCD or a CCD operating in the Time Delay and Integration (TDI) mode. The sensor may have high quantum efficiency, low noise, and a good Modulation Transfer Function (MTF). Back thinned CCD sensors can be used for this purpose. Many other types of sensors may be employed, including but not limited to front side devices with open silicon areas, lumogen coated front side sensors, photo-diamond sensors, and silicon carbide sensors. Photo-diamond type and silicon carbide type sensors tend to have very little sensitivity to visible wavelengths, so if such wavelengths are used in the system, other sensors may perform better.

The sensors employed in the present system can operate in different modes, including frame transfer and time delay and integration (TDI). The frame transfer mode may be employed when the system uses a single laser pulse to illuminate an area on the specimen. Each pulse can correspond to one frame of the sensor, such that the system can read out two halves of the detector simultaneously for increased data rates and overall throughput. If the system uses multiple pulses from a laser to expose a single area on the specimen, the system may employ a TDI mode sensor. In special inspection modes, such as confocal and dark field inspection modes, single point detectors or arrays of single point detectors may also be used.

The small sized catadioptric system disclosed herein performs a high speed sample inspection with high resolution. For example, an inspection system with a pixel size of 50 nm would require a data rate of 1.1 Gpixels/second to scan an area of 10 cm×10 cm in one hour. Increasing the inspection speed tends to reduce the per-sample cost of an inspection system. The sensor used may therefore provide very low noise levels at these high data rates. For example, less than one count of noise out of 256 counts of signal may be desirable. Often less than one count of noise out of 1024 counts of signal can be required to deliver acceptable performance. Low noise generation in this environment, requires specific component choices and positioning for the sensor layout, amplifier, packaging, and readout electronics, but such a design is generally within the abilities of those skilled in the art. The electrical design of each of these components can minimize the effects of crosstalk, feedthrough and adequately isolate the ground.

The sensor subsystem includes components that provide high quantum efficiency, long lifetimes, and a high contrast transfer function. High quantum efficiencies generally require less light from the illumination system to fully expose the sensor. Higher quantum efficiency also requires less energy on the sample surface, thus tending to limit the potential for damage from the high peak powers of an excimer laser pulse. Long lifetimes minimize the possibility that the sensor performance changes with time, decreasing the risk of system recalibration. Typical performance changes with DUV exposure are an increase in dark current and a decrease in quantum efficiency.

The system may employ a high Contrast Transfer Function (CTF) to detect the image with adequate resolution. If the imaging subsystem produces a very high resolution image, the inspection system may not be able to detect the high resolution image if the sensor has a low CTF. A CTF generally as low as approximately 0.4 is acceptable for an inspection system, however a value of 0.6 or greater can produce desirable effects.

One possible sensor that may be employed in the current design is presented in U.S. Pat. No. 4,877,326, entitled "Method and Apparatus for Optical Inspection of Substrates,"

assigned to KLA-Tencor Corporation, the entirety of which is incorporated herein by reference.

The sensor may be back illuminated or front illuminated, where front illumination may include virtual phase design, solid state, with open areas to be UV sensitive, and may incorporate sensors with florescent coatings. The system may be a point, line, 2D, multitap readout, linear, photodiode array, CCD, or split readout to double the speed. The sensor may be a diamond based sensor, and may have antiblooming capability. The sensor may be staggered or comprise multiple sensors in one package. Sensor electronics may provide for exposure correction.

The sensor employed may further include aspects of high quantum efficiency at the excimer laser wavelength. Back thinned silicon sensors may be employed to offer adequate performance. The sensor further may have high resolution capabilities to support high resolution imaging, high speed capability to support high speed inspection, and low noise and high dynamic range to support the various defect detection modes discussed herein.

Data Acquisition

The data acquisition subsystem of the present system includes frame mode operation and TDI mode operation. When operating in frame mode, only a single laser pulse exposes a frame as the positioning stage scans. In this mode, the effects of stage vibration are reduced by virtue of the short exposure pulse, and improved sensor MTF over a sensor, such as a TDI sensor. TDI mode entails integrating multiple excimer laser pulses, thus improving speckle smoothing and reducing peak power. The data acquisition subsystem can use a single sensor, which may have a large area for sensing in accordance with the description above. The sensor may fill the imaging field of view to maximize the available area and decrease peak powers.

Multiple sensors may also be employed to reduce the overall cost of the sensor, as use of more small sensors is typically less than use of one large sensor of similar area. These sensors may be located in relatively close proximity. They can be mounted on the same electronics board and even abutted together effectively producing a larger sensor. The sensors can also be spatially separated from each other, which provides certain advantages including the ability to pack all the readout electronics near the location of the sensor. The field of the imaging subsystem can be split into multiple parts using a scraping mirror, beam splitter, prism, grating, or diffractive optic. Each part can then be sent to one sensor. Ideally, the system splits at a field plane so the impact on the image fidelity is minimized. The sensors may also be located at different focal positions to gather focused and unfocused data simultaneously. Different imaging modes may also be employed by different sensors to simultaneously gather data, such as defect data. For example, the system may gather bright field and dark field data to determine different types of defects. Data acquisition can occur as the stage accelerates and decelerates. Synchronzation between the stage and remainder of the system enhances data acquisition and improves performance.

Data Analysis

The data analysis subsystem identifies anomalies or yield limiting defects on a specimen. The system primarily identifies defects using comparison techniques. One comparison technique used primarily for wafer inspection compares different dies. For example, if the system compares dies 1 and 2 and finds a difference at location A, and the system compares dies 2 and 3 and also finds a difference at location A, the system attributes a defect at location A to die 2.

The system may also compare between different cells within a die. In this scenario, the system defines a cell that repeats many times within the inspection area of interest. Cell comparison can be used for components having similar sub-areas within a die, such as memory and logic areas. The system may provide an adjustable magnification in the imaging subsystem so the system can adjust each cell to a relatively uniform number of sensor pixels.

A third comparison technique is die-to-database comparison. In order to compare data from the inspection to a database, the database must be rendered by accounting for performance of the imaging and sensor subsystems and their effect on the database. The system can then compare the rendered database to the data gathered by the inspection system.

Data is acquired in a continuous swath basis. Each swath can be allowed to slightly overlap with the previous and subsequent swaths so no data is lost. This overlapping region can also be used for accurately aligning the frames.

Data being compared may contain an integer number of pixels to aid in alignment of the data compared. Some frames of data can begin at known locations to simplify comparison. For example, in die-to-die comparison, computation is simplified if the beginning of each die is in the same location within a frame. The system accomplishes this alignment by adjusting the timing of the acquisition system and adjusting the frame overlap by a desired amount so the beginning on a first die and the beginning of a second die are located at the same position within a frame.

Defect data may be provided to other systems for further analysis such as e-beam review, macro review, or focused ion beam destructive analysis. The system may also provide semiconductor wafer data to yield management software for use in fab wide yield improvement.

The present system design may be employed in various environments, including but not limited to lithography, microscopy, biological inspection, medical research, and the like.

The design presented herein and the specific aspects illustrated are meant not to be limiting, but may include alternate components while still incorporating the teachings and benefits of the invention, namely the small design having a high NA able to be employed in various wavelengths using different illumination modes. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A system for inspecting a specimen, comprising:
    an illumination system comprising an arc lamp able to provide light energy having a wavelength in the range of less than approximately 320 nanometers; and
    an imaging subsystem oriented and configured to receive said light energy from said illumination system and direct light energy toward said specimen, said imaging subsystem comprising a plurality of elements all aligned along a single axis, each element having diameter less than approximately 100 millimeters, wherein the imaging subsystem is configured to provide a field size in excess of approximately 0.4 millimeters at a numerical aperture of approximately 0.90 for the light energy received from the illumination system having the wavelength in the range of less than approximately 320 nanometers.

2. The system of claim 1, wherein said plurality of elements comprises a mangin mirror arrangement.

3. The system of claim 1, said plurality of elements comprising collection optics for collecting light energy reflected from said specimen, wherein the collection optics are catadioptric.

4. The system of claim 3 where the catadioptric optics support wavelengths from approximately 266-600 nm.

5. The system of claim 1 where the imaging and illumination subsystems support at least one of a group of inspection modes comprising bright field, ring dark field, directional dark field, full sky, aerial imaging, confocal, and fluorescence.

6. The system of claim 1 where the imaging subsystem uses a varifocal system for the full magnification range.

7. The system of claim 1 where separate imaging lenses are used for specific magnification increments.

8. The system of claim 1, further comprising a data analysis subsystem for analyzing data representing the light energy reflected from the specimen, wherein the data analysis subsystem has the ability to record defect position for any defect on the specimen.

9. A system for inspecting a specimen, comprising:
   an illumination system able to provide light energy having a wavelength within a predetermined range; and
   an imaging subsystem oriented and configured to receive said light energy from said illumination system and direct light energy toward said specimen, said imaging subsystem comprising a plurality of optical elements all aligned along an axis and each having maximum diameter less than approximately 100 millimeters, wherein the imaging subsystem is configured to provide a field size in excess of approximately 0.4 millimeters at a numerical aperture of approximately 0.90.

10. The system of claim 9, wherein the predetermined range is approximately 285-320 nanometers.

11. The system of claim 9, wherein said plurality of optical elements comprises a mangin mirror arrangement.

12. The system of claim 9, wherein said plurality of optical elements comprises collection optics for collecting light energy reflected from said specimen, wherein the collection optics are catadioptric.

13. The system of claim 9, where the imaging and illumination subsystems support at least one of a group of inspection modes comprising bright field, ring dark field, directional dark field, full sky, aerial imaging, confocal, and fluorescence.

14. The system of claim 9, where the imaging subsystem uses a varifocal system for the full magnification range.

15. The system of claim 9, where separate imaging lenses are used for specific magnification increments.

16. The system of claim 9, further comprising a data analysis subsystem for analyzing data representing the light energy reflected from the specimen, wherein the data analysis subsystem has the ability to record defect position for any defect on the specimen.

17. A system for inspecting a specimen, comprising:
   an illumination system able to provide light energy having a wavelength within a predetermined range; and
   an imaging subsystem configured to receive said light energy and direct light energy toward said specimen using a plurality of elements having a maximum diameter less than approximately 100 millimeters, said plurality of elements being free of planar reflecting surfaces, wherein the imaging subsystem is configured to provide a field size in excess of approximately 0.4 millimeters at a numerical aperture of approximately 0.90.

18. The system of claim 17, wherein said plurality of elements comprises a mangin mirror arrangement.

19. The system of claim 17, further comprising a data analysis subsystem for analyzing data representing the light energy reflected from the specimen, wherein the data analysis subsystem has the ability to record defect position for any defect on the specimen.

20. A method for inspecting a specimen, comprising:
   providing light energy having a wavelength within a predetermined range; and
   receiving said light energy and directing light energy toward said specimen using a plurality of optical elements aligned collectively along a single axis, each optical element having maximum diameter less than approximately 100 millimeters, wherein the optical elements are configured to provide a field size in excess of approximately 0.4 millimeters at a numerical aperture of approximately 0.90.

21. The method of claim 20, wherein the predetermined range is approximately 285-320 nanometers.

22. The method of claim 20, wherein said plurality of optical elements comprises a mangin mirror arrangement.

23. The method of claim 20, wherein said plurality of optical elements comprises collection optics for collecting light energy reflected from said specimen, wherein the collection optics are catadioptric.

24. The method of claim 20, where providing and receiving and directing supports at least one of a group of inspection modes comprising bright field, ring dark field, directional dark field, full sky, aerial imaging, confocal, and fluorescence.

25. The method of claim 20, further comprising analyzing data representing the light energy reflected from the specimen, wherein analyzing data provides an ability to record defect position for any defect on the specimen.

* * * * *